United States Patent
Castro et al.

(10) Patent No.: US 10,314,827 B2
(45) Date of Patent: Jun. 11, 2019

(54) METHODS OF USE OF CYCLOPAMINE ANALOGS

(71) Applicant: Infinity Pharmaceuticals, Inc., Cambridge, MA (US)

(72) Inventors: Alfredo C. Castro, Winchester, MA (US); Michael J. Grogan, Winchester, MA (US); Karen J. McGovern, Groton, MA (US); Martin R. Tremblay, Melrose, MA (US)

(73) Assignee: Infinity Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 16/047,008

(22) Filed: Jul. 27, 2018

(65) Prior Publication Data
US 2018/0338962 A1 Nov. 29, 2018

Related U.S. Application Data

(63) Continuation of application No. 15/585,038, filed on May 2, 2017, now Pat. No. 10,045,970, which is a continuation of application No. 14/841,001, filed on Aug. 31, 2015, now Pat. No. 9,669,011, which is a continuation of application No. 14/054,350, filed on
(Continued)

(51) Int. Cl.
| | |
|---|---|
| *A61K 31/4355* | (2006.01) |
| *C07D 307/94* | (2006.01) |
| *C07D 471/04* | (2006.01) |
| *C07D 471/10* | (2006.01) |
| *A61K 31/58* | (2006.01) |
| *C07D 491/04* | (2006.01) |
| *C07D 491/10* | (2006.01) |
| *C07J 69/00* | (2006.01) |
| *A61K 31/17* | (2006.01) |
| *A61K 31/196* | (2006.01) |
| *A61K 31/198* | (2006.01) |
| *A61K 31/454* | (2006.01) |
| *A61K 31/4745* | (2006.01) |
| *A61K 31/519* | (2006.01) |
| *A61K 31/56* | (2006.01) |
| *A61K 31/573* | (2006.01) |
| *A61K 31/664* | (2006.01) |
| *A61K 31/69* | (2006.01) |
| *A61K 31/704* | (2006.01) |
| *A61K 31/7068* | (2006.01) |
| *A61K 31/7076* | (2006.01) |
| *A61K 38/21* | (2006.01) |
| *C07D 491/107* | (2006.01) |
| *A61K 45/06* | (2006.01) |
| *C07D 491/048* | (2006.01) |

(Continued)

(52) U.S. Cl.
CPC ........ *A61K 31/4355* (2013.01); *A61K 9/0014* (2013.01); *A61K 31/17* (2013.01); *A61K 31/196* (2013.01); *A61K 31/198* (2013.01); *A61K 31/454* (2013.01); *A61K 31/4745* (2013.01); *A61K 31/519* (2013.01); *A61K 31/56* (2013.01); *A61K 31/573* (2013.01); *A61K 31/58* (2013.01); *A61K 31/664* (2013.01); *A61K 31/69* (2013.01); *A61K 31/704* (2013.01); *A61K 31/7068* (2013.01); *A61K 31/7076* (2013.01); *A61K 38/21* (2013.01); *A61K 45/06* (2013.01); *A61N 5/10* (2013.01); *C07D 307/94* (2013.01); *C07D 471/04* (2013.01); *C07D 471/10* (2013.01); *C07D 491/04* (2013.01); *C07D 491/048* (2013.01); *C07D 491/10* (2013.01); *C07D 491/107* (2013.01); *C07J 69/00* (2013.01)

(58) Field of Classification Search
None
See application file for complete search history.

(56) References Cited

U.S. PATENT DOCUMENTS

| 4,843,071 A | 6/1989 | Hohenwarter |
| 4,968,787 A | 11/1990 | Inada et al. |
(Continued)

FOREIGN PATENT DOCUMENTS

| EP | 0255331 A2 | 2/1988 |
| EP | 0388188 A1 | 9/1990 |
(Continued)

OTHER PUBLICATIONS

Furio et al., "Transgenic kallikrein 5 mice reproduce major cutaneous and systemic hallmarks of Netherton syndrome", J. Exp. Med., vol. 211, No. 3, pp. 499-513 (2014).
(Continued)

*Primary Examiner* — Heidi Reese
(74) *Attorney, Agent, or Firm* — McDermott Will & Emery LLP; Judy M. Mohr; Wen Li

(57) ABSTRACT

The invention provides methods for treating various conditions using derivatives of cyclopamine having the following formula:

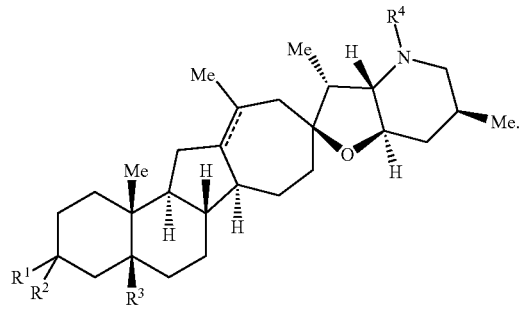

11 Claims, No Drawings

Related U.S. Application Data

Oct. 15, 2013, now Pat. No. 9,145,422, which is a continuation of application No. 13/475,510, filed on May 18, 2012, now abandoned, which is a continuation of application No. 13/090,694, filed on Apr. 20, 2011, now abandoned, which is a continuation of application No. 11/965,675, filed on Dec. 27, 2007, now Pat. No. 8,017,648.

(60) Provisional application No. 60/941,596, filed on Jun. 1, 2007, provisional application No. 60/878,018, filed on Dec. 28, 2006.

(51) Int. Cl.
*A61K 9/00* (2006.01)
*A61N 5/10* (2006.01)

(56) References Cited

U.S. PATENT DOCUMENTS

| | | |
|---|---|---|
| 5,086,047 A | 2/1992 | Gourvest et al. |
| 5,169,780 A | 12/1992 | Stirling et al. |
| 5,378,475 A | 1/1995 | Smith et al. |
| 5,767,161 A | 6/1998 | Stroppolo et al. |
| 6,177,407 B1 | 1/2001 | Rodgers et al. |
| 6,184,381 B1 | 2/2001 | Ikariya et al. |
| 6,238,876 B1 | 5/2001 | Altaba |
| 6,291,516 B1 | 9/2001 | Dudek et al. |
| 6,372,931 B1 | 4/2002 | Blacker et al. |
| 6,432,970 B2 | 8/2002 | Beachy et al. |
| 6,509,467 B1 | 1/2003 | Blacker et al. |
| 6,545,188 B2 | 4/2003 | Blacker et al. |
| 6,552,016 B1 | 4/2003 | Baxter et al. |
| 6,613,798 B1 | 9/2003 | Porter et al. |
| 6,686,388 B2 | 2/2004 | Dudek et al. |
| 6,867,216 B1 | 3/2005 | Beachy et al. |
| 6,887,820 B1 | 5/2005 | Ikariya et al. |
| 6,909,003 B2 | 6/2005 | Storz |
| 7,098,196 B1 | 8/2006 | Beachy et al. |
| 7,112,690 B2 | 9/2006 | Chi et al. |
| 7,230,004 B2 | 6/2007 | Adams et al. |
| 7,250,526 B2 | 7/2007 | Blacker et al. |
| 7,291,626 B1 | 11/2007 | Beachy et al. |
| 7,407,967 B2 | 8/2008 | Adams et al. |
| 7,476,661 B2 | 1/2009 | Beachy et al. |
| 7,541,183 B2 | 6/2009 | Rudnicki et al. |
| 7,605,167 B2 | 10/2009 | Tas et al. |
| 7,629,352 B2 | 12/2009 | Tas et al. |
| 7,648,994 B2 | 1/2010 | Castro et al. |
| 7,655,674 B2 | 2/2010 | Beachy et al. |
| 7,812,164 B2 | 10/2010 | Austad et al. |
| 7,867,492 B2 | 1/2011 | Beachy et al. |
| 7,875,628 B2 | 1/2011 | Adams et al. |
| 7,893,078 B2 | 2/2011 | Tas et al. |
| 7,964,590 B2 | 6/2011 | Castro et al. |
| 7,994,191 B2 | 8/2011 | Castro et al. |
| 8,017,648 B2 | 9/2011 | Castro et al. |
| 8,227,509 B2 | 7/2012 | Castro et al. |
| 8,236,956 B2 | 8/2012 | Adams et al. |
| 8,293,760 B2 | 10/2012 | Castro et al. |
| 8,426,436 B2 | 4/2013 | Castro et al. |
| 8,431,566 B2 | 4/2013 | Castro et al. |
| 8,669,365 B2 | 3/2014 | Austad et al. |
| 8,703,448 B2 | 4/2014 | Austad et al. |
| 8,716,479 B2 | 5/2014 | Austad et al. |
| 8,722,672 B2 | 5/2014 | Fritze et al. |
| 8,785,635 B2 | 7/2014 | Austad et al. |
| 8,895,576 B2 | 11/2014 | Castro et al. |
| 9,145,422 B2 | 9/2015 | Castro et al. |
| 9,238,672 B2 | 1/2016 | Austad et al. |
| 9,376,447 B2 | 6/2016 | Genov et al. |
| 9,394,313 B2 | 7/2016 | Genov et al. |
| 9,492,435 B2 | 11/2016 | Austad et al. |
| 2002/0006931 A1 | 1/2002 | Beachy et al. |
| 2002/0087258 A1 | 7/2002 | Johnson |
| 2002/0193347 A1 | 12/2002 | Bulliard et al. |
| 2003/0114393 A1 | 6/2003 | Liscovitch et al. |
| 2003/0162870 A1 | 8/2003 | Kimura et al. |
| 2003/0175355 A1 | 9/2003 | Tobyn et al. |
| 2003/0220314 A1 | 11/2003 | Shackleton et al. |
| 2004/0023949 A1 | 2/2004 | Baxter et al. |
| 2004/0072913 A1 | 4/2004 | Tas et al. |
| 2004/0072914 A1 | 4/2004 | Tas et al. |
| 2004/0073404 A1 | 4/2004 | Brooks et al. |
| 2004/0110663 A1 | 6/2004 | Dudek et al. |
| 2004/0126359 A1 | 7/2004 | Lamb et al. |
| 2004/0127474 A1 | 7/2004 | Dudek et al. |
| 2004/0247643 A1 | 12/2004 | Martinod et al. |
| 2005/0049218 A1 | 3/2005 | Gilbertson |
| 2005/0112707 A1 | 5/2005 | Altaba et al. |
| 2005/0203061 A1 | 9/2005 | Yamashita et al. |
| 2006/0020020 A1 | 1/2006 | Dudek et al. |
| 2006/0074030 A1 | 4/2006 | Adams et al. |
| 2006/0094660 A1 | 5/2006 | Thomson |
| 2006/0128639 A1 | 6/2006 | Beachy |
| 2006/0142245 A1 | 6/2006 | Beachy et al. |
| 2006/0252073 A1 | 11/2006 | Yilmaz et al. |
| 2007/0003550 A1 | 1/2007 | Antonia et al. |
| 2007/0009530 A1 | 1/2007 | Altaba et al. |
| 2007/0021493 A1 | 1/2007 | Guicherit et al. |
| 2007/0036800 A1 | 2/2007 | Bergstein |
| 2007/0060546 A1 | 3/2007 | Ruat et al. |
| 2007/0179091 A1 | 8/2007 | De Sauvage et al. |
| 2007/0191410 A1 | 8/2007 | Adams et al. |
| 2007/0219250 A1 | 9/2007 | Singh et al. |
| 2007/0231828 A1 | 10/2007 | Beachy et al. |
| 2007/0281040 A1 | 12/2007 | Weichselbaum et al. |
| 2008/0019961 A1 | 1/2008 | Wicha et al. |
| 2008/0057071 A1 | 3/2008 | Watkins et al. |
| 2008/0058298 A1 | 3/2008 | Beachy et al. |
| 2008/0089915 A1 | 4/2008 | Tas et al. |
| 2008/0095761 A1 | 4/2008 | Beachy et al. |
| 2008/0107749 A1 | 5/2008 | Maitra et al. |
| 2008/0118493 A1 | 5/2008 | Beachy et al. |
| 2008/0138379 A1 | 6/2008 | Jennings-Spring |
| 2008/0182859 A1 | 7/2008 | Brunton et al. |
| 2008/0255059 A1 | 10/2008 | Beachy et al. |
| 2008/0262051 A1 | 10/2008 | Balkovec et al. |
| 2008/0269182 A1 | 10/2008 | Pluda et al. |
| 2008/0269272 A1 | 10/2008 | Adams et al. |
| 2008/0287420 A1 | 11/2008 | Castro et al. |
| 2008/0293754 A1 | 11/2008 | Austad et al. |
| 2008/0293755 A1 | 11/2008 | Castro et al. |
| 2009/0004257 A1 | 1/2009 | Venkatraman et al. |
| 2009/0012109 A1 | 1/2009 | Austad et al. |
| 2009/0041680 A1 | 2/2009 | Tamarkin et al. |
| 2009/0181997 A1 | 7/2009 | Grayzel et al. |
| 2009/0203713 A1 | 8/2009 | Beachy et al. |
| 2009/0208579 A1 | 8/2009 | Ueki et al. |
| 2009/0216022 A1 | 8/2009 | Austad et al. |
| 2009/0246841 A1 | 10/2009 | Jamieson et al. |
| 2009/0263317 A1 | 10/2009 | Chen et al. |
| 2009/0286822 A1 | 11/2009 | Tas et al. |
| 2009/0305338 A1 | 12/2009 | Ritala-Nurmi et al. |
| 2010/0003728 A1 | 1/2010 | Jayatilake et al. |
| 2010/0093625 A1 | 4/2010 | Tarasova et al. |
| 2010/0099116 A1 | 4/2010 | Faia et al. |
| 2010/0144775 A1 | 6/2010 | Castro et al. |
| 2010/0210515 A1 | 8/2010 | Nash et al. |
| 2010/0222287 A1 | 9/2010 | McGovern et al. |
| 2010/0273818 A1 | 10/2010 | Beachy et al. |
| 2010/0286114 A1 | 11/2010 | Thomas et al. |
| 2010/0286180 A1 | 11/2010 | Castro et al. |
| 2010/0297118 A1 | 11/2010 | MacDougall et al. |
| 2011/0009442 A1 | 1/2011 | Austad et al. |
| 2011/0034498 A1 | 2/2011 | McGovern et al. |
| 2011/0104254 A1 | 5/2011 | Tas et al. |
| 2011/0135739 A1 | 6/2011 | Carter et al. |
| 2011/0166353 A1 | 7/2011 | Adams et al. |
| 2011/0183948 A1 | 7/2011 | Levine et al. |
| 2011/0230509 A1 | 9/2011 | Castro et al. |
| 2012/0010229 A1 | 1/2012 | MacDougall et al. |
| 2012/0010230 A1 | 1/2012 | MacDougall et al. |
| 2012/0015934 A1 | 1/2012 | Castro et al. |

(56) References Cited

U.S. PATENT DOCUMENTS

| | | |
|---|---|---|
| 2012/0065218 A1 | 3/2012 | Castro et al. |
| 2012/0065399 A1 | 3/2012 | Genov et al. |
| 2012/0065400 A1 | 3/2012 | Genov et al. |
| 2012/0077834 A1 | 3/2012 | Castro et al. |
| 2012/0083484 A1 | 4/2012 | Castro et al. |
| 2012/0083607 A1 | 4/2012 | Austad et al. |
| 2012/0190742 A1 | 7/2012 | Silver |
| 2013/0102614 A1 | 4/2013 | Liu et al. |
| 2013/0108582 A1 | 5/2013 | Castro et al. |
| 2013/0108583 A1 | 5/2013 | Castro et al. |
| 2013/0109700 A1 | 5/2013 | Epstein, Jr. et al. |
| 2013/0143831 A1 | 6/2013 | Embil et al. |
| 2014/0107142 A1 | 4/2014 | Castro et al. |
| 2014/0371253 A1 | 12/2014 | Austad et al. |
| 2014/0371456 A1 | 12/2014 | Austad et al. |
| 2016/0168193 A1 | 6/2016 | Jayatilake et al. |
| 2016/0177354 A1 | 6/2016 | Austad et al. |
| 2016/0354368 A1 | 12/2016 | Brown et al. |
| 2017/0022212 A1 | 1/2017 | Austad et al. |
| 2017/0029433 A1 | 2/2017 | Genov et al. |

FOREIGN PATENT DOCUMENTS

| | | | |
|---|---|---|---|
| EP | | 0434570 A2 | 6/1991 |
| EP | | 1401438 B1 | 9/2005 |
| EP | | 2225254 A2 | 9/2010 |
| EP | | 2443926 A2 | 4/2012 |
| JP | | 2010-0514796 A | 5/2010 |
| WO | WO | 1994/020520 A1 | 9/1994 |
| WO | WO | 1995/018856 A1 | 7/1995 |
| WO | WO | 1996/017924 A2 | 6/1996 |
| WO | WO | 1997/013518 A1 | 4/1997 |
| WO | WO | 1999/049835 A1 | 10/1999 |
| WO | WO | 2000/018708 A1 | 4/2000 |
| WO | WO | 2000/041545 A2 | 7/2000 |
| WO | WO | 2001/009077 A1 | 2/2001 |
| WO | WO | 2001/019800 A2 | 3/2001 |
| WO | WO | 2001/026644 A2 | 4/2001 |
| WO | WO | 2001/027135 A3 | 4/2001 |
| WO | WO | 2001/049279 A2 | 7/2001 |
| WO | WO | 2001/074344 A2 | 10/2001 |
| WO | WO | 2001/090077 A1 | 11/2001 |
| WO | WO | 2002/030462 A2 | 4/2002 |
| WO | WO | 2002/078703 A1 | 10/2002 |
| WO | WO | 2002/078704 A1 | 10/2002 |
| WO | WO | 2003/011219 A2 | 2/2003 |
| WO | WO | 2003/088964 A1 | 10/2003 |
| WO | WO | 2003/088970 A2 | 10/2003 |
| WO | WO | 2004/020599 A2 | 3/2004 |
| WO | WO | 2004/058976 A2 | 7/2004 |
| WO | WO | 2005/013800 A2 | 2/2005 |
| WO | WO | 2005/032343 A2 | 4/2005 |
| WO | WO | 2005/033288 A2 | 4/2005 |
| WO | WO | 2005/042700 A2 | 5/2005 |
| WO | WO | 2006/026430 A1 | 3/2006 |
| WO | WO | 2006/028958 A2 | 3/2006 |
| WO | WO | 2006/050351 A2 | 5/2006 |
| WO | WO | 2006/078283 A2 | 7/2006 |
| WO | WO | 2007/053596 A1 | 5/2007 |
| WO | WO | 2007/054623 A2 | 5/2007 |
| WO | WO | 2007/059157 A1 | 5/2007 |
| WO | WO | 2007/093372 A1 | 8/2007 |
| WO | WO | 2007/120827 A2 | 10/2007 |
| WO | WO | 2007/123511 A2 | 11/2007 |
| WO | WO | 2007/131201 A2 | 11/2007 |
| WO | WO | 2008/011071 A1 | 1/2008 |
| WO | WO | 2008/037732 A1 | 4/2008 |
| WO | WO | 2008/063165 A1 | 5/2008 |
| WO | WO | 2008/070357 A2 | 6/2008 |
| WO | WO | 2008/083248 A1 | 7/2008 |
| WO | WO | 2008/083252 A2 | 7/2008 |
| WO | WO | 2008/089123 A2 | 7/2008 |
| WO | WO | 2008/109184 A1 | 9/2008 |
| WO | WO | 2008/109829 A1 | 9/2008 |
| WO | WO | 2008/110611 A1 | 9/2008 |
| WO | WO | 2008/112913 A1 | 9/2008 |
| WO | WO | 2008/131354 A2 | 10/2008 |
| WO | WO | 2009/086416 A1 | 7/2009 |
| WO | WO | 2009/086451 A1 | 7/2009 |
| WO | WO | 2009/099625 A2 | 8/2009 |
| WO | WO | 2009/126840 A1 | 10/2009 |
| WO | WO | 2010/000070 A1 | 1/2010 |
| WO | WO | 2010/002970 A2 | 1/2010 |
| WO | WO | 2010/085654 A1 | 7/2010 |
| WO | WO | 2011/017551 A1 | 2/2011 |
| WO | WO | 2011/041075 A1 | 4/2011 |
| WO | WO | 2011/057222 A1 | 5/2011 |
| WO | WO | 2011/063309 A1 | 5/2011 |
| WO | WO | 2012/006584 A2 | 1/2012 |
| WO | WO | 2012/006589 A2 | 1/2012 |
| WO | WO | 2012/037217 A1 | 3/2012 |
| WO | WO | 2013/049332 A1 | 4/2013 |
| WO | WO | 2014/093871 A1 | 6/2014 |

OTHER PUBLICATIONS

Kasutani et al., "Anti-IL-31 receptor antibody is shown to be a potential therapeutic option for treating itch and dermatitis in mice", British J. Pharmacol., vol. 171, No. 22, pp. 5049-5058 (2014).

Kaulmann et al., "Substrate spectrum of ω-transaminase from Chromobacterium violaceum DSM30191 and its potential for biocatalysis", Enzyme and Microbial Technology, vol. 41, Issue 5, pp. 628-637 (2007).

Samukawa et al., "Red ginseng inhibits scratching behavior associated with atopic dermatitis in experimental animal models", J. Pharmacol. Sci., vol. 118, No. 3, pp. 391-400 (2012).

Yamaura et al., "Repeated application of glucocorticoids exacerbate pruritus via inhibition of prostaglandin D2 production of mast cells in a murine model of allergic contact dermatitis", J. Toxicol. Sci., vol. 37, No. 6, pp. 1127-1134 (2012).

Aboulkassim et al., "Alteration of the PATCHED locus in superficial bladder cancer", Oncogene, vol. 22, No. 19, pp. 2967-2971 (2003).

Ahlford, "Asymmetric transfer hydrogenation of ketones, catalyst development and mechanistic investigation", Department of Organic Chemistry, Stockholm University, US-AB Stockholm, pp. 1-49 (2011).

Ailles and Siu, "Targeting the hedgehog pathway in cancer: can the spines be smoothened?", Clin. Cancer Res.; vol. 17, No. 8, pp. 2071-2073 (2011).

Alexandre et al., "Transcriptional activation of hedgehog target genes in *Drosophila* is mediated directly by the Cubitus interruptus protein, a member of the GLI family of zinc finger DNA-bindlnq proteins", Genes Dev., vol. 10, pp. 2003-2013 (1996).

Alonso et al., "Ru(arene)(amino alcohol)-catalyzed transfer hydrogenation of ketones: mechanism and origin of enantioselectivity", J. Am. Chem. Soc., vol. 121, pp. 9580-9588 (1999).

Athar et al., "Hedgehog signaling in skin development and cancer", Exp. Dermatol., vol. 15, No. 9, pp. 667-677 (2006).

Bailey et al., "Sonic hedgehog promotes desmoplasia in pancreatic cancer", Clin. Cancer Res., vol. 14, No. 19, pp. 5995-6004 (2008).

Bailey et al., "Sonic hedgehog paracrine signaling regulates metastasis and lymphangiogenesis in pancreatic cancer", Oncogene, vol. 28, No. 40, pp. 3513-3525 (2009).

Bale and Yu, "The hedgehog pathway and basal cell carcinomas", Human Molecular Genetics, vol. 10, No. 7, pp. 757-762 (2001).

Banerjee et al., "Recruitment of the sonic hedgehog signalling cascade in electroconvulsive seizure-mediated regulation of adult rat hippocampal neurogenesis", Eur. J. Neurosci., vol. 22, No. 7, pp. 1570-1580 (2005).

Bar et al., "Cyclopamine-mediated hedgehog pathway inhibition depletes stem-like cancer cells in glioblastoma", Stem Cells, vol. 25, No. 10, pp. 2524-2533 (2007).

Barken et al., "Noscapine inhibits human prostate cancer progression and metastasis in a mouse model," Anticancer Res., vol. 28, No. 6A, pp. 3701-3704 (2008).

Belloni et al., "Identification of Sonic hedgehog as a candidate gene responsible for holoprosencephaly", Nature Genetics, vol. 14, pp. 353-356 (1996).

(56) References Cited

OTHER PUBLICATIONS

Berge et al., "Pharmaceutical salts", J. Pharm. Sci., 66, No. 1, pp. 1-19 (1977).
Berger et al., "Regulator of G-protein signaling-5 induction in pericytes coincides with active vessel remodeling during neovascularization," Blood, vol. 105, No. 3, pp. 1094-1101 (2005).
Berman et al., "Medulloblastoma growth inhibition by hedgehog pathway blockade", Science, vol. 297, pp. 1559-1561 (2002).
Berman et al., "Widespread requirement for Hedgehog ligand stimulation in growth of digestive tract tumours", Nature, vol. 425, pp. 846-851 (2003).
Bhat et al., "Synthesis and biological evaluation of novel steroidal pyrazoles as substrates for bile acid transporters", Bioorg. Med. Chem. Lett., vol. 15, pp. 85-87 (2005).
Bhattacharya et al., "Role of Hedgehog signaling in ovarian cancer", Clin. Cancer Res., vol. 14, No. 23, pp. 7659-7666 (2008).
Biospace, Print News Article, "Infinity Pharmaceuticals, Inc. Announces Hedgehog Pathway Inhibitor Agreement with AstraZeneca PLC (AZN)", Cambridge, Mass., Nov. 12, 2007, (Prime Newswire), 2 pages, Retreived from the Internet: http://www.biospace.com/news_story.aspx?NewsEntityId=77067.
Brown and Keeler, "Structure-activity relation of steroid teratogens, 1. Jervine ring system", J. Agric. Food Chem., vol. 26, No. 3, pp. 561-563 (1978).
Brown and Keeler, "Structure-activity relation of steroid teratogens, 2. N-substituted jervines", J. Agric. Food Chem., vol. 26, No. 3, pp. 564-566 (1978).
Browne et al.,"Isolation of teratogenic alkaloids by reversed-phase high-performance liquid chromatography" Journal of Chromatography Biomedical Applications, vol. 336, pp. 211-220 (1984).
Business Wire, "Infinity Reports Update from Phase 2 Study of Saridegib Plus Gemcitabine in Patients with Metastatic Pancreatic Cancer", Infinity Pharmaceuticals, 3 pages, Jan. 27, 2012, Retrieved from the internet: http://www.businesswire.com/news/home/20120127005146/en/Infinity-Reports-Update-Phase-2-Study-Saridegib#.U3Us_IdV8E.
Campbell et al., "Direct Targeting of the Hedgehog pathway in primary chondrosarcoma xenografts with smoothened Inhibitor IPI-926", Infinity Pharmaceuticals, Inc., Presentation Poster, Abstract #LB380, 1 page (2011).
Cancer Cluster Salzburg, "CCS researchers identify imiquimod as novel Hedgehog pathway inhibitor in skin cancer", Apr. 29, 2014, retrieved form the Internet: URL: http://www.cancercluster-salzberg.at/#!CCS-researchers-identify-imiquimod-as-novel-Hedgehog-pathway-inhibitor-in-skin-cancer/axycm/5687b39c0cf23a10fe3c91fc, accessed on Sep. 28, 2016.
Carter et al., "Formulation for IPI-926 drug product, a novel oral Hedgehog pathway inhibitor in clinical development", Infinity Pharmaceuticals, Inc., Presentation Poster, Abstract #M1169, with Presentation Abstract, 2 pages (2009).
Caserta et al., "p63 overexpression induces the expression of sonic hedgehog", Mol. Cancer Res., vol. 4, No. 10, pp. 759-768 (2006).
Chaumeil, "Micronization: A method of improving the bioavailability of poorly soluble drugs", Methods Find. Exp. Clin. Pharmacol., vol. 20, No. 3, pp. 211-215 (1998).
Chen et al., "Inhibition of Hedgehog signaling by direct binding of cyclopamine to smoothened", Genes Dev., vol. 16, No. 21, pp. 2743-2748 (2002).
Chen et al., "Small molecule modulation of Smoothened activity", PNAS, vol. 99, No. 22, pp. 14071-14076 (2002).
Chen et al., "Targeting the hedgehog pathway to mitigate treatment resistance", Cell Cycle, vol. 6, Issue. 15, pp. 1826-1830 (2007).
Chen et al., "Sonic hedgehog dependent phosphorylation by CK1α and GRK2 is required for ciliary accumulation and activation of smoothened", PloS Biology, vol. 9, Issue. 6, No. e1001083, 16 pages (2011).
Christiansen et al., "Antiandrogenic steroidal sulfonylpyrazoles", J. Med. Chem., vol. 33, pp. 2094-2100 (1990).

Chung et al., "New targets for therapy in prostate cancer: modulation of stromal-epithelial interactions", Urology, vol. 62, Suppl. 5A, pp. 44-54 (2003).
Clement et al., "Hedgehog-GLI1 signaling regulates human glioma growth, cancer stem cell self-renewal and tumorigenicity", Curr. Biol., vol. 17, No. 2, pp. 165-172 (2007).
Clinton et al., "Steroidal heterocycles, VI. Formulation of A/B-cis 3-Ketosteroids. Preparation of 5β-Steroidal[3,2-c]pyrazoles", J. Org. Chem., vol. 27, pp. 2800-2807 (1962).
Comtex, "Infinity announces hedgehog pathway inhibitor agreement with AstraZeneca", Infinity Pharmaceutucals, PrimeWireNewswire via COMTEX News Network, 2 pages, Nov. 12, 2007, Retrieved from the internet: http://files.shareholder.com/downloads/INFI/0x0x144355/71ecb752-43b2-4a26-9867-8feea13ee93d/INFI_News_2007_11_12_General.pdf.
Cong et al., "Steroidal alkaloids from the roots and rhizomes of *Veratrum nigrum* L", Helvetica Chimica Acta, vol. 90, Issue 5, pp. 1038-1042 (2007).
Cooper et al., "Teratogen-mediated inhibition of target tissue response to Shh signaling", Science, vol. 280, pp. 1603-1607 (1998).
Corbit et al., "Vertebrate smoothened functions at the primary cilium", Nature, vol. 437 No. 7061, pp. 1018-1021 (2005).
Cutcliffe et al., "Clear cell sarcoma of the kidney: Up-regulation of neural markers with activation of the sonic hedgehog and Akt pathways", Clin. Cancer Res., vol. 11, No. 22, pp. 7986-7994 (2005).
Dakhova et al., "Global gene expression analysis of reactive stroma in prostate cancer", Clin. Cancer Res., vol. 15, No. 12, pp. 3979-3989 (2009).
Deng et al., "External preparation useful for preparing drug for treating infectious disease caused by fungi, comprises nanosized itraconazole and matrix", Database WPI, Thomson Scientific, London, GB, AN: 2011-H84807, PN: CN102085176, 4 pgs. (2011) Abstract.
Dersnah and Baird, "Chiral $\eta^6$-$C_6H_6$ ruthehium complexes", J. Org. Chem., vol. 127, C55-C58 (1977).
Dierks et al., "Essential role of stromally induced hedgehog signaling in B-cell malignancies", Nat. Med., vol. 13, No. 8, pp. 944-951 (2007) Pre Publication Article, DOI:10.1038/nm1614 pp. 1-8 (2007).
Dierks et al., "Expansion of Bcr-Abl-positive leukemic stem cells is dependent on Hedgehog pathway activation", Cancer Cell, vol. 14, No. 3, pp. 238-249 (2008).
Di Magliano and Hebrok, "Hedgehog signalling in cancer formation and maintenance", Nat. Rev., vol. 3, No. 12, pp. 903-911 (2003).
Djerassi and Gutzwiller, "Selective reduction of steroids by homogeneous catalytic hydrogenation", J. Am. Chem. Soc., vol. 88, No. 19, pp. 4537-4538 (1966).
Dormeyer et al., "Plasma membrane proteomics of human embryonic stem cells and human embryonal carcinoma cells", J. Proteome Res., vol. 7, No. 7, pp. 2936-2951 (2008).
Dörwald, "Side reactions in organic synthesis, a guide to successful synthesis design", Wiley-VCH, Verlag GmbH & Co. KGaA, Weinheim, ISBN:3-527-31021-5, p. IX of Preface and pp. 8-13 (2005).
Ehtesham et al., "Ligand-dependent activation of the hedgehog pathway in glioma progenitor cells", Oncogene, vol. 26, No. 39, pp. 5752-5761 (2007).
Engelman and Settleman, "Acquired resistance to tyrosine kinase inhibitors during cancer therapy", Curr, Opin. Genet. Dev., vol. 18, No. 1, pp. 73-79 (2008).
Everaere et al., "Ruthenium (II)-catalyzed asymmetric transfer hydrogenation of carbonyl compounds with 2-propanol and ephedrine-type ligands", Adv. Synth. Catal., vol. 345, No. 1&2, pp. 67-77 (2003).
Fahrenholtz et al., "Cycloprop[16α, 17α] androstanes", J. Med. Chem., vol. 15, No. 10, pp. 1056-1060 (1972).
Faia et al., "Depilation induced anagen as a model to study hedgehog pathway antagonist IPI-926: Implications for biomarker development", AACR Meeting Abstracts Online, Abstract #2827, with Infinity Pharmaceuticals Poster, 3 pages (2008).
Fan et al., "Hedgehog singaling promotes prostate xenograft tumor growth", Endocrinology, vol. 145, No. 8, pp. 3961-3970 (2004).

(56) References Cited

OTHER PUBLICATIONS

Feldmann et al., "Blockade of hedgehog signaling inhibits pancreatic cancer invasion and metastases: A new paradigm for combination therapy in solid cancers", Cancer Res., vol. 67, No. 5, pp. 2187-2196 (2007).
Feldmann et al., "An orally bioavailable small-molecule inhibitor of Hedgehog signaling inhibits tumor initiation and metastasis in pancreatic cancer", Mol. Cancer Ther., vol. 7, No. 9, pp. 2725-2735 (2008).
Geng et al., "Hedgehog signaling in the murine melanoma microenvironment", Angiogenesis, vol. 10, No. 4, pp. 259-267, DOI: 10.1007/s10456-007-9078-9 (2007).
Genov and Ager, "Asymmetric hydrogenation of ketones catalyzed by $Ru^{II}$-bicp complexes", Angew. Chem. Int. Ed. Engl., vol. 43, No. 21, pp. 2816-2819 (2004).
Giannis et al., "Synthesis of cyclopamine using a biomimetic and diastereoselective approach", Angew. Chem. Int. Ed., vol. 48, pp. 1-5 (2009).
Goldberg et al., "Resolution of odontogenic keratocysts of the jaw in basal cell nevus syndrome with GDC-0449", Arch Dematol., vol. 147, No. 7, pp. 839-841 (2011).
Green, "A new approach to the formal classification of covalent compounds of the elements", Journal of Organometallic Chemistry, vol. 500, Issue 1-2, pp. 127-148 (1995).
Grogan et al., "Synthesis and structure activity relationship of D-homo cyclopamine analogs: A-ring fused heterocyclic analogs", MEDI 97, 237th ACS National Meeting, Infinity Pharmaceuticals, Inc., Presentation Poster, with Presentation Abstract, 2 pgs. (2009).
Growdon et al., "Hedgehog pathway inhibitor cyclopamine suppresses Gli1 expression and inhibits serous ovarian cancer xenograft growth", 40th Annual Meeting on Women's Cancer, Feb. 5-8, 2009, Presentation Slides, 16 pages (2009).
"Guidance for industry: Clinical trial endpoints for the approval of cancer drugs and biologics", US Dept. of Health Services, FDA, CDER and CBER, Section III, p. 4-9 (2007).
Guijarro et al., "Achiral β-amino alcohols as efficient ligands for the ruthenium-catalysed asymmetric transfer hydrogenation of sulfinylimines", Tetrahedron Letters, vol. 52, Issue 7, pp. 789-791 (2011), pre-publication accepted manuscript, DOI:10.1016/j.tetlet.2010.12.031, 6 pgs. (2010).
Hald et al., "Evidence-based Danish guidelines for the treatment of Malassezia-related skin diseases", Acta Derm. Venereol., vol. 95, No. 1, pp. 12-19 (2015).
Hanahan et al., "Less is more, regularly: metronomic dosing of cytotoxic drugs can target tumor angiogenesis in mice", J. Clin. Inv., vol. 105, No. 8, pp. 1045-1047 (2000).
Harrington et al., "Targeted radiosensitisation by pegylated liposome-encapsulated 3', 5'-O-dipalmitoyl 5-iodo-2'-deoxyuridine in a head and neck cancer xenograft model," Br. J. Cancer, vol. 91, No. 2, pp. 366-373 (2004).
Harris et al., "Hedgehog signaling: Networking to nurture a premalignant tumor microenvironment", Mol. Cancer Res., vol. 9, No. 9, pp. 1165-1174 (2011).
Hashiguchi et al., "Asymmetric transfer hydrogenation of aromatic ketones catalyzed by chiral ruthenium (II) complexes", J. Am. Chem. Soc., vol. 117, No. 28, pp. 7562-7563 (1995).
Hashimoto, "Simmons-Smith reaction without hydroxyl groups", Chemical, vol. 61, No. 1, pp. 63-64 (2006) Japanese language with English translation.
Hawley's Condensed Chemical Dictionary, 15$^{th}$ edition, Lewis, ed., John Wiley & Sons, New York, pp. 38 and 100 (2007).
Heftmann, "Recent progress in the biochemistry of plant steroids other than steroids (saponins, glycoalkaloids, pregnane derivatives, cardiac glycosides, and sex hormones)", Lipids, vol. 9, No. 8, pp. 626-639 (1974).
Hegde et al., "Hedgehog-induced survival of B-cell chronic lymphocytic leukemia cells in a stromal cell microenvironment: a potential new therapeutic target", Mol. Cancer Res., vol. 6, No. 12, pp. 1928-1936 (2008).

Heretsch et al., "Cyclopamine and hedgehog signaling: chemistry, biology, medical perspectives", Angew. Chem. Int. Ed., vol. 49, pp. 2-12, DOI: 10.1002/anie.200906967 (2010).
Holton and Necoechea, "Steroids. CLXXV. Further steroidal anabolic agents", J. Med. Chem., pp. 1352-1357 (1962).
Huangfu et al., "Hedgehog signalling in the mouse requires intraflagellar transport proteins", Nature, vol. 426, No. 6962, pp. 83-87 (2003).
Ikariya et al., "Bifunctional transition metal-based molecular catalysts for asymmetric syntheses", Org. Biomol. Chem., vol. 4, No. 3, pp. 393-406 (2006).
Incardona et al., "Cyclopamine inhibition of sonic hedgehog signal transduction is not mediated through effects on cholesterol transport", Dev. Biol., vol. 224, No. 2, pp. 440-452 (2000).
International Search Report from International Patent Application No. PCT/US2005/030406, 2 pages, dated Apr. 4, 2006, application now published as International Patent Publication No. WO2006/026430 on Mar. 9, 2006.
International Search Report from International Patent Application No. PCT/US2006/010796, 9 pages, dated May 15, 2008.
International Search Report from International Patent Application No. PCT/US2007/088990, 2 pages, dated Aug. 1, 2008.
International Search Report from International Patent Application No. PCT/US2007/088995, 6 pages, dated Aug. 1, 2008.
International Search Report from International Patent Application No. PCT/US2008/003200, 3 pages, dated Aug. 11, 2008.
International Search Report from International Patent Application No. PCT/US2008/050970, 3 pages, dated Aug. 22, 2008.
International Search Report from International Patent Application No. PCT/US2008/056229, 4 pages, dated Aug. 11, 2008.
International Search Report from International Patent Application No. PCT/US2008/088222, 6 pages, dated Feb. 23, 2009.
International Search Report from International Patent Application No. PCT/US2008/088302, 1 pages, dated Mar. 25, 2009.
International Search Report from International Patent Application No. PCT/US2009/049372, 3 pages, dated Mar. 16, 2010.
International Search Report from International Patent Application No. PCT/US2010/021816, 3 pages, dated Jun. 2, 2010.
International Search Report from International Patent Application No. PCT/US2010/044597, 2 pages, dated Oct. 1, 2010.
International Search Report from International Patent Application No. PCT/US2010/055879, 12 pages, dated Jan. 24, 2011.
International Search Report from International Patent Application No. PCT/US2010/057534, 2 pages, dated Jan. 18, 2011.
International Search Report from International Patent Application No. PCT/US2011/043446, 5 pages, dated Oct. 16, 2012.
International Search Report from International Patent Application No. PCT/US2011/043453, 4 pages, dated Mar. 14, 2012.
International Search Report from International Patent Application No. PCT/US2011/051553, 2 pages, dated Feb. 2, 2012.
International Search Report from International Patent Application No. PCT/US2016/035713, 8 pages, dated Nov. 9, 2016.
International Search Report from International Patent Application No. PCT/US2017/017247, 7 pages, dated Apr. 25, 2017.
Iselin et al., "Structure of jervine, VI. The sulfuric acid-catalyzed acetolysis of N-acetyl-3-deoxy-3 alpha.-chlorotetrahydro jervine", J. Am. Chem. Soc., vol. 76, pp. 5616-5620 (1954) Database Accession No. 1955:73589, XP-002672119, 4 pgs. (1954).
Iselin et al., "Jervine, IX. Miscellaneous new derivatives", J. Am. Chem. Soc., vol. 78, No. 2, pp. 403-407 (1956) Database Accession No. 1956:69487, XP-002672116. 3 pgs. (1956).
Jacobs and Craig, "The veratrine alkaloids, XXII. On pseudojervine and veratrosine, a companion glycoside in veratrum viride", J. Biol. Chem., vol. 155, 565-572 (1944).
Jacobs and Craig, "The veratrine alkaloids, XXV. The alkaloids of veratrum viride", J. Biol. Chem., vol. 160, pp. 555-565 (1945).
Jacobs and Huebner, "Veratrine alkaloids, XXVII. Further studies with jervine", J. Biol. Chem., vol. 170, pp. 635-652 (1947).
James et al., "Biomedical applications of poisonous plant research", J. Agric. Food Chem., vol. 52, pp. 3211-3230 (2004).
Ji et al., "Protein kinase A, not EPAC, suppresses hedgehog activity and regulates glucocorticoid sensitivity in acute lymphoblastic leukemia cells", J. Biol. Chem., vol. 282, No. 52, pp. 37370-37377 (2007).

(56) References Cited

OTHER PUBLICATIONS

Jiang et al., "Solution type spray of animycotic medicine for external application and its preparation method", Database WPI, Thomson Scientific, London, GB, AN: 2003-258153, PN: CN1380060, 4 pgs. (2002) Abstract.
Kaneko et al., "Biosynthesis of C-nor-D-homo-steroidal alkaloids from acetate-I-$^{14}$C, cholesterol-4-$^{14}$C and cholesterol-26-$^{14}$C in veratrum grandiflorum", Phytochemistry, vol. 9, pp. 2489-2495 (1970).
Kaneko et al., "11-deoxojervine as a precursor for jervine biosynthesis in veratrum grandiflorum", Phytochemistry, vol. 9, pp. 2497-2501 (1970).
Kaneko et al., "Conversion of solanidine to jervatrum alkaloids in veratrum grandiflorum", Phytochemistry, vol. 11, pp. 3199-3202 (1972).
Kaneko et al., "Biosynthesis of rubijervine in veratrum grandiflorum" Phytochemistry, vol. 14, pp. 1295-1301 (1975).
Kaneko et al., "Origin of nitrogen in the biosynthesis of solanidine by veratrum grandiflorum", Phytochemistry, vol. 15, pp. 1391-1393 (1976).
Kaneko et al., "Dormantinol, a possible precursor in solanidine biosynthesis from budding veratrum grandiflorum" Phytochemistry, vol. 16, pp. 1247-1251 (1977).
Karhadker et al., "Hedgehog signalling in prostate regeneration, neoplasia and metastasis", Nature, 431, pp. 707-712 (2004).
Kayed et al., "Distribution of indian hedgehog and its receptors patched and smoothened in human chronic pancreatitis". J. Endocrinol., vol. 178, No. 3, pp. 467-478 (2003).
Kayed et al., "Indian hedgehog signaling pathway: expression and regulation in pancreatic cancer", Int. J. Cancer; vol. 110, No. 5, pp. 668-676 (2004).
Keeler and Binns, "Chemical compounds of veratrum californicum related to congenital ovine cyclopian malformations: extraction of active material", Proc. Soc. Exptl. Biol. Med., vol. 116, pp. 123-127 (1964).
Keeler and Binns, "Teratogenic compounds of veratrum californicum (Durand), I. Preparation and characterization of fractions and alkaloids for biologic testing", Canadian Journal of Biochemistry, vol. 44, No. 6, pp. 819-828 (1966).
Keeler and Binns, "Teratogenic compounds of veratrum californicum (Durand), II. Production of ovine fetal cyclopia by fractions and alkaloid preparations", Can. J. Biochem., vol. 44, pp. 829-838 (1966).
Keeler, "Teratogenic compounds of veratrum californicum (Durand), IV. First isolation of veratramine and alkaloid Q and a reliable method for isolation of cyclopamine", Phytochemistry, vol. 7, pp. 303-306 (1968).
Keeler, "Toxic and teratogenic alkaloids of western range plants", J. Agr. Food Chem., vol. 17, No. 3, pp. 473-482 (1969).
Keeler, "Teratogenic Compounds of Veratrum Californicum (Durand) VII. The Structure of the glycosidic alkaloid cycloposine", Steroids, vol. 13, No. 5, pp. 579-588 (1969).
Keeler and Binns, "Teratogenic compounds of veratrum californicum as a function of plant part, stage, and site of growth", Phytochemistry, vol. 10, pp. 1765-1769 (1971).
Keeler, "Isolation of rubijervine from veratrum-californicum", Phytochemistry, vol. 13, pp. 2336-2337 (1974).
Keeler and Baker, "Oral, osmotic minipump, and intramuscular administration to sheep of the veratrum alkaloid cyclopamine (42970)", Cyclopamine Administration to Sheep, P.S.E.B.M., vol. 192, pp. 153-156 (1989).
Kenney et al., "Hedgehog and PI-3 kinase signaling converge on Nmyc1 to promote cell cycle progression in cerebellar neuronal precursors", Development, vol. 131, No. 1, pp. 217-228 (2004).
Kerbel and Kamen, "The anti-angiogenic basis of metronomic chemotherapy", Nature Rev., Cancer, vol. 4, pp. 423-436 (2004).
King, "Roughening up smoothened: chemical modulators of hedgehog signaling", J. Biol., vol. 1, No. 8, pp. 8.1-8.4 (2002).

Kitajima et al., "Steroid alkaloids of fresh bulbs of fritillaria thunbergii miq. and of crude drug "BAI-MO" prepared therefrom", Heterocycles, vol. 15, No. 2, pp. 791-796 (1981).
Koszelewski et al, "Formal asymmetric biocatalytic reductive amination", Angew. Chem. Int. Ed., vol. 47, No. 48, pp. 9337-9340 (2008).
Koszelewski et al., "ω-transaminases for the synthesis of non-racemic α-chiral primary amines", Trends Biotechnol., vol. 28, No. 6, pp. 324-332 (2010).
Kubo et al., "Hedgehog signaling pathway is a new therapeutic target for patients with breast cancer", Cancer Research, vol. 64, pp. 6071-6074 (2004).
Lacasse et al., "Iodomethylzinc phosphates: powerful reagents for the cyclopropanation of alkenes", J. Am. Chem. Soc., vol. 127, No. 36, pp. 12440-12441 (2005).
Lee et al., "Development of an enzyme-linked immunosorbent assay for the veratrum plant teratogens: cyclopamine and jervine", J. Agric. Food Chem., vol. 51, No. 3, pp. 582-586 (2003).
Leontjev et al., "Reduction of steroidal ketones with amine-boranes", Russian Chemical Bulletin, vol. 53, No. 3, pp. 703-708 (2004).
Lescarbeau et al., "Synthesis and structure activity relationship of D-homo cyclopamine hedgehog antagonists: 7-membered A-ring lactam analogs", MEDI 98, 237$^{th}$ ACS National Meeting, Infinity Pharmaceuticals, Inc., Poster, with Presentation Abstract, 2 pgs. (2009).
Lewis and Veltmaat, "Next stop, the twilight zone: hedgehog network regulation of mammary gland development", J. Mamm. Gland Biol. Neopl., vol. 9, No. 2, pp. 165-181 (2004).
Li et al., "Chemistry, bioactivity and geographical diversity of steroidal alkaloids from the Liliaceae family", Natural Product Reports, vol. 23, pp. 735-752 (2006).
Li et al., "Mesodermal deletion of transforming growth factor-β receptor II disrupts lung epithelial morphogenesis: cross-talk between TGF-β and sonic hedgehog pathways", J. Biol. Chem., vol. 283, No. 52, pp. 36257-36264 (2008).
Lin et al., "Self-renewal of acute lymphocytic leukemia cells is limited by the hedgehog pathway inhibitors cyclopamine and IPI-926", PLoS One, vol. 5, Issue 12, No. e15262, pp. 1-8 (2010).
Lindemann, "Stroma-initiated hedgehog signaling takes center stage in B-cell lymphoma", Cancer Res., vol. 68, No. 4, pp. 961-964 (2008).
Lipinski et al., "Dose- and route-dependent teratogenicity, toxicity, and pharmacokinetic profiles of the hedgehog signaling antagonist cyclopamine in the mouse", Toxicol. Sci. Advanced Access Publication, 28 pages, (2008).
Ma et al., "Frequent activation of the hedgehog pathway in advanced gastric adenocarcinomas", Carcinogenesis, vol. 26, No. 10, pp. 1698-1705 (2005).
Ma et al., "Study of sonic hedgehog signaling pathway related molecules in gastric carcinoma", World J. Gastroenterol., vol. 12, No. 25, pp. 3965-3969 (2006).
Ma et al., "Development of in vitro techniques for the important medicinal plant veratrum californicum", Planta Medica, vol. 72, pp. 1142-1148 (2006).
Mandley et al., "The Hh inhibitor IPI-926 delays tumor re-growth of a non-small cell lung cancer xenograft model following treatment with an EGFR targeted tyrosine kinase inhibitor", Infinity Pharmaceuticals, Inc., Presentation Poster, Abstract #5045, 1 page (2010).
Manna et al., "Metabolite identification of IPI-609, a novel and potent inhibitor of the hedgehog pathway, in different species", Infinity Pharmaceuticals, Inc., Presentation Poster, 1 page (2008).
Mao et al., "First example of asymmetric transfer hydrogenation in water induced by a chiral amino alcohol hydrochloride", Tetrahedron Letters, vol. 46, pp. 7341-7344 (2005).
Masamune et al., "11-Deoxojervine, a new alkaloid form veratrum species", Bull. Chem. Soc. Japan, vol. 38, No. 8, pp. 1374-1378 (1965).
Masamune et al., "Syntheses and NMR spectra of 22,27-imino-17,23-oxidojervane derivatives", Tetrahedron, vol. 23, No. 4, pp. 1591-1612 (1967).
Masamune et al., "Synthesis of jervine and related alkaloids", J, Am. Chem. Soc., vol. 89, No. 17, pp. 4521-4523 (1967).

(56) References Cited

OTHER PUBLICATIONS

Masumane et al., "The stereochemistry of dihydrojervine and related compounds: The ORD curves of 11-oxoetiojervanes and 11-oxoiminojervanes", Tetrahedron, vol. 25, Issue 19, pp. 4853-4871 (1969).
Mazur, "Azasteroids III. 3-aza-a-homo androgens", J. Org. Chem., vol. 28, pp. 248-250 (1963).
Meloni et al., "Smoothened signal transduction is promoted by G protein-coupled receptor kinase 2", Mol. Cell. Biol., vol. 26, No. 20, pp. 7550-7560 (2006).
Metcalfe and De Sauvage, "Hedgehog fights back: mechanisms of acquired resistance against smoothened antagonists", Cancer Res; vol. 71, No. 15, pp. 5057-5061 and 6087 (2011).
Mrozik et al., "Heterocyclic steroids in the antiinflammatory series", J. Med. Chem., vol. 7, pp. 584-589 (1964).
Müller-Röver et al., A comprehensive guide for the accurate classification of murine hair follicles in distinct cycle stages, J. Invest. Dermatol., vol. 117, No. 1, pp. 3-15 (2001).
Nakamura et al., "Induction of osteogenic differentiation by hedgehog proteins", Biochem. Biophys. Res. Comm., vol. 237, pp. 465-469 Article No. RC977156 (1997).
Niemann et al., "Indian hedgehog and β-catenin signaling: Role in the sebaceous lineage of normal and neoplastic mammalian epidermis". PNAS, vol. 100, Suppl. 1, pp. 11873-11880 (2003).
Nolan-Stevaux et al., "GLI1 is regulated through smoothened-independent mechanisms in neoplastic pancreatic ducts and mediates PDAC cell survival and transformation", Genes Dev., vol. 23, No. 1, pp. 24-36 (2009).
Noyori and Hashiguchi, "Asymmetric transfer hydrogenation catalyzed by chiral ruthenium complexes", Acc. Chem. Res., vol. 30, No. 2, pp. 97-102 (1997).
Oatis et al., "Isolation, purification and full NMR assignments to cyclopamine from veratrum californicum", Chemistry Central Journal, vol. 2, No. 12, 17 pgs. (2008).
Ohta et al., "Investigations on steroids. XI. Synthesis of steroidal oxazole, imidazole, and triazole", Chem. Pharm. Bull. vol. 16, No. 8, pp. 1487-1497 (1968).
Ohta et al., "p53-independent negative regulation of p21/cyclin-dependent kinase-interacting protein 1 by the sonic hedgehog-glioma-associated oncogene 1 pathway in gastric carcinoma Cells", Cancer Res., vol. 65, No. 23, pp. 10822-10829 (2005).
Oka and Hara, "Regiospecific Beckmann rearrangement of 3-oxo-4-ene steroid oximes", J. Org. Chem., vol. 43, No. 19, pp. 3790-3791 (1978).
Oka and Hara, "Synthesis of A-azasteroids by the use of specific Beckmann rearrangement", Chemistry and Industry, pp. 168-170 (1969).
Olive et al., "Inhibition of hedgehog signaling enhances delivery of chemotherapy in a mouse model of pancreatic cancer", Science, vol. 324, No. 5933, pp. 1457-1461 (2009).
Oro and Higgins, "Hair cycle regulation of hedgehog signal reception", Dev. Biol., vol. 255, No. 2, pp. 238-248 (2003).
Paladini et al., "Modulation of hair growth with small molecule agonists of the hedgehog signaling pathway", J. Invest. Dermatol., vol. 125, No. 4, pp. 638-646 (2005).
Pan et al., "Discovery of NVP-LDE225, a potent and selective smoothened antagonist", ACS Med. Chem. Lett., vol. 1, No. 3, pp. 130-134 (2010).
Park and Park, "Differential expression of Runx2 and indian hedgehog in cartilaginous tumors", Pathol. Oncol. Res., vol. 13, No. 1, pp. 32-37 (2007).
Park et al., "Composition useful for treating skin fungal infections, comprises itraconazole, phenol and phenolic alcohol", Database WPI, Thomson Scientific, London, GB, AN: 2010-F87592, PN: KR20100051293, 4 pgs. (2010) Abstract.
Park et al., "A crucial requirement for hedgehog signaling in small cell lung cancer", Nature Med., Author manuscript, vol. 17, No. 11, pp. 1504-1508, DOI: 10.1038/nm.2473 (2012).
Paryzek et al., "Ammonium formate/palladium on carbon: A versatile system for catalytic hydrogen transfer reductions of carbon-carbon double bonds", Synthesis, No. 13, pp. 2023-2026 (2003).
Patil et al., "Hedgehog signaling in human hepatocellular carcinoma", Cancer Biol. Ther., vol. 5, No. 1, pp. 111-117 (2006).
Peacock et al., "Hedgehog signaling maintains a tumor stem cell compartment in multiple myeloma", PNAS USA, vol. 104, No. 10, pp. 4048-4053 (2007).
Peacock et al., "Visualization of SMOOTHENED activation supports an essential role for hedgehog signaling in the regulation of self-renewal in small cell lung cancer", Infinity Pharmaceuticals, Inc., 1 page (2009).
Peluso et al., "Impact of the Smoothened inhibitor, IPI-926, on smoothened ciliary localization and Hedgehog pathway activity", PLOS ONE, vol. 9, Issue 3, No. e90534, 11 pages (2014).
Penova and Trandafiloff, "Intensification of extraction processes with tensides", Pharmazie, vol. 26, No. 8, pp. 489-490 (1971) With English Translation.
Philips et al., "Hedgehog signaling antagonist promotes regression of both liver fibrosis and hepatocellular carcinoma in a murine model of primary liver cancer", PLoS One, vol. 6, Issue 9, No. e23943, pp. 1-12 (2011).
Pietsch et al., "Medulloblastomas of the desmoplastic variant carry mutations of the human homologue of *Drosophila* patched", Cancer Research, vol. 57, pp. 2085-2088 (1997).
Pink et al., "Activity of IPI-926, a potent HH pathway inhibitor, in a novel model of medulloblastoma derived from Ptch/HIC +/− mice", Infinity Pharmaceuticals, Inc., AACR Meeting Abstracts Online, 99th AACR Annual Meeting, Apr. 13, 2008; San Diego, CA, Abstract #1588, Presentation Slides, 15 pages (2008).
Proctor et al., "Hedgehog signaling in castration resistant prostate cancer", AACR Annual Meeting, Apr. 17-21, 2010, Infinity Pharmaceuticals, Inc., Abstract #3857, Presentation Slides, 14 pages (2010).
Qualthrough et al., "Hedgehog signalling in colorectal tumour cells: induction of apoptosis with cyclopamine treatment" Int. J. Cancer, vol. 110, No. 6, pp. 831-837 (2004).
Quirk et al., "The smoothened gene and hedgehog signal transduction in *Drosophila* and vertebrate development", Cold Spring Harbor Symposium Quant. Biol., vol. 62, pp. 217-226 (1997).
Rahman et al., "Alkaloids from veratrum album", Phytochemistry, vol. 30, No. 1, pp. 368-370 (1991).
Rahman and Choudhary, "Chemistry and biology of steroidal alkaloids", The Alkaloids, Cordell, ed., Academic Press, San Diego, vol. 50, Ch. 2, pp. 61-108 (1998).
Rasmusson et al., "Azasteroids: structure-activity relationships for inhibition of 5α-reductase and of androgen receptor binding", J. Med. Chem., vol. 29, pp. 2298-2315 (1986).
Ravasio and Rossi, "Selective hydrogenations promoted by copper catalysts. 1. Chemoselectivity, regioselectivity, and stereoselectivity in the hydrogenation of 3-substituted steroids", J. Org. Chem., vol. 56, No. 13, pp. 4329-4333 (1991).
Read, "Direct targeting of tumor cells with smoothed inhibitor IPI-926", 2011 AACR Read IPI-926 Direct Targeting, Infinity Pharmaceuticals, Inc., Presentation Slides, 27 pages (2011).
Reddy et al., "A new novel and practical one pot methodology for conversion of alchohols to amines", Synthetic Communications, vol. 30, No. 12, pp. 2233-2237 (2000).
Reetz and Li, "An efficient catalyst system for the asymmetric transfer hydrogenation of ketones: remarkably broad substrate scope", J. Am. Chem. Soc., vol. 128, No. 4, pp. 1044-1045 (2006).
Reifenberger et al., "Missense mutations in SMOH in sporadic basal cell carcinomas of the skin and primitive neuroectodermal tumors of the central nervous system", Cancer Research, vol. 58, pp. 1798-1803 (1998).
Remingtons Pharmaceutical Sciences, 17$^{th}$ Edition, Gennaro, ed., Mack Publishing Company, Easton, Pennsylvania 18042, p. 1625 (1985).
Rohatgi et al., "Patched1 regulates hedgehog signaling at the primary cilium", Science, vol. 317, No. 5836, pp. 372-376 (2007).
Rominger et al., "Evidence for allosteric interactions of antagonist binding to the smoothened receptor", J. Pharmacol. Exp. Ther., vol. 329, No. 3, pp. 995-1005 (2009).

(56) References Cited

OTHER PUBLICATIONS

Ross, "A Study Evaluating IPI-926 in combination with gemcitabine in patients with metastatic pancreatic cancer", National Cancer Institute, Clinical Trials (PDQ®), Data processed on Oct. 17, 2013, 3 pgs., Retreived from the internet http://www.cancer.gov/clinicaltrials/search/view?cdrid=674592&version=HealthProfessional.
Rubin and De Sauvage, "Targeting the hedgehog pathway in cancer", Nature Rev., vol. 5, No. 12, pp. 1026-1033 (2006).
Rudin et al., "Treatment of medulloblastoma with hedgehog pathway inhibitor GDC-0449", N. Eng. J. Med., vol. 361, No. 12, pp. 1173-1178 (2009).
Rudin et al., "A phase 1 study of IPI-926, an inhibitor of the hedgehog pathway, in patients with advanced or metastatic solid tumors", Infinity Pharmaceuticals, Inc., Poster, 1 page. (2010).
Saldanha, "The hedgehog signalling pathway and cancer", J. Pathol., vol. 193, No. 4, pp. 427-432 (2001).
Sanganwar and Gupta, "Dissolution-rate enhancement of fenofibrate by adsorption onto silica using supercritical carbon dioxide", Int. J. Pharm., vol. 360, No. 1-2, pp. 213-218 (2008).
Sasson et al., "Homogeneous catalytic transfer-hydrogenation of a, β-unsaturated carbonyl compounds by dichlorotris (triphenylphosphine) ruthenium (II)", Tetrahedron Letters, vol. 12, Issue. 24, pp. 2167-2170 (1971).
Sato et al., "Induction of the hair growth phase in postnatal mice by localized transient expression of Sonic hedgehog", J. Clin. Invest., vol. 104, No. 7, pp. 855-864 (1999).
Sato et al., "Effect of adenovirus-mediated expression of sonic hedgehog gene on hair regrowth in mice with chemotherapy-induced alopecia", J. Natl. Cancer Inst., vol. 93, No. 24, pp. 1858-1864 (2001).
Sawada et al., "Asymmetric catalysis of intramolecular cyclopropanation of 5-aryl-1-diazo-1-mesitylsulfonyl-5-hexen-2-ones", Adv. Synth. Catal., vol. 347, Issue 11-13, pp. 1527-1532 (2005).
Shafaee et al., "Cyclopamine increases the cytotoxic effects of paclitaxel and radiation but not cisplatin and gemcitabine in hedgehog expressing pancreatic cancer cells", Cancer Chemother. Pharmacol., vol. 58, No. 6, pp. 765-770 (2006), Original Article, 6 pgs., DOI:10.1007/s00280-006-0227-4 (2006).
Shafiee et al., "Enzymatic deglycosylation of enfumafungin, a triterpene glycoside natural product, and its chemically synthesized analogues", J. Mol. Catalysis B: Enzymatic, vol. 16, pp. 27-32 (2001).
Shaw et al., "The sonic hedgehog pathway stimulates prostate tumor growth by paracrine signaling and recapitulates embryonic gene expression in tumor myofibroblasts", Oncogene, vol. 28, No. 50, pp. 4480-4490 (2009).
Sheng et al., "Activation of the hedgehog pathway in advanced prostate cancer", Molecular Cancer, vol. 3, No. 29, 13 pages (2004).
Sheng et al., "Regulation of Gli1 localization by the cAMP/protein kinase A signaling axis through a site near the nuclear localization signal", J. Biol. Chem. vol. 281, No. 1, pp. 9-12 (2006).
Shibasaki et al., "Hydrolysis of conjugated steroids by the combined use of β-glucuronidase preparations from Helix pomatia and Ampullaria: Determination of urinary cortisol and its metabolites", Steroids, vol. 66, pp. 795-801 (2001).
Shin et al., "Hedgehog / WNT feedback supports regenerative proliferation of epithelial stem cells in bladder", Nature, vol. 472, No. 7341, pp. 110-114, Author Manuscript, 15 pgs. (2011).
Shiotani et al., "Sonic hedgehog and CDX2 expression in the stomach", J. Gastroenterol. Hepatol., vol. 23, Suppl. 2, pp. S161-S166 (2008).
Shner et al., "The sterospecificity of the hydrogenation of $16\alpha$-methyl-3-oxo-$\Delta^4$-unsaturated compounds", Chemistry of Natural Compounds, vol. 6, No. 1, pp. 48-51 (1970).
Shroff and Harper, "3-Aza-A-homoandrostenes" J. Med. Chem., vol. 12, No. 1, pp. 190-191 (1969).
Sicklick et al., "Hedgehog signaling correlates with hepatocellular carcinoma progression" J. Clinical Oncology, 2005 ASCO Annual Meeting Proceedings, vol. 23, No. 16s (Jun. 1 Supplement), Abstract #9610, 1 page (2005).
Sicklick et al., "Hedgehog signaling maintains resident hepatic progenitors throughout life", Am. J. Physiol. Gastrointenst. Liver Physiol., vol. 290, No. 5, pp. G859-G870 (2006).
Sicklick et al., "Dysregulatlon of the hedgehog pathway in human hepatocarcinogenesis", Carcinogenesis, vol. 27, No. 4, pp. 748-757 (2006).
Simmons and Smith, "A new synthesis of cyclopropanes from olefins", J. Am. Chem. Soc., vol. 80, No. 19, pp. 5323-5324 (1958).
Sims-Mourtada et al., "Hedgehog: an attribute to tumor regrowth after chemoradiotherapy and a target to improve radiation response", Clin. Cancer Res., vol. 12, No. 21, pp. 6565-6572 (2006).
Singh et al., "Hedgehog-producing cancer cells respond to and require autocrine hedgehog activity", Cancer Res.; vol. 71, No. 13, pp. 4454-4463 (2011).
Siu et al., "A first-in-human, phase I study of an oral hedgehog (HH) pathway antagonist, BMS-833923 (XL 139), in subjects with advanced or metastatic solid tumors", J. Clin Oncol., vol. 28, pp. 15s, Suppl. Abstract #2501, 3 pgs.(2010) Abstract Only.
Skipper et al., "In vivo efficacy of marimastat and chemoradiation in head and neck cancer xenografts", ORL, vol. 71, No. 1, pp. 1-5, Original Paper, DOI:10.1159/000163217 (2009).
Skvara et al., "Topical treatment of basal cell carcinomas in nevoid basal cell carcinoma syndrome with a smoothened inhibitor", J. Invest. Dermatol., vol. 131, No. 8, pp. 1735-1744 Original Article, DOI:10.1038/jid.2011.48 (2011).
Smith and Thomas, "Animal models for the study of squamous cell carcinoma of the upper aerodigestive tract: a historical perspective with review of their utility and limitations, Part A. Chemically-induced de novo cancer, syngeneic animal models of HNSCC, animal models of transplanted xenogeneic human tumors," Int. J. Cancer, vol. 118, No. 9, pp. 2111-2122 (2006).
Stanton et al., "Small-molecule modulators of the sonic hedgehog signaling pathway", Mol. Biosyst., vol. 6, pp. 44-54 (2010).
Stecca et al., "Melanomas require HEDGEHOG-GLI signaling regulated by interactions between GLI1 and the RAS-MEK/AKT pathways", PNAS, vol. 104, No. 14, pp. 5895-5900 (2007).
Steg et al., "Multiple gene expression analyses in paraffin-embedded tissues by TaqMan low-density array, application to hedgehog and Wnt pathway analysis in ovarian endometroid adenocarcinoma", J. Mol. Diagn., vol. 8, No. 1, pp. 76-83 (2006).
Suggs et al., "Facile homogeneous hydrogenations of hindered olefins with [Ir(cod)py(PCy$_3$)]PF$_6$", Tetrahedron Letters, vol. 22, Issue 4, pp. 303-306 (1981).
Suginome et al., "Synthesis of O,N-diacetyl-3β-hydroxy-5α,12α-jervan-11-one with 17-epi-configuration by hypoiodite reaction (1,2)", Tetrahedron Letters, vol. 14, No. 42, pp. 4147-4150 (1973).
Suginome et al., "Photo-induced Radical Rearrangements of Hypoiodite of N-Acetyljervine and the Related C-nor-D-Homosteroid in the Presence of Mercury (II) Oxide and Iodine", Bull. Chem. Soc. Japan, vol. 54, No. 10, pp. 3042-3047 (1981).
Suginome et al., "The transformation of Jervine into 18-Functional D-Homo-C-Norsteroids. IV. The Transformation of Jervine into (20R)-18,20-β-epoxy-3β-hydroxy-17β-ethyletiojervan-18-one 3-acetate via (20R)-18,20β-epoxy-3β-hydroxy-12α,17β-ethyletiojervan-11-one 3-acetate", Bull. Chem. Soc. Jpn., vol. 54, No. 3, pp. 852-861 (1981).
Sydor et al., "Activity of IPI-926, a novel inhibitor of the HH pathway, in subcutaneous and orthotopically implanted xenograft tumors that express SHH ligand", Eur. J. Cancer, Supplement, vol. 6, No. 12, p. 179, Poster 570 (2008).
Taipale et al., "Effects of oncogenic mutations in smoothened and patched can be reversed by cyclopamine", Nature, vol. 406, No. 6799, pp. 1005-1009 (2000).
Tang et al., "Antitumor activity of extracts and compounds from the rhizomes of Veratrum dahuricum", Phytother. Res., vol. 22, No. 8, pp. 1093-1096 (2008).
Tannock et al., "Docetaxel plus prednisone or mitoxantrone plus prednisone for advanced prostate cancer", N. Engl. J. Med., vol. 351, No. 15, pp. 1502-1512 (2004).
Tas and Avci, "Rapid clearance of psoriatic skin lesions induced by topical cyclopamine", Dermatology, vol. 209 pp. 126-131 (2004).

(56) References Cited

OTHER PUBLICATIONS

Taylor et al., "Novel biosynthetic approaches to the production of unnatural amino acids using transaminases", Trends Biotechnol., vol. 16, No. 10, pp. 412-418 (1998).
Thayer et al., "Hedgehog is an early and late mediator of pancreatic cancer tumorigenesis", Nature, vol. 425, pp. 851-856 (2003).
Thievessen et al., J. "Hedgehog signaling in normal urothelial cells and urothelial carcinoma cell lines", J. Cell Physiol., vol. 203, No. 2, pp. 372-377 (2005) Abstract Only.
Travaglione et al., "Activity of IPI-926, a novel inhibitor of the Hh pathway, in subcutaneous and orthotopically implanted xenograft tumors that express SHh ligand", Infinity Pharmaceuticals, Inc., Presentation Poster, 1 page (2008).
Travaglione et al., "A novel HH pathway inhibitor, IPI-926, delays recurrence post-chemotherapy in a primary human SCLC xenograft model", AACR Meeting Abstracts Online, 99$^{th}$ AACR Annual Meeting, Apr. 12-16, 2008, San Diego, CA, Abstract #4611, 2 pags (2008).
Travaglione et al., "Induction of tumor-derived hedgehog ligand by chemotherapy", Infinity Pharmaceuticals, Inc., Presentation Poster, Abstract #323, 1 page (2009).
Travaglione et al., "The Hh inhibitor IPI-926 enhances tumor perfusion and nab-paclitaxel activity in a pancreatic xenograft model", Infinity Pharmaceuticals, Inc., Presentation Poster, Abstract #LB-374, 1 page (2010).
Tremblay et al., "Synthesis of novel, chemically stable D-homo-cyclopamine analogs via a cyclopropanation/ring-expansion sequence", Infinity Pharmaceuticals, Inc., 1 page (2007).
Tremblay et al., "Semisynthetic cyclopamine analogues as potent and orally bioavailable hedgehog pathway antagonists", J. Med. Chem., vol. 51, No. 21, pp. 6646-6649 (2008).
Tremblay et al., "Synthesis and structure activity relationship of D-homo cyclopamine analogs: 3-substituted analogs", Infinity Pharmaceuticals, Inc., Presentation Poster, 1 page (2009).
Tremblay et al., "Discovery of IPI-926, a semi-synthetic clinical candidate that targets the hedgehog pathway", Infinity Pharmaceuticals, ACS Meeting Salt Lake City, UT on Mar. 25, 2009, Presentation Slides, 26 pages (2009).
Tremblay et al., "Discovery of a potent and orally active hedgehog pathway antagonist (IPI-926)", J. Med. Chem., vol. 52, No. 14, pp. 4400-4418 (2009).
Tremblay et al., "Recent patents for hedgehog pathway inhibitors for the treatment of malignancy", Expert Opin. Ther. Pat., vol. 19, No. 8, pp. 1039-1056 (2009).
Tremblay et al., "New Developments in the discovery of small molecule Hedgehog pathway antagonists", Curr. Opin. Chem. Biol., vol. 14, No. 3, pp. 428-435 (2010) Article in press, COCHBI-737, vol. 14, pp. 1-8 (2010).
Tremblay et al., "Development of multi-kilogram synthetic route to IPI-926, a novel hedgehog pathway antagonistic for the treatment of malignant diseases", Infinity Pharmaceuticals, Inc., Apr. 2, 2011, Presentation Slides, 29 pages (2011).
Tschesche et al., "Concerning the biosynthesis of steroid derivatives in the plant kingdom, 3$^{rd}$ mess.$^1$: Spirostanol-biogenesis from cholesterol-glucoside", Z. Naturforsch, vol. 21b pp. 494-495 (1966) German language with English translation.
Tsuji et al., "Highly stereoselective hydrogenation of 3-oxo4-ene and -1,4-diene steroids to 5β compounds with palladium catalyst", J. Org. Chem., vol. 45, pp. 2729-2731 (1980).
Turner et al., "Sonic hedgehog pathway inhibition alters epididymal function as assessed by the development of sperm motility", Journal of Andrology, vol. 27, No. 2, pp. 225-232 (2006).
Van Der Horst et al., "Hedgehog stimulates only osteoblastic differentiation of undifferentiated KS483 cells", Bone, vol. 33, No. 6, pp. 899-910 (2003).
Vanhook, "Focus issue: fine-tuning hedgehog signaling in development and disease", Sci. Signaling, vol. 4, Issue 200, No. eg10, pp. 1-2 (2011).
Van Weerden et al., "Human xenograft models as useful tools to assess the potential of novel therapeutics in prostate cancer", Br. J. Cancer, vol. 100, No. 1, pp. 13-18 (2009).
Veratrum nigrum, Wikipedia entry last updated Apr. 23, 2014, Retreived from the internet http://en.wikipedia.org/wiki/Veratrum_nigram.
Villavicencio et al., "The sonic hedgehog-patched-gli pathway in human development and disease", Am. J. Hum. Genet., vol. 67, No. 5, pp. 1047-1054 (2000).
Villavicencio et al., "Activity of the Hh pathway inhibitor IPI-926 in a mouse model of medulloblastoma", Infinity Pharmaceuticals, Inc., Abstract #3199, Presentation Poster, 1 page (2009).
Voituriez and Charette, "Enantioselective cyclopropanation with TADDOL-derived phosphate ligands", Adv. Synth. Catal., vol. 348, Issue 16-17, pp. 2363-2370 (2006).
Von Hoff et al., "Inhibition of the hedgehog pathway in advanced basal-cell carcinoma", N. Eng. J. Med., vol. 361, No. 12, pp. 1164-1172 (2009).
Wang et al., "Revision of structure of peimisine", Yao Xue Xue Bao, vol. 27, No. 4, pp. 273-278 (1992) Database Accession No. 1992:490583, (1992).
Wanshura et al., "Sequential activation of snail1 and N-Myc modulates sonic hedgehog-induced transformation of neural cells", Cancer Res.; vol. 71, No. 15, pp. 5336-5345 (2011).
Warzecha et al., "Inhibition of osteosarcoma cell proliferation by the hedgehog-inhibitor cyclopamine", J. Chemother., vol. 19, No. 5, pp. 554-561 (2007).
Watkins et al., "Hedgehog signaling within airway epithelial progenitors and in small-cell lung cancer", Nature, vol. 422, pp. 313-317 (2003).
Wei et al., "Indian hedgehog and its targets in human endometrium: menstrual cycle expression and response to CDB-2914", J. Clin. Endocrinol. Metab., vol. 95, No. 12, pp. 5330-5337 (2010).
Williams et al., "Identification of a small molecule inhibitor of the hedgehog signaling pathway: effects on basal cell carcinoma-like lesions", PNAS USA, vol. 100, No. 8, pp. 4616-4621 (2003).
Wintersteiner et al., "Structure of jervine, V. The sulfuric acid-catalyzed acetolysis of diacetyltetrahydrojervine", J. Am. Chem. Soc., vol. 76, No. 22, pp. 5609-5616 (1954) Database Accession No. 1955:73588 (1954).
Wong et al., "Primary cilia can both mediate and suppress Hedgehog pathway-dependent tumorigenesis", Nat. Med., vol. 15, No. 9, pp. 1055-1061 (2009).
Wu et al., "Chemical constituent of hubeibeimu, V. Isolation and identification of hupehenisine", Yaoxue Xuebao, vol. 21, No. 7, pp. 546-550 (1986) Database Accession No. 1987:15699 (1987).
Wunder et al., "Opportunities for improving the therapeutic ratio for patients with sarcoma", Lancet Oncol., vol. 8, No. 6, pp. 513-524 (2007).
Xie et al., "Activating smoothened mutations in sporadic basal-cell carcinoma", Nature, vol. 391, pp. 90-92 (1998).
Yamakawa et al., "CH/π attraction: the origin of enantioselectivity in transfer hydrogenation of aromatic carbonyl compounds catalyzed by chiralη$^6$-arene-ruthenium(II) complexes", Angew. Chem. Int. Ed., vol. 40, No. 15, pp. 2818-2821 (2001).
Yang and Hinds, "pRb-mediated control of epithelial cell proliferation and Indian Hedgehog expression in mouse intestinal development", BMC Developmental Biology, vol. 7, No. 6, pp. 1-12 (2007).
Yauch et al., "Smoothened mutation confers resistance to a hedgehog pathway inhibitor in medulloblastoma", Science, vol. 326, No. 5952, pp. 572-574 (2009).
Yoo et al., "Sonic hedgehog signaling promotes motility and invasiveness of gastric cancer cells through TGF-β-mediated activation of the ALK5-smad 3 pathway", Carcinogenesis, vol. 29, No. 3, pp. 480-490 (2008).
Yoshizaki et al., "Expressions of sonic hedgehog, patched, smoothened and Gli-1 in human intestinal stromal tumors and their correlation with prognosis", World J. Gastroenterol., vol. 12, No. 35, pp. 5687-5691 (2006).
Yu et al., "Chemical constituents of the unibract fritillary (*Fritillaria unibracteata*)", Zhongcaoyao, vol. 21, No. 1, pp. 2-6 (1990), Database Accession No. 1990:512481 (1990).

(56) References Cited

OTHER PUBLICATIONS

Yun et al., "Simultaneous synthesis of enantiomerically pure (R)-1-phenylethanol and (R)-α-methylbenzylamine from racemic α-methylbenzylamine using ω-transaminase/alcohol dehydrogenase/glucose dehydrogenase coupling reaction", Biotechnol. Lett., vol. 25, No. 10, pp. 809-814 (2003).

Yun et al., "ω-Amino acid: Pyruvate transaminase from Alcaligenes denitrificans Y2k-2: A new catalyst for kinetic resolution of β-amino acids and amines", Appl. Environ. Microbiol., vol. 70, No. 4, pp. 2529-2534 (2004).

Zanotti-Gerosa et al., "Ruthenium-catalysed asymmetric reduction of ketones, diphosphine ligands in hydrogenations for pharmaceutical synthesis", Platinum Metals Rev., vol. 49, No. 4, pp. 158-165 (2005).

Zassoinovich et al., "Asymmetric hydrogen transfer reactions promoted by homogeneous transition metal catalysts", Chem. Rev., vol. 92, No. 5, pp. 1051-1069 (1992).

Zeisberg and Neilson, "Biomarkers for epithelial-mesenchymal transitions", J. Clin. Invest., vol. 119, No. 6, pp. 1429-1437 (2009).

Zeng et al., "Neurosteroid analogues. 10. The effect of methyl group substitution at the C-6 and C-7 positions on the GABA modulatory and anesthetic actions of (3α,5α)- and (3α, 5β)-3-hydroxypregnan-20-one", J. Med. Chem., vol. 48, No. 8, pp. 3051-3059 (2005).

Zhang et al., "Hedgehog pathway responsiveness correlates with the presence of primary cilia on prostate stromal cells", BMC Developmental Biology, vol. 9, No. 50, pp. 1-7 (2009).

Zhao et al., "Studies on the constituents of veratrum plants II. Constituents of *Veratrum nigrum* L. var. *ussuriense* (1). Structure and $^1$H- and $^{13}$C-nuclear magnetic resonance spectra of a new alkaloid, verussurinine, and related alkaloids", Chem. Pharm. Bull., vol. 39, No. 3, 549-554 (1991).

Zhao et al., "Hedgehog signalling is essential for maintenance of cancer stem cells in myeloid leukaemia", Nature, vol. 460, No. 7255, pp. 652-656 (2009) Pre-Publication Article DOI: 10.1038/nature07737, pp. 1-5 (2009).

METHODS OF USE OF CYCLOPAMINE ANALOGS

CROSS-REFERENCE TO RELATED APPLICATIONS

This application is a continuation of U.S. patent application Ser. No. 15/585,038, filed May 2, 2017, now U.S. Pat. No. 10,045,970, which is a continuation of U.S. patent application Ser. No. 14/841,001, filed Aug. 31, 2015, now U.S. Pat. No. 9,669,011, which is a continuation of U.S. patent application Ser. No. 14/054,350, filed Oct. 15, 2013, now U.S. Pat. No. 9,145,422, which is a continuation of U.S. patent application Ser. No. 13/475,510, filed May 18, 2012, now abandoned, which is a continuation of U.S. patent application Ser. No. 13/090,694, filed Apr. 20, 2011, now abandoned, which is a continuation of U.S. patent application Ser. No. 11/965,675, filed Dec. 27, 2007, now U.S. Pat. No. 8,017,648, which claims priority to U.S. Patent Application No. 60/941,596, filed Jun. 1, 2007 and U.S. Patent Application No. 60/878,018, filed Dec. 28, 2006, each of which is hereby incorporated by reference in its entirety.

GOVERNMENT FUNDING

Some of the work described herein was done with government support under grant number K23 CA107040, awarded by the NIH/NCI. The government may have certain rights in the invention.

BACKGROUND OF THE INVENTION

The present invention generally relates to methods for antagonizing the hedgehog pathway and for treating various conditions using cyclopamine analogs.

Inhibition of the hedgehog pathway in certain cancers has been shown to result in inhibition of tumor growth. For example, anti-hedgehog antibodies have been shown to antagonize the function of the hedgehog pathway and inhibit the growth of tumors. Small molecule inhibition of hedgehog pathway activity has also been shown to result in cell death in a number of cancer types.

Research in this area has focused primarily on the elucidation of hedgehog pathway biology and the discovery of new hedgehog pathway inhibitors. Although inhibitors of the hedgehog pathway have been identified, there still exists the need to identify more potent inhibitors of the hedgehog pathway.

PCT publication WO 2006/026430 published 9 Mar. 2006 and assigned to the same assignee as the present application, discloses a wide variety of cyclopamine analogs, focusing on those with unsaturation in the A or B ring. In the present application, the surprisingly potent analogs contain completely saturated A and B rings.

SUMMARY OF THE INVENTION

The present invention relates to methods for treating hyperproliferative disorders and conditions mediated by the hedgehog pathway.

In one aspect, the invention relates to a method for treating a hyperproliferative disorder. The method includes administering to a subject an effective amount of a compound having the formula:

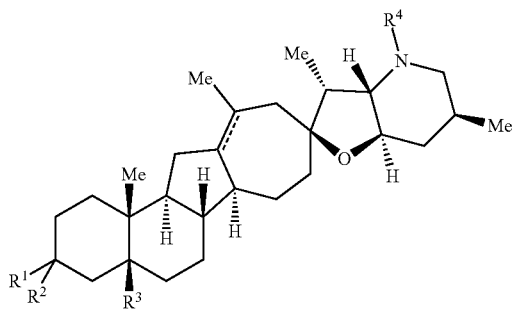

or a pharmaceutically acceptable salt thereof;

wherein $R^1$ is H, alkyl, —OR, amino, sulfonamido, sulfamido, —OC(O)$R^5$, —N($R^5$)C(O)$R^5$, or a sugar;

$R^2$ is H, alkyl, alkenyl, alkynyl, aryl, cycloalkyl, nitrile, or heterocycloalkyl; or $R^1$ and $R^2$ taken together form =O, =S, =N(OR), =N(R), =N(N$R_2$), =C(R)$_2$;

$R^3$ is H, alkyl, alkenyl, or alkynyl;

$R^4$ is H, alkyl, alkenyl, alkynyl, aryl, cycloalkyl, heterocycloalkyl, aralkyl, heteroaryl, heteroaralkyl, haloalkyl, —O$R^5$, —C(O)$R^5$, —CO$_2R^5$, —SO$_2R^5$, —C(O)N($R^5$)($R^5$), —[C(R)$_2$]$_q$—$R^5$, —[(W)—N(R)C(O)]$_q$$R^5$, —[(W)—C(O)]$_q$$R^5$, —[(W)—C(O)O]$_q$$R^5$, —[(W)—OC(O)]$_q$$R^5$, —[(W)—SO$_2$]$_q$$R^5$, —[(W)—N($R^5$)SO$_2$]$_q$$R^5$, —[(W)—C(O)N($R^5$)]$_q$$R^5$, —[(W)—O]$_q$$R^5$, —[(W)—N(R)]$_q$$R^5$, —W—N$R^5{}_3{}^+$$X^-$ or —[(W)—S]$_q$$R^5$;

wherein each W is independently for each occurrence a diradical;

each q is independently for each occurrence 1, 2, 3, 4, 5, or 6;

$X^-$ is a halide;

each R is independently H, alkyl, alkenyl, alkynyl, aryl, cycloalkyl or aralkyl; each $R^5$ is independently for each occurrence H, alkyl, alkenyl, alkynyl, aryl, cycloalkyl, heterocycloalkyl, aralkyl, heteroaryl, heteroaralkyl or —[C(R)$_2$]$_p$—$R^6$;

wherein p is 0-6; or where any two occurrences of $R^5$ on the same substituent can be taken together to form a 4-8 membered optionally substituted ring which contains 0-3 heteroatoms selected from N, O, S, and P;

each $R^6$ is independently hydroxyl, —N(R)COR, —N(R)C(O)OR, —N(R)SO$_2$(R), —C(O)N(R)$_2$, —OC(O)N(R)(R), —SO$_2$N(R)(R), —N(R)(R), —COOR, —C(O)N(OH)(R), —OS(O)$_2$OR, —S(O)$_2$OR, —OP(O)(OR)(OR), —NP(O)(OR)(OR), or —P(O)(OR)(OR).

In some embodiments, when $R^2$, $R^3$, and $R^4$ are H; $R^1$ is not hydroxyl or a sugar.

In some embodiments, when $R^4$ is hydroxyl, then $R^1$ is not a sugar or hydroxyl, and $R^1$ and $R^2$ together are not C=O.

In some embodiments, $R^1$ is sulfonamido.

The condition can be selected from the group consisting of skin cancers, cancers of the central nervous system, cancers of the gastrointestinal tract, cancers of the pulmonary system, genitourinary cancers, breast cancer, hepatocellular cancer, brain cancers, and cancers of the hematopoietic system.

In another aspect, the invention relates to a method of treating a condition mediated by the hedgehog pathway. The method includes administering to a subject an effective amount of a compound having the formula:

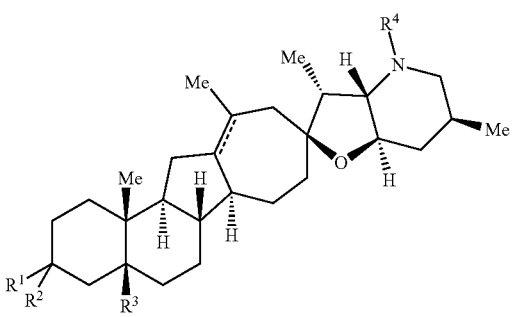

or a pharmaceutically acceptable salt thereof;

wherein $R^1$ is H, alkyl, —OR, amino, sulfonamido, sulfamido, —OC(O)$R^5$, —N($R^5$)C(O)$R^5$, or a sugar;

$R^2$ is H, alkyl, alkenyl, alkynyl, aryl, cycloalkyl, nitrile, or heterocycloalkyl; or $R^1$ and $R^2$ taken together form =O, =S, =N(OR), =N(R), =N(NR$_2$), =C(R)$_2$;

$R^3$ is H, alkyl, alkenyl, or alkynyl;

$R^4$ is H, alkyl, alkenyl, alkynyl, aryl, cycloalkyl, heterocycloalkyl, aralkyl, heteroaryl, heteroaralkyl, haloalkyl, —OR$^5$, —C(O)R$^5$, —CO$_2$R$^5$, —SO$_2$R$^5$, —C(O)N(R$^5$)(R$^5$), —[C(R)$_2$]$_q$—R$^5$, —[(W)—N(R)C(O)]$_q$R$^5$, —[(W)—C(O)]$_q$R$^5$, —[(W)—C(O)O]$_q$R$^5$, —[(W)—OC(O)]$_q$R$^5$, —[(W)—SO$_2$]$_q$R$^5$, —[(W)—N(R$^5$)SO$_2$]$_q$R$^5$, —[(W)—C(O)N(R$^5$)]$_q$R$^5$, —[(W)—O]$_q$R$^5$, —[(W)—N(R)]$_q$R$^5$, —W—NR$^5_3$$^+$X$^-$ or —[(W)—S]$_q$R$^5$;

wherein each W is independently for each occurrence a diradical;

each q is independently for each occurrence 1, 2, 3, 4, 5, or 6;

X$^-$ is a halide;

each R is independently H, alkyl, alkenyl, alkynyl, aryl, cycloalkyl or aralkyl;

each $R^5$ is independently for each occurrence H, alkyl, alkenyl, alkynyl, aryl, cycloalkyl, heterocycloalkyl, aralkyl, heteroaryl, heteroaralkyl or —[C(R)$_2$]$_p$—R$^6$;

wherein p is 0-6; or where any two occurrences of $R^5$ on the same substituent can be taken together to form a 4-8 membered optionally substituted ring which contains 0-3 heteroatoms selected from N, O, S, and P;

each $R^6$ is independently hydroxyl, —N(R)COR, —N(R)C(O)OR, —N(R)SO$_2$(R), —C(O)N(R)$_2$, —OC(O)N(R)(R), —SO$_2$N(R)(R), —N(R)(R), —COOR, —C(O)N(OH)(R), —OS(O)$_2$OR, —S(O)$_2$OR, —OP(O)(OR)(OR), —NP(O)(OR)(OR), or —P(O)(OR)(OR).

In some embodiments, when $R^2$, $R^3$, and $R^4$ are H; $R^1$ is not hydroxyl or a sugar.

In some embodiments, when $R^4$ is hydroxyl, then $R^1$ is not a sugar or hydroxyl, and $R^1$ and $R^2$ together are not C=O.

In some embodiments, $R^1$ is sulfonamido.

The condition can be selected from the group consisting of skin cancers, cancers of the central nervous system, cancers of the gastrointestinal tract, cancers of the pulmonary system, genitourinary cancers, breast cancer, hepatocellular cancer, brain cancers, and cancers of the hematopoietic system. Specific examples include small cell lung cancer, pancreatic cancer, medulloblastoma, multiple myeloma, leukemia, myelodysplastic syndrome, non-Hodgkin's lymphoma, and Hodgkin's disease. The compound may be administered orally, intravenously, or topically.

In another aspect, the invention relates to a method of antagonizing the hedgehog pathway in a subject. The method includes administering to the subject an effective amount of a compound having the formula:

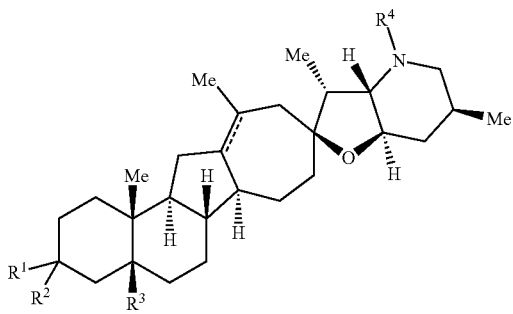

or a pharmaceutically acceptable salt thereof;

wherein $R^1$ is H, alkyl, —OR, amino, sulfonamido, sulfamido, —OC(O)R$^5$, —N(R$^5$)C(O)R$^5$, or a sugar;

$R^2$ is H, alkyl, alkenyl, alkynyl, aryl, cycloalkyl, nitrile, or heterocycloalkyl; or $R^1$ and $R^2$ taken together form =O, =S, =N(OR), =N(R), =N(NR$_2$), =C(R)$_2$;

$R^3$ is H, alkyl, alkenyl, or alkynyl;

$R^4$ is H, alkyl, alkenyl, alkynyl, aryl, cycloalkyl, heterocycloalkyl, aralkyl, heteroaryl, heteroaralkyl, haloalkyl, —OR$^5$, —C(O)R$^5$, —CO$_2$R$^5$, —SO$_2$R$^5$, —C(O)N(R$^5$)(R$^5$), —[C(R)$_2$]$_q$—R$^5$, —[(W)—N(R)C(O)]$_q$R$^5$, —[(W)—C(O)]$_q$R$^5$, —[(W)—C(O)O]R$^5$, —[(W)—OC(O)]$_q$R$^5$, —[(W)—SO$_2$]$_q$R$^5$, —[(W)—N(R$^5$)SO$_2$]$_q$R$^5$, —[(W)—C(O)N(R$^5$)]$_q$R$^5$, —[(W)—O]$_q$R$^5$, —[(W)—N(R)]$_q$R$^5$, —W—NR$^5_3$$^+$X$^-$ or —[(W)—S]$_q$R$^5$;

wherein each W is independently for each occurrence a diradical;

each q is independently for each occurrence 1, 2, 3, 4, 5, or 6;

X$^-$ is a halide;

each R is independently H, alkyl, alkenyl, alkynyl, aryl, cycloalkyl or aralkyl;

each $R^5$ is independently for each occurrence H, alkyl, alkenyl, alkynyl, aryl, cycloalkyl, heterocycloalkyl, aralkyl, heteroaryl, heteroaralkyl or —[C(R)$_2$]$_p$—R$^6$;

wherein p is 0-6; or where any two occurrences of $R^5$ on the same substituent can be taken together to form a 4-8 membered optionally substituted ring which contains 0-3 heteroatoms selected from N, O, S, and P;

each $R^6$ is independently hydroxyl, —N(R)COR, —N(R)C(O)OR, —N(R)SO$_2$(R), —C(O)N(R)$_2$, —OC(O)N(R)(R), —SO$_2$N(R)(R), —N(R)(R), —COOR, —C(O)N(OH)(R), —OS(O)$_2$OR, —S(O)$_2$OR, —OP(O)(OR)(OR), —NP(O)(OR)(OR), or —P(O)(OR)(OR).

In some embodiments, when $R^2$, $R^3$, and $R^4$ are H; $R^1$ is not hydroxyl or a sugar.

In some embodiments, when $R^4$ is hydroxyl, then $R^1$ is not a sugar or hydroxyl, and $R^1$ and $R^2$ together are not C=O.

In the embodiments described above, the compound may be selected from the group consisting of:

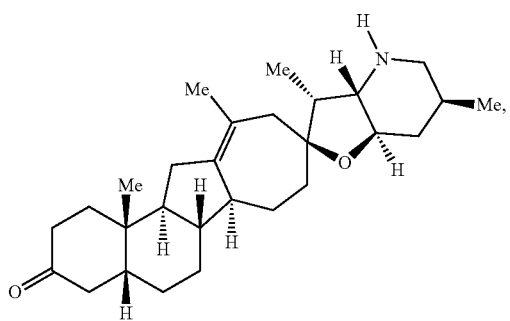
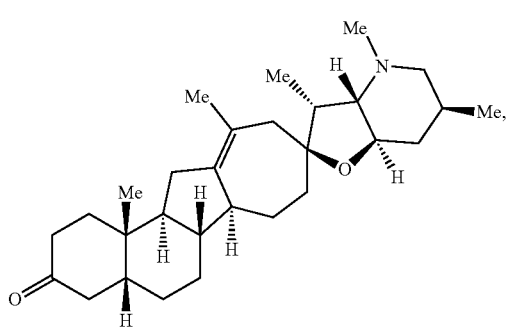
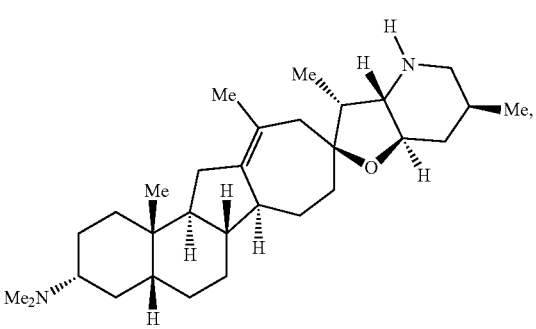
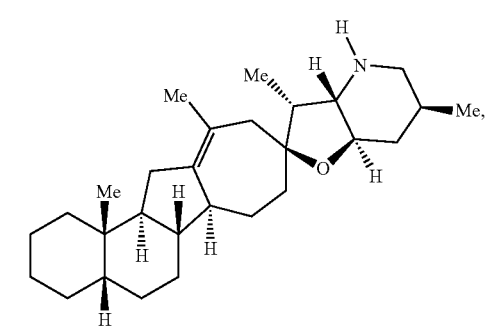
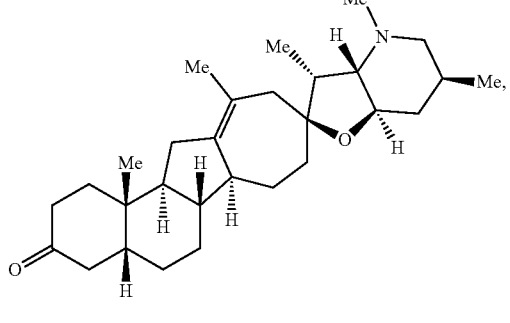
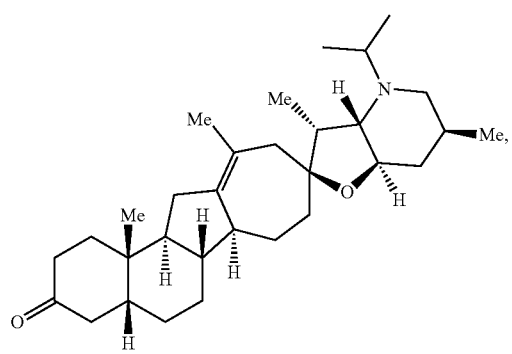
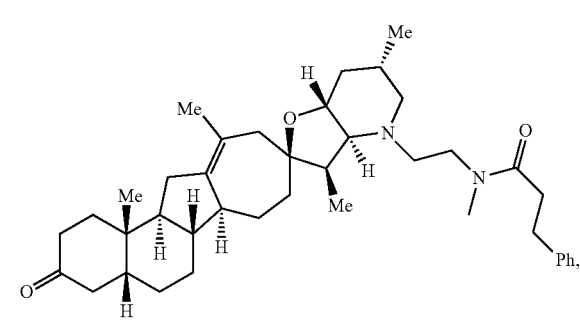
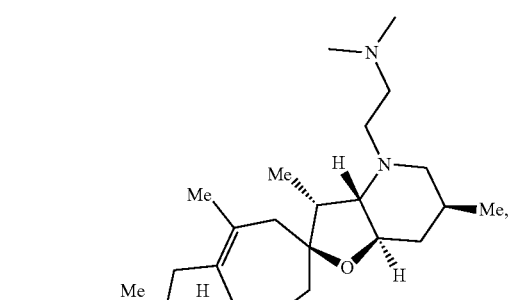
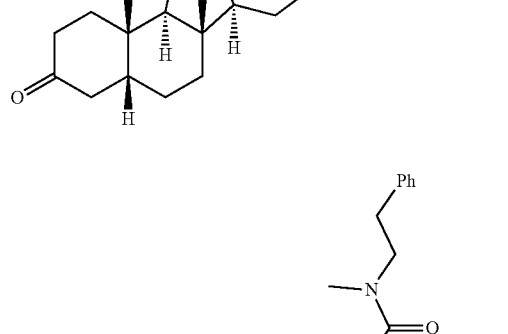
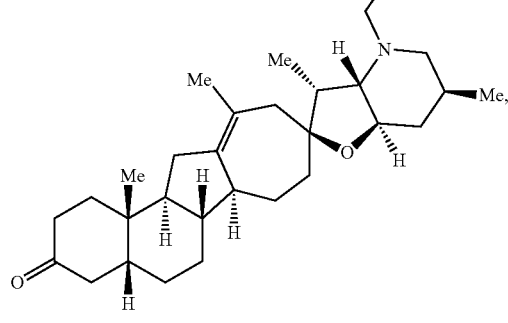

7
-continued
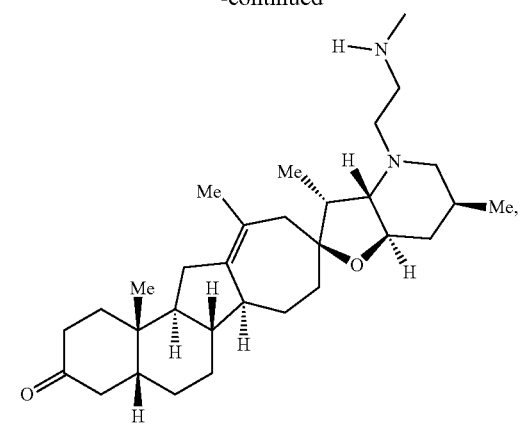
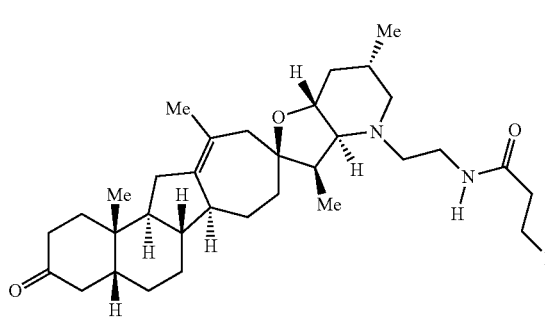
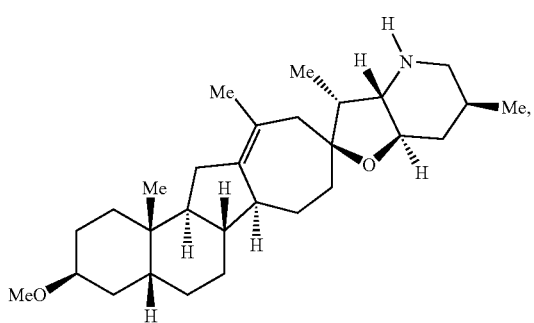
8
-continued
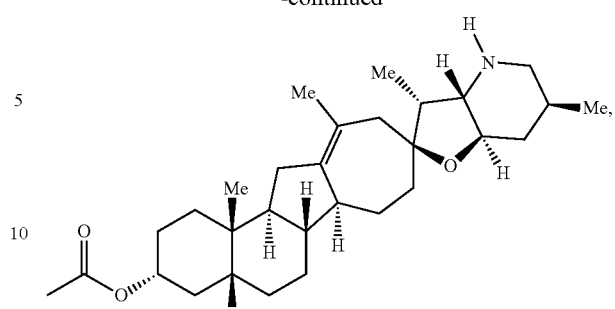
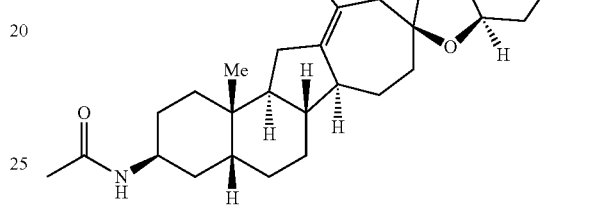
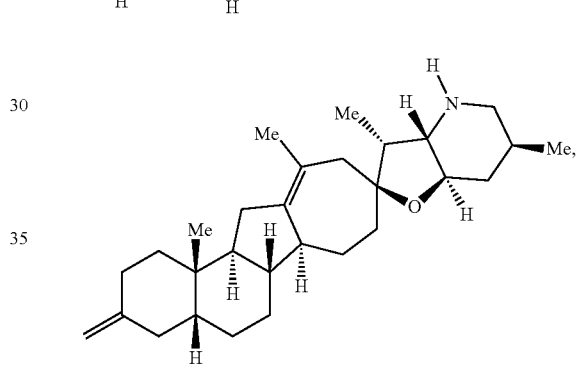
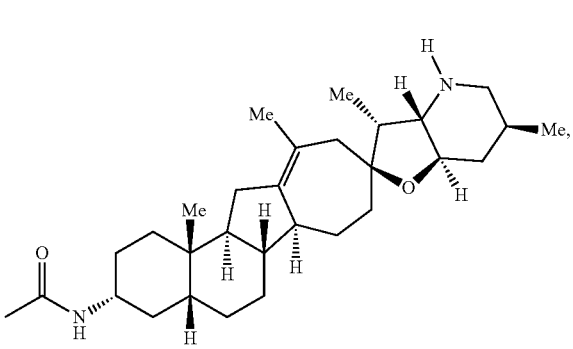
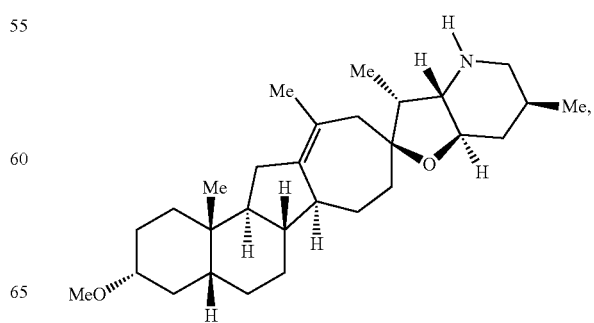

-continued
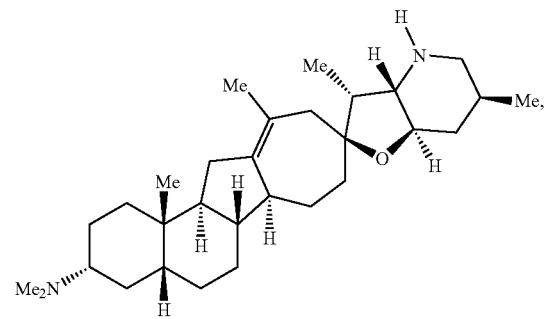
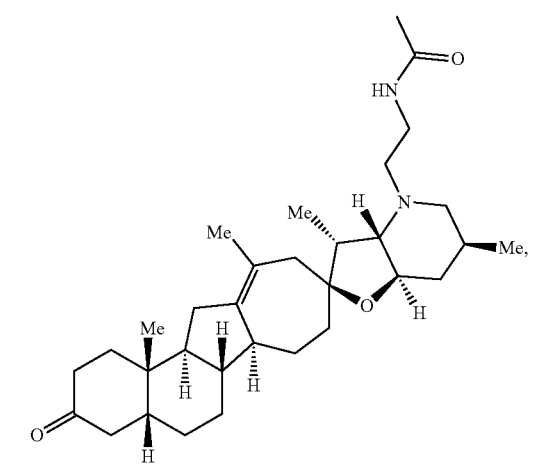
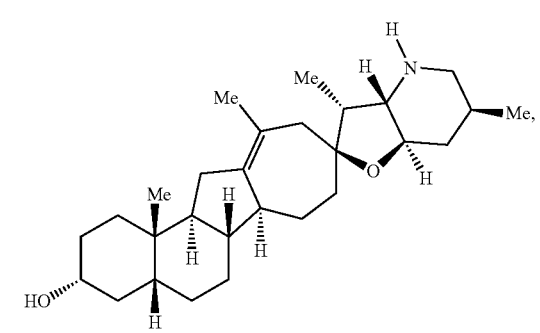
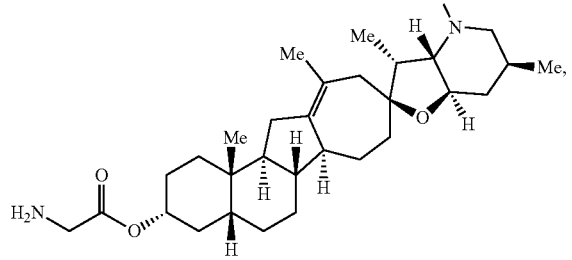
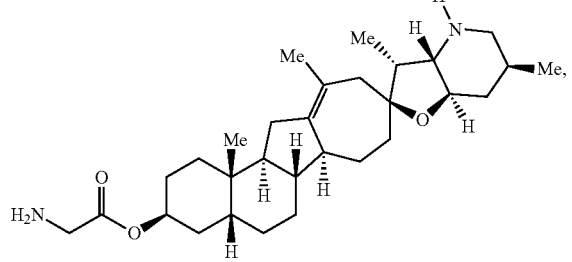
-continued
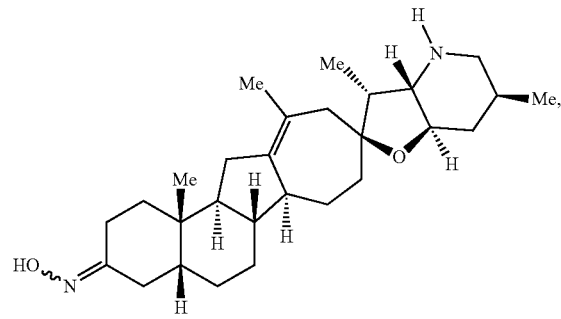
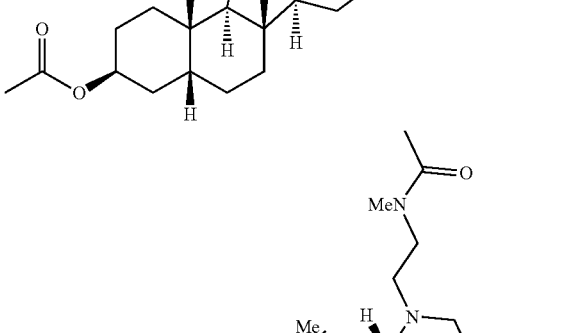
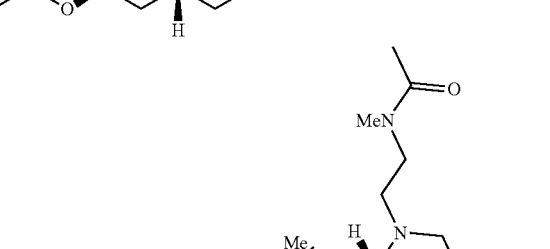
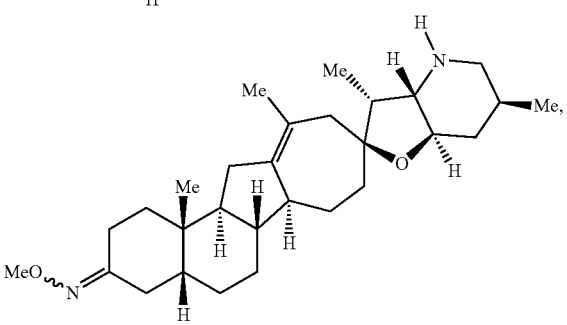

11
-continued
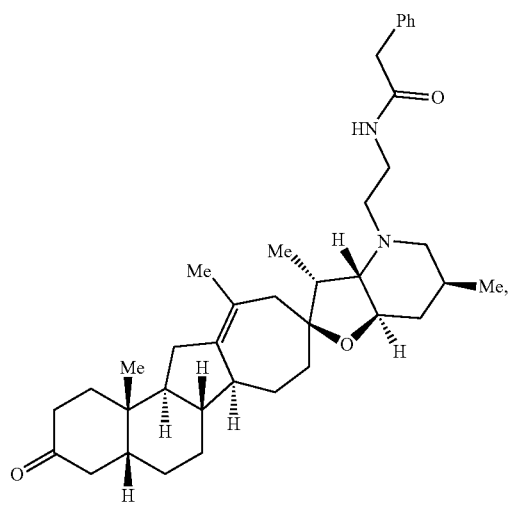
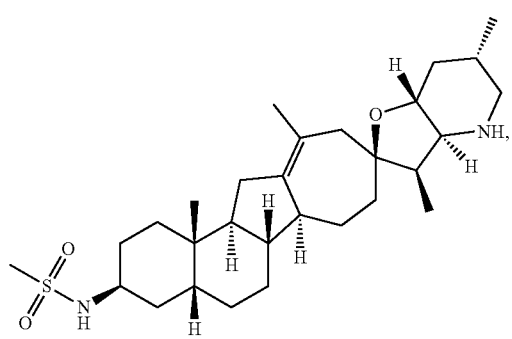
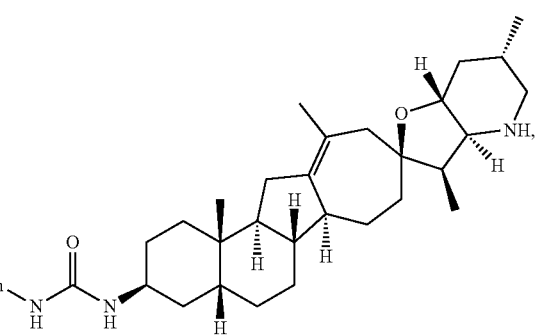
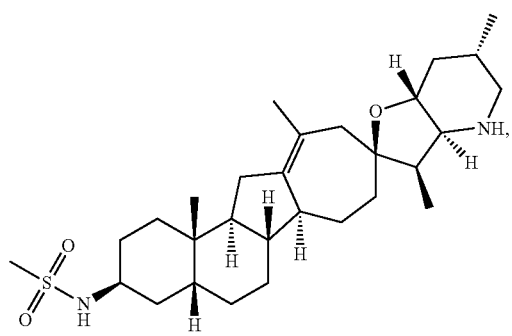
12
-continued
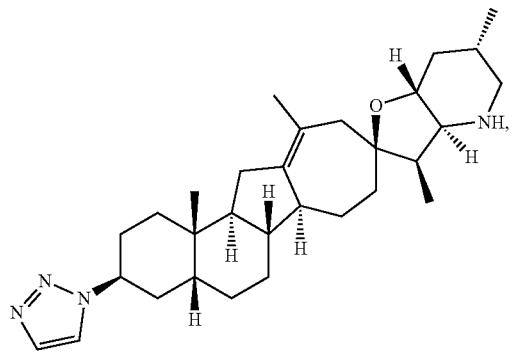
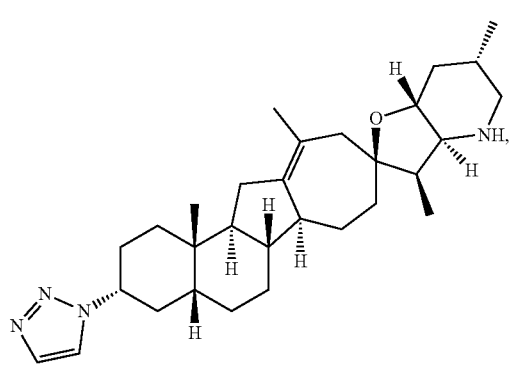
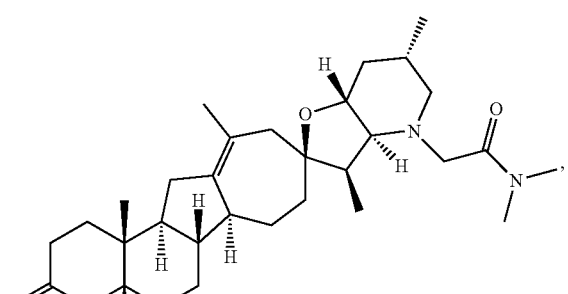
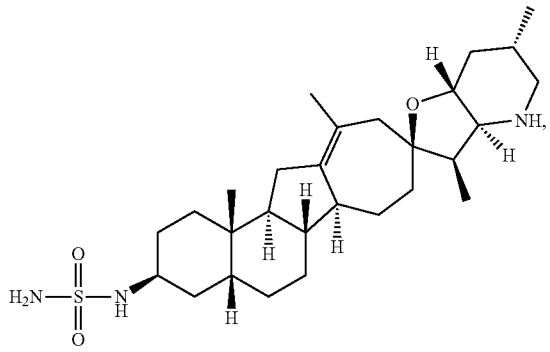

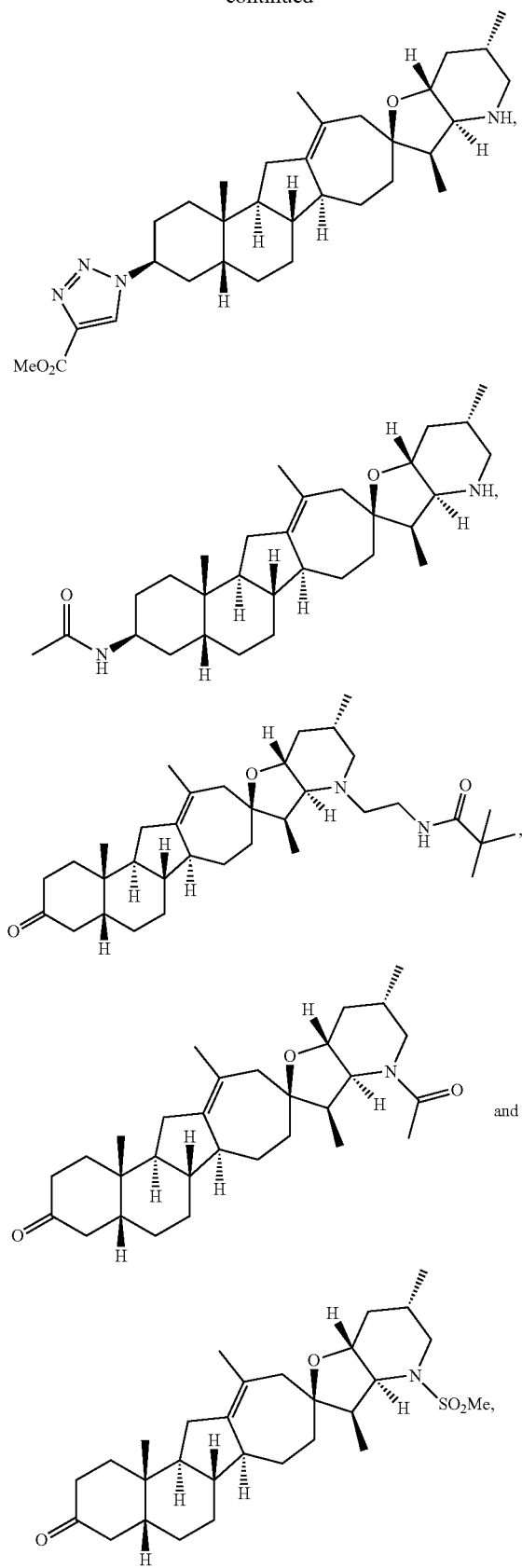

or a pharmaceutically acceptable salt thereof.

In another aspect, the invention relates to a method of antagonizing the hedgehog pathway in a subject. The method includes administering to the subject an effective amount of a compound having following structure:

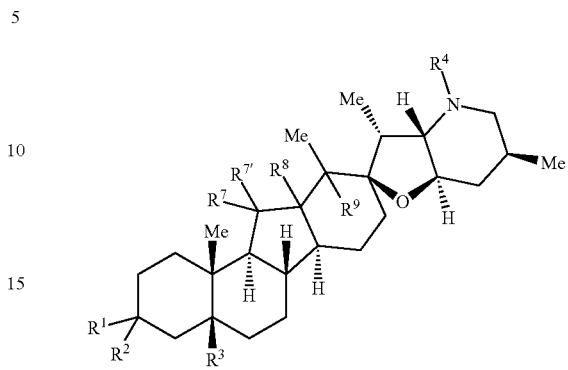

or a pharmaceutically acceptable salt thereof;
wherein $R^1$ is H, alkyl, —OR, amino, sulfonamido, sulfamido, —OC(O)$R^5$, —N($R^5$)C(O)$R^5$, or a sugar;
$R^2$ is H, alkyl, alkenyl, alkynyl, aryl, cycloalkyl, nitrile, or heterocycloalkyl; or $R^1$ and $R^2$ taken together form =O, =S, =N(OR), =N(R), =N(N$R_2$), =C(R)$_2$;
$R^3$ is H, alkyl, alkenyl, or alkynyl;
$R^4$ is H, alkyl, alkenyl, alkynyl, aryl, cycloalkyl, heterocycloalkyl, aralkyl, heteroaryl, heteroaralkyl, haloalkyl, —O$R^5$, —C(O)$R^5$, —CO$_2R^5$, —SO$_2R^5$, —C(O)N($R^5$)($R^5$), —[C(R)$_2$]$_q$—$R^5$, —[(W)—N(R)C(O)]$_q R^5$, —[(W)—C(O)]$_q R^5$, —[(W)—C(O)O]$_q R^5$, —[(W)—OC(O)]$_q R^5$, —[(W)—SO$_2$]$_q R^5$, —[(W)—N($R^5$)SO$_2$]$_q R^5$, —[(W)—C(O)N($R^5$)]$_q R^5$, —[(W)—O]$_q R^5$, —[(W)—N(R)]$_q R^5$, —W—N$R^5_3{}^+X^-$ or —[(W)—S]$_q R^5$;
wherein each W is, independently, a diradical;
each q is, independently, 1, 2, 3, 4, 5, or 6;
$X^-$ is a halide;
each R is independently H, alkyl, alkenyl, alkynyl, aryl, cycloalkyl or aralkyl;
each $R^5$ is, independently, H, alkyl, alkenyl, alkynyl, aryl, cycloalkyl, heterocycloalkyl, aralkyl, heteroaryl, heteroaralkyl or —[C(R)$_2$]$_p$—$R^6$;
wherein p is 0-6; or
any two occurrences of $R^5$ on the same substituent can be taken together to form a 4-8 membered optionally substituted ring which contains 0-3 heteroatoms selected from N, O, S, and P;
each $R^6$ is, independently, hydroxyl, —N(R)COR, —N(R)C(O)OR, —N(R)SO$_2$(R), —C(O)N(R)$_2$, —OC(O)N(R)(R), —SO$_2$N(R)(R), —N(R)(R), —COOR, —C(O)N(OH)(R), —OS(O)$_2$OR, —S(O)$_2$OR, —OP(O)(OR)(OR), —NP(O)(OR)(OR), or —P(O)(OR)(OR) where each R is independently H, alkyl, alkenyl, alkynyl, aryl, cycloalkyl or aralkyl;
each of $R^7$ and $R^{7'}$ is H; or
$R^7$ and $R^{7'}$ taken together form =O;
each $R^8$ and $R^9$ is H or $R^8$ and $R^9$ taken together form a bond; and provided that when $R^3$, $R^4$, $R^8$, $R^9$ are H and $R^7$ and $R^{7'}$ taken together form =O; $R^1$ cannot be hydroxyl and $R^2$ cannot be H;
provided that when $R^3$, $R^4$, $R^8$, $R^9$ are H and, $R^7$ and $R^{7'}$ taken together form =O; $R^1$ cannot be acetate and $R^2$ cannot be H;
provided that when $R^3$, $R^4$, $R^8$, $R^9$ are H and, $R^7$ and $R^8$ are H; $R^1$ and $R^2$ taken together cannot be =O; and provided that when $R^3$, $R^4$, $R^8$, $R^9$ are H and, $R^7$ and $R^{7'}$ are H; $R^1$ and $R^2$ cannot be H.

In some embodiments, $R^1$ is sulfonamido.

DETAILED DESCRIPTION OF THE INVENTION

Definitions

The definitions of terms used herein are meant to incorporate the present state-of-the-art definitions recognized for each term in the chemical and pharmaceutical fields. Where appropriate, exemplification is provided. The definitions apply to the terms as they are used throughout this specification, unless otherwise limited in specific instances, either individually or as part of a larger group.

As used herein, the definition of each expression, e.g., alkyl, m, n, etc., when it occurs more than once in any structure, is intended to be independent of its definition elsewhere in the same structure.

The term "acylamino" refers to a moiety that may be represented by the general formula:

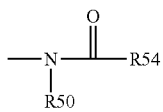

wherein R50 and R54 represent a hydrogen, an alkyl, an alkenyl or —(CH$_2$)$_m$—R61, where R61 represents an aryl, a cycloalkyl, a cycloalkenyl, a heterocycle or a polycycle; and m is zero or an integer in the range of 1 to 8.

The terms "alkenyl" and "alkynyl" refer to unsaturated aliphatic groups analogous in length and possible substitution to the alkyls described above, but that contain at least one double or triple bond respectively.

The terms "alkoxyl" or "alkoxy" refers to an alkyl group, as defined above, having an oxygen radical attached thereto. Representative alkoxyl groups include methoxy, ethoxy, propyloxy, tert-butoxy and the like.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has 30 or fewer carbon atoms in its backbone (e.g., C$_1$-C$_{30}$ for straight chain, C$_3$-C$_{30}$ for branched chain), 20 or fewer. Likewise, certain cycloalkyls have from 3-10 carbon atoms in their ring structure, and others have 5, 6 or 7 carbons in the ring structure.

The term "alkylthio" refers to an alkyl group, as defined above, having a sulfur radical attached thereto. In certain embodiments, the "alkylthio" moiety is represented by one of —S— alkyl, —S-alkenyl, —S-alkynyl, and —S—(CH$_2$)$_m$—R61, wherein m and R61 are defined above. Representative alkylthio groups include methylthio, ethyl thio, and the like.

The term "amido" is art recognized as an amino-substituted carbonyl and includes a moiety that may be represented by the general formula:

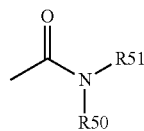

wherein R50 and R51 each independently represent a hydrogen, an alkyl, an alkenyl, —(CH$_2$)$_m$—R61, or R50 and R51, taken together with the N atom to which they are attached complete a heterocycle having from 4 to 8 atoms in the ring structure; R61 represents an aryl, a cycloalkyl, a cycloalkenyl, a heterocycle or a polycycle; and m is zero or an integer in the range of 1 to 8. Certain embodiments of the amide in the present invention will not include imides which may be unstable.

The terms "amine" and "amino" are art-recognized and refer to both unsubstituted and substituted amines, e.g., a moiety that may be represented by the general formulas:

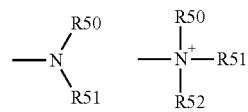

wherein R50, R51 and R52 each independently represent a hydrogen, an alkyl, an alkenyl, or —(CH$_2$)$_m$—R61, or R50 and R51, taken together with the N atom to which they are attached complete a heterocycle having from 4 to 8 atoms in the ring structure; R61 represents an aryl, a cycloalkyl, a cycloalkenyl, a heterocycle or a polycycle; and m is zero or an integer in the range of 1 to 8. Thus, the term "alkylamine" includes an amine group, as defined above, having a substituted or unsubstituted alkyl attached thereto, i.e., at least one of R50 and R51 is an alkyl group.

The term "aralkyl", as used herein, refers to an alkyl group substituted with an aryl group (e.g., an aromatic or heteroaromatic group).

The term "aryl" as used herein includes 5-, 6- and 7-membered single-ring aromatic groups that may include from zero to four heteroatoms, for example, benzene, anthracene, naphthalene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring may be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls.

The term "Brønsted acid" refers to any substance that can act as a hydrogen ion (proton) donor.

The term "carboxyl" includes such moieties as may be represented by the general formulas:

wherein X50 is a bond or represents an oxygen or a sulfur, and each of R55 and R56 represents independently a hydrogen, an alkyl, an alkenyl, —(CH$_2$)$_m$—R61 or a pharmaceutically acceptable salt, where m and R61 are defined above.

The term "diradical" refers to any of a series of divalent groups from alkyl, alkenyl, alkynyl, aryl, cycloalkyl, heterocycloalkyl, aralkyl, heteroaryl, and heteroaralkyl groups. For example,

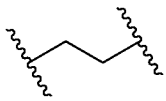 [SMILES: *CC*]

is an alkyl diradical;

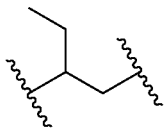 [SMILES: *CC(*)CC]

is also an alkyl diradical;

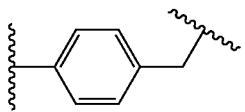 [SMILES: *Cc1ccc(*)cc1]

is an aralkyl diradical; and

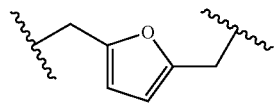 [SMILES: *Cc1ccc(C*)o1]

is an (alkyl)heteroaralkyl diradical. Typical examples include alkylenes of general structure (CH$_2$)$_x$ where X is 1-6, and corresponding alkenylene and alkynylene linkers having 2-6 carbon atoms and one or more double or triple bonds; cycloalkylene groups having 3-8 ring members; and aralkyl groups wherein one open valence is on the aryl ring and one is on the alkyl portion such as

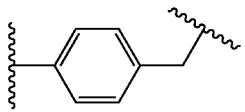

and its isomers.

An "effective amount" refers to an amount of compound which, when administered as part of a desired dosage regimen brings about a desired effect, e.g., a change in the rate of cell proliferation and/or rate of survival of a cell according to clinically acceptable standards for the disorder to be treated.

The term "haloalkyl", as used herein, refers to an alkyl group where anywhere from 1 to all hydrogens have been replaced with a halide. A "perhaloalkyl" is where all of the hydrogens have been replaced with a halide.

The term "heteroatom" as used herein means an atom of any element other than carbon or hydrogen. Examples of heteroatoms include boron, nitrogen, oxygen, phosphorus, sulfur and selenium.

The terms "heterocyclyl" or "heterocyclic group" refer to 3- to 10-membered ring structures, in some instances from 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring may be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The term "isolated" in connection with a compound of the present invention means the compound is not in a cell or organism and the compound is separated from some or all of the components that typically accompany it in nature.

The term "Lewis acid" refers to any substance that can act as an electron pair acceptor.

Unless the number of carbons is otherwise specified, "lower alkyl" as used herein means an alkyl group, as defined above, but having from one to ten carbons, in some embodiments from one to six carbon atoms in its backbone structure. Likewise, "lower alkenyl" and "lower alkynyl" have similar chain lengths. Certain alkyl groups are lower alkyls. In some embodiments, a substituent designated herein as alkyl is a lower alkyl.

As used herein, the term "nitro" means —NO$_2$; the term "halogen" designates —F, —Cl, —Br or —I; the term "sulfhydryl" means —SH; the term "hydroxyl" means —OH; and the term "sulfonyl" means —SO$_2$—.

The term "oxo" refers to a carbonyl oxygen (=O).

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle may be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The term "epimerically pure" in connection with a compound of the present invention means that the compound is substantially free of stereoisomers of the compound wherein the configuration of the stereogenic center that R$^3$ is bonded to is inverted. For example an epimerically pure compound represented by the following formula:

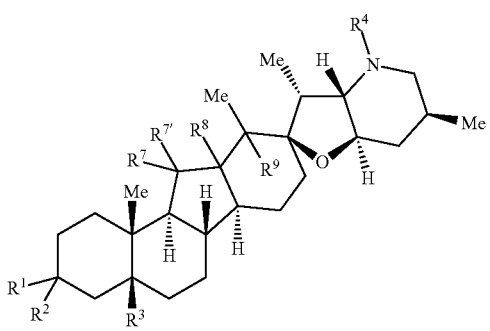

wherein $R^1$, $R^2$, $R^3$, $R^4$, $R^7$, $R^{7'}$, $R^8$, and $R^9$ are as defined below, is substantially free of compounds represented by the following formula:

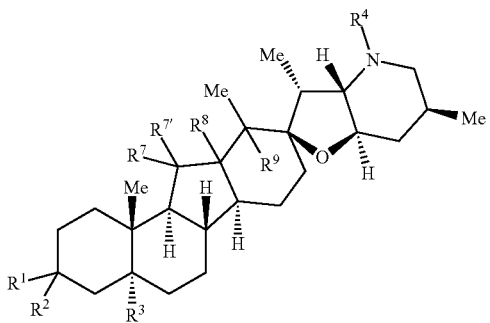

wherein $R^1$, $R^2$, $R^3$, $R^4$, $R^7$, $R^{7'}$, $R^8$, and $R^9$ are as defined below. Epimerically pure compounds contain less than about 20% by mass, less than about 15% by mass, less than about 10% by mass, less than about 5% by mass, or less than about 3% by mass of stereoisomeric compounds wherein the configuration of the stereogenic center that $R^3$ is bonded to is inverted relative to the compound.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M., *Protective Groups in Organic Synthesis*, 2$^{nd}$ ed.; Wiley: New York, 1991). In some cases, the functional group being protected and the protecting group are together referred to as one moiety. For example, the fragment shown below is sometimes referred to as a benzyl carbonate; i.e., the protected (underlined) O makes up part of the carbonate.

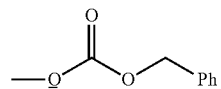

Similarly, the fragment shown below, in which the protected N makes up part of the carbamate, is referred to as a benzyl carbamate.

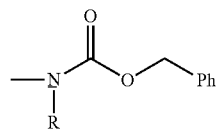

The term "sugar" as used herein refers to a natural or an unnatural monosaccharide, disaccharide or oligosaccharide comprising one or more pyranose or furanose rings. The sugar may be covalently bonded to the steroidal alkaloid of the present invention through an ether linkage or through an alkyl linkage. In certain embodiments the saccharide moiety may be covalently bonded to a steroidal alkaloid of the present invention at an anomeric center of a saccharide ring. Sugars may include, but are not limited to ribose, arabinose, xylose, lyxose, allose, altrose, glucose, mannose, gulose, idose, galactose, talose, glucose, and trehalose.

The term "sulfonamido" or "sulfonamide" as used herein includes a moiety having either of the following formulae:

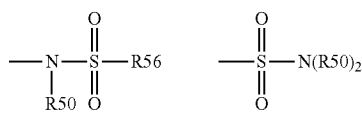

wherein R50 is defined above.

The terms "triflyl", "tosyl", "mesyl", and "nonaflyl" refer to trifluoromethanesulfonyl, p-toluenesulfonyl, methanesulfonyl, and nonafluorobutanesulfonyl groups, respectively. The terms "triflate", "tosylate", "mesylate", and "nonaflate" to trifluoromethanesulfonate ester, p-toluenesulfonate ester, methanesulfonate ester, and nonafluorobutanesulfonate ester functional groups and molecules that contain the groups, respectively.

The term "thioxo" refers to a carbonyl sulfur (═S).

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

As set out above, certain embodiments of the present compounds may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", *J. Pharm. Sci.* (1977) 66:1-19)

The pharmaceutically acceptable salts of the compounds of the present invention include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge, et al., supra)

Synthesis of Steroidal Alkaloid Compounds

The ring expanded steroidal alkaloid derivatives described above can be prepared directly from naturally occurring steroidal alkaloids or synthetic analogs thereof. In certain instances, the steroidal alkaloid starting materials can be cyclopamine or jervine. These steroidal alkaloids can be purchased commercially or extracted from *Veratrum Californicum*. Briefly, the process of the present invention comprises the steps of cyclopropanating suitable starting steroidal alkaloid derivatives followed by ring expansion rearrangement of the cyclopropyl derivatives. In some instances, it may be desirable to suitably protect or otherwise transform reactive functionalities present on the molecule prior to cyclopropanation. For example, an alcohol present at $R^1$ and a secondary nitrogen present on the fused furanopiperidine ring can both be protected prior to cyclopropanation. In certain embodiments, protecting groups that are efficiently added and removed from the alkaloid, yield intermediates in the synthetic process with improved handling properties and which allow for the efficient purification of the synthetic intermediates formed may be preferred.

Examples of oxygen protecting groups include, but are not limited to formate, acetate, chloroacetate, dichloroacetate, trichloroacetate, pivaloate, benzoates, alkyl carbonate, alkenyl carbonate, aryl carbonates, aralkyl carbonate (e.g., benzyl carbonate), 2,2,2-trichloroethyl carbonate, alkoxymethyl ether, aralkoxymethyl ether, alkylthiomethl ether, aralkylthio ether, arylthio ether, trialkylsilyl ether, alkylarylsilyl ether, benzyl ether, arylmethyl ether, and allyl ether.

Examples of nitrogen protecting groups include, but are not limited to formyl, chloroacetyl, trichloroacetyl, trifluoroacetyl, phenyl acetyl, benzoyls, benzamides, alkyl carbamates, aralkyl carbamates (e.g., benzyl carbamates), aryl carbamates, allyl, aralkyl, alkoxymethyl, aralkoxymethyl, N-2-cyanoethyl, diarylphosphinamides, dialkylphosphinamidates, diarylphosphinamidates, and trialkylsilyl.

Additional protecting groups that may be used in the methods of the present invention are described in Green, T. W.; Wuts, P. G., *Protective Groups in Organic Synthesis*, 3$^{rd}$ Edition, John Wiley & Sons, Inc. 1999.

A variety of cyclopropanating agents can be used to cyclopropanate the steroidal alkaloid. 1,1-haloalkylmetal complexes and reactive species referred to as carbenoids, are commonly used to cyclopropanate olefins. These reagents are typically made using a diiodoalkane or diazoalkane and a metal or organometalic species such as $Et_2Zn$, $ibu_3Al$, samarium, copper, rhodium, or palladium. In certain embodiments, $Et_2Zn$ and diiodomethane are used to generate the 1,1-haloalkylmetal species.

The reactivity and the ease of handling of the 1,1-haloalkylzinc complexes can be modified by the addition of certain reagents, such as acids. It is believed that the addition of an acid to the 1,1-haloalkylzinc species generates an alkyl zinc mixed salt. In the examples described below a biarylphosphoric acid is combined with diiodomethane and diethylzinc to generate a putative haloalkyl zinc phosphate cyclopropanating agent. A variety of phosphoric acids can be used to generate the putative haloalkylzinc phosphate.

Other known cyclopropanation methods such as those utilizing sulfur ylides to react with an olefin conjugated to a carbonyl to add a $CH_2$ or CH-alkyl or CH-aryl group, and metal-catalyzed decomposition of diazoalkyl and α-diazocarbonyl compounds, such as diazomethane and ethyl diazoacetate, can also be used: these methods readily provide cyclopropanes having alkyl, aryl, alkoxycarbonyl (—COOR), or acyl substituents. Additional cyclopropanating agents are described in Masalov et al., *Organic Letters* (2004) 6:2365-2368 and Hansen, et al., *Chem. Comm.* (2006) 4838-4840.

The cyclopropyl ring may be substituted or unsubstituted. In cases where the cyclopropyl ring is substituted, the groups attached to the methylene of the cyclopropane will be installed onto the D ring after rearrangement and ring expansion.

The cyclopropanation reactions may be conducted in an aprotic solvent. Suitable solvents include ethers, such as diethyl ether, 1,2-dimethoxyethane, diglyme, t-butyl methyl ether, tetrahydrofuran and the like; halogenated solvents, such as chloroform, dichloromethane, dichloroethane, and the like; aliphatic or aromatic hydrocarbon solvents, such as benzene, xylene, toluene, hexane, pentane and the like; esters and ketones, such as ethyl acetate, acetone, and 2-butanone; polar aprotic solvents, such as acetonitrile, dimethylsulfoxide, dimethylformamide, and the like; or combinations of two or more solvents. In a certain embodiments, dichloromethane is the solvent used for the cyclopropanation when a dialkyl zinc and diiodomethane is used.

In the examples described below, a solution containing the cyclopropanating agent is prepared by first adding a solution of a phosphoric acid to a solution of diethylzinc, followed by addition of diiodomethane to the reaction solution. The cyclopropanation substrate is then added to this solution. Alternatively, the cyclopropanation agent can be prepared in the presence of the cyclopropanation substrate by changing the order of addition of the reagents. In certain embodiments, the cyclopropanation reaction is conducted by first adding the phosphoric acid to a solution of dialkylzinc, followed by the addition of the cyclopropanation substrate, and finally the dihaloalkane is added. Using this method the cyclopropanating agent is generated under controlled conditions and immediately reacts with the cyclopropanation substrate.

Following synthesis of the cyclopropanated steroidal alkaloid core, the compound may be derivatized using a variety of functionalization reactions known in the art. Representative examples include palladium coupling reactions to alkenylhalides or aryl halides, oxidations, reductions, reactions with nucleophiles, reactions with electrophiles, pericyclic reactions, radical reactions, installation of protecting groups, removal of protecting groups, and the like.

In the presence of Lewis or Brønsted acids the cyclopropyl analogs undergo a rearrangement and ring expansion to afford steroidal alkaloid analogs in which the D ring has been expanded by one carbon.

The cyclopropanation and ring expansion can take place in a two-step one reaction vessel process or in a two-step two reaction vessel process. When the cyclopropanation and ring expansion are conducted in the same reaction vessel the acid used to initiate the ring expansion rearrangement is added after completion of the cyclopropanation reaction. Under certain conditions, the zinc salts that are generated in the course of cyclopropanating the steroidal alkaloid can themselves act as Lewis acids to catalyze the ring expansion rearrangement. The reactivity of the zinc salts generated after the cyclopropanation can be modified by the addition of acids to generate more active Lewis acids.

As described below in the examples section, the methanesulfonic acid is added to the cyclopropanation reaction vessel after completion of the cyclopropanation. Additional examples of suitable acids include, but are not limited to zinc salts, boron compounds, magnesium salts, titanium salts, indium salts, aluminum salts, tin salts, lanthanum salts, trifluoromethanesulfonic acid, diaryloxyphosporic acids, acetic acid, and hcl. In a certain embodiments of the invention the Lewis acid used is a zinc salt or $BF_3$.

These ring expanded analogs may be further functionalized using a variety of functionalization reactions known in the art. Representative examples include palladium coupling reactions to alkenylhalides or aryl halides, oxidations, reductions, reactions with nucleophiles, reactions with electrophiles, pericyclic reactions, radical reactions, installation of protecting groups, removal of protecting groups, and the like.

Pharmaceutical Compositions

The compounds disclosed herein may be formulated into composition suitable for administration, using one or more pharmaceutically acceptable carriers (additives) and/or diluents. The pharmaceutical compositions may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, capsules, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) pulmonarily, or (9) nasally.

Examples of suitable aqueous and nonaqueous carriers which may be employed in the pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents, dispersing agents, lubricants, and/or antioxidants. Prevention of the action of microorganisms upon the compounds disclosed herein may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Methods of preparing these formulations or compositions include the step of bringing into association a compound with the carrier and, optionally, one or more accessory ingredients. In general, the formulations are prepared by uniformly and intimately bringing into association a compound with liquid carriers, or finely divided solid carriers, or both, and then, if necessary, shaping the product.

When the compounds disclosed herein are administered as pharmaceuticals, to humans and animals, they can be given per se or as a pharmaceutical composition containing, for example, about 0.1 to 99%, or about 10 to 50%, or about 10 to 40%, or about 10 to 30%, or about 10 to 20%, or about 10 to 15% of active ingredient in combination with a pharmaceutically acceptable carrier.

Actual dosage levels of the active ingredients in the pharmaceutical compositions may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

In general, a suitable daily dose of a compound disclosed herein will be that amount of the compound which is the lowest dose effective to produce a therapeutic effect. Such an effective dose will generally depend upon the factors described above. Generally, oral, intravenous and subcutaneous doses of the compounds for a patient, when used for the indicated effects, will range from about 0.0001 to about 200 mg, or about 0.001 to about 100 mg, or about 0.01 to about 100 mg, or about 0.1 to about 100 mg per, or about 1 to about 50 mg per kilogram of body weight per day.

The compounds can be administered daily, every other day, three times a week, twice a week, weekly, or bi-weekly. The dosing schedule can include a "drug holiday," i.e., the drug can be administered for two weeks on, one week off, or three weeks on, one week off, or four weeks on, one week off, etc., or continuously, without a drug holiday. The compounds can be administered orally, intravenously, intraperitoneally, topically, transdermally, intramuscularly, subcutaneously, intranasally, sublingually, or by any other route.

The subject receiving this treatment is any animal in need, including primates, in particular humans, and other mammals such as equines, cattle, swine and sheep; and poultry and pets in general.

Methods of Treatment

Hedgehog signaling is essential in many stages of development, especially in formation of left-right symmetry. Loss or reduction of hedgehog signaling leads to multiple developmental deficits and malformations, one of the most striking of which is cyclopia.

Many tumors and proliferative conditions have been shown to depend on the hedgehog pathway. The growth of such cells and survival can be affected by treatment with the compounds disclosed herein. Recently, it has been reported that activating hedgehog pathway mutations occur in sporadic basal cell carcinoma (Xie, et al., *Nature* (1998) 391: 90-92) and primitive neuroectodermal tumors of the central nervous system (Reifenberger, et al., *Cancer Res* (1998) 58:1798-1803). Uncontrolled activation of the hedgehog pathway has also been shown in numerous cancer types such as GI tract cancers including pancreatic, esophageal, gastric cancer (Berman, et al., *Nature* (2003) 425:846-851, Thayer, et al., *Nature* (2003) 425:851-856) lung cancer (Watkins, et al., *Nature* (2003) 422:313-317, prostate cancer (Karhadkar, et al. *Nature* (2004) 431:707-712, Sheng, et al., *Molecular Cancer* (2004) 3:29-42, Fan, et al., *Endocrinology* (2004) 145:3961-3970), breast cancer (Kubo, et al., *Cancer Research* (2004) 64:6071-6074, Lewis, et al., *Journal of Mammary Gland Biology and Neoplasia* (2004) 2:165-181) and hepatocellular cancer (Sicklick, et al., ASCO conference (2005), Mohini, et al., AACR conference (2005)).

For example, small molecule inhibition of the hedgehog pathway has been shown to inhibit the growth of basal cell carcinoma (Williams, et al., *PNAS* (2003) 100:4616-4621), medulloblastoma (Berman, et al., *Science* (2002) 297:1559-1561), pancreatic cancer (Berman, et al., *Nature* (2003) 425:846-851), gastrointestinal cancers (Berman, et al., *Nature* (2003) 425:846-851, published PCT application WO 05/013800), esophageal cancer (Berman, et al., *Nature* (2003) 425:846-851), lung cancer (Watkins, et al., *Nature* (2003) 422:313-317), and prostate cancer (Karhadkar, et al., *Nature* (2004) 431:707-712).

In addition, it has been shown that many cancer types have uncontrolled activation of the hedgehog pathway, for example, breast cancer (Kubo, et al., *Cancer Research* (2004) 64:6071-6074), heptacellular cancer (Patil, et al., 96th Annual AACR conference, abstract #2942 (2005); Sicklick, et al., ASCO annual meeting, abstract #9610 (2005)), hematological malignancies (Watkins and Matsui, unpublished results), basal carcinoma (Bale & Yu, *Human Molec. Genet.* (2001) 10:757-762, Xie, et al., *Nature* (1998) 391:90-92), medulloblastoma (Pietsch, et al., *Cancer Res.* (1997) 57:2085-2088), and gastric cancer (Ma, et al., *Carcinogenesis*, May 19, 2005 (Epub) (2005)). In addition, investigators have found that small molecule inhibition of the hedgehog pathway has been shown to ameliorate the symptoms of psoriasis (Tas, et al., *Dermatology* (2004) 209:126-131). As shown in the Examples, the compounds disclosed herein have been shown to modulate the hedgehog pathway, and selected compounds have been shown to inhibit tumor growth. It is therefore believed that these compounds can be useful to treat a variety of hyperproliferative disorders, such as various cancers.

Proliferative disorders that can be treated using the methods disclosed herein include: lung cancer (including small cell lung cancer and non small cell lung cancer), other cancers of the pulmonary system, medulloblastoma and other brain cancers, pancreatic cancer, basal cell carcinoma, breast cancer, prostate cancer and other genitourinary cancers, gastrointestinal stromal tumor (GIST) and other cancers of the gastrointestinal tract, colon cancer, colorectal cancer, ovarian cancer, cancers of the hematopoietic system (including multiple myeloma, acute lymphocytic leukemia, acute myelocytic leukemia, chronic myelocytic leukemia, chronic lymphocytic leukemia, Hodgkin lymphoma, and non-Hodgkin lymphoma, and myelodysplastic syndrome), polycythemia Vera, Waldenstrom's macroglobulinemia, heavy chain disease, soft-tissue sarcomas, such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, squamous cell carcinoma, basal cell carcinoma, melanoma, and other skin cancers, adenocarcinoma, sweat gland carcinoma, sebaceous gland carcinoma, papillary carcinoma, papillary adenocarcinomas, stadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, bladder carcinoma, and other genitourinary cances, epithelial carcinoma, glioma, astrocytoma, medulloblastoma, craniopharyngioma, ependymoma, pinealoma, hemangioblastoma, acoustic neuroma, oligodendroglioma, meningioma, neuroblastoma, retinoblastoma, endometrial cancer, follicular lymphoma, diffuse large B-cell lymphoma, mantle cell lymphoma, hepatocellular carcinoma, thyroid cancer, gastric cancer, esophageal cancer, head and neck cancer, small cell cancers, essential thrombocythemia, agnogenic myeloid metaplasia, hypereosinophilic syndrome, systemic mastocytosis, familiar hypereosinophilia, chronic eosinophilic leukemia, thyroid cancer, neuroendocrine cancers, and carcinoid tumors. Additional disorders include Gorlin's syndrome and psoriasis The subject receiving this treatment is any animal in need, including primates, in particular humans, and other mammals such as equines, cattle, swine and sheep; and poultry and pets in general.

The hedgehog inhibitors disclosed herein can be combined with other cancer treatments. For example, they can be combined with surgical treatments; radiation; biotherapeutics (such as interferons, cytokines—e.g., Interferon α, Interferon γ, and tumor necrosis factor, hematopoietic growth factors, monoclonal serotherapy, vaccines and immunostimulants); antibodies (e.g., Avastin, Erbitux, Rituxan, and Bexxar); endocrine therapy (including peptide hormones, corticosteroids, estrogens, androgens and aromatase inhibitors); anti-estrogens (e.g., Tamoxifen, Raloxifene, and Megestrol); LHRH agonists (e.g., goscrclin and Leuprolide acetate); anti-androgens (e.g., flutamide and Bicalutamide); gene therapy; bone marrow transplantation; photodynamic therapies (e.g., vertoporfin (BPD-MA), Phthalocyanine, photosensitizer Pc4, and Demethoxy-hypocrellin A (2BA-2-DMHA)); and chemotherapeutics.

Examples of chemotherapeutics include gemcitabine, methotrexate, taxol, mercaptopurine, thioguanine, hydroxyurea, cytarabine, cyclophosphamide, ifosfamide, nitrosoureas, cisplatin, carboplatin, mitomycin, dacarbazine, procarbizine, etoposides, prednisolone, dexamethasone, cytarbine, campathecins, bleomycin, doxorubicin, idarubicin, daunorubicin, dactinomycin, plicamycin, mitoxantrone, asparaginase, vinblastine, vincristine, and vinorelbine. Additional agents include nitrogen mustards (e.g., cyclophosphamide, Ifosfamide, Trofosfamide, Chlorambucil, Estramustine, and Melphalan), nitrosoureas (e.g., carmustine (BCNU) and Lomustine (CCNU)), alkylsulphonates (e.g., busulfan and Treosulfan), triazenes (e.g., Dacarbazine and Temozolomide), platinum containing compounds (e.g., Cisplatin, Carboplatin, and oxaliplatin), vinca alkaloids (e.g, vincristine, Vinblastine, Vindesine, and Vinorelbine), taxoids (e.g, paclitaxel and Docetaxol), epipodophyllins (e.g, etoposide, Teniposide, Topotecan, 9-Aminocamptothecin, Camptoirinotecan, Crisnatol, Mytomycin C, and Mytomycin C), antimetabolites, DHFR inhibitors (e.g, methotrexate and Trimetrexate), IMP dehydrogenase Inhibitors (e.g, mycophenolic acid, Tiazofurin, Ribavirin, and EICAR), ribonucleotide reductase Inhibitors (e.g, hydroxyurea and Deferoxamine), uracil analogs (e.g, Fluorouracil, Floxuridine, Doxifluridine, Ratitrexed, and Capecitabine), cytosine analogs (e.g, cytarabine (ara C), Cytosine arabinoside, and Fludarabine), purine analogs (e.g, mercaptopurine and Thioguanine), Vitamin D3 analogs (e.g, EB 1089, CB 1093, and KH 1060), isoprenylation inhibitors (e.g, Lovastatin), dopaminergic neurotoxins (e.g, 1-methyl-4-phenylpyridinium ion), cell cycle inhibitors (e.g, staurosporine), actinomycins (e.g, Actinomycin D and Dactinomycin), bleomycins (e.g, bleomycin A2, Bleomycin B2, and Peplomycin), anthracyclines (e.g, daunorubicin, Doxorubicin (adriamycin), Idarubicin, Epirubicin, Pirarubicin, Zorubicin, and Mitoxantrone), MDR inhibitors (e.g, verapamil), $Ca^{2+}$ atpase inhibitors (e.g, thapsigargin), imatinib, thalidomide, lenalidomide, erlotinib, gefitinib, sorafenib, and sunitinib, and proteasome inhibitors, including bortezomib.

When the hedgehog inhibitors disclosed herein are administered in combination with other treatments, such as additional therapeutics or with radiation or surgery, the doses of each agent or therapy will in most instances be lower than the corresponding dose for single-agent therapy. Also, in general, the hedgehog inhibitors described herein and the second therapeutic agent do not have to be administered in the same pharmaceutical composition, and may, because of different physical and chemical characteristics, be administered by different routes. For example, one compound can be administered orally, while the second therapeutic is administered intravenously. The determination of the mode of administration and the advisability of administration, where possible, in the same pharmaceutical composition, is well within the knowledge of the skilled clinician. The initial administration can be made according to established protocols known in the art, and then, based upon the observed effects, the dosage, modes of administration and times of administration can be modified by the skilled clinician.

The hedgehog inhibitor and the second therapeutic agent and/or radiation may be administered concurrently (e.g., simultaneously, essentially simultaneously or within the same treatment protocol) or sequentially (i.e., one followed by the other, with an optional time interval in between), depending upon the nature of the proliferative disease, the condition of the patient, and the actual choice of second therapeutic agent and/or radiation to be administered.

If the hedgehog inhibitor, and the second therapeutic agent and/or radiation are not administered simultaneously or essentially simultaneously, then the optimum order of administration may be different for different conditions. Thus, in certain situations the hedgehog inhibitor may be administered first followed by the administration of the second therapeutic agent and/or radiation; and in other situations the second therapeutic agent and/or radiation may be administered first followed by the administration of a hedgehog inhibitor. This alternate administration may be repeated during a single treatment protocol. The determination of the order of administration, and the number of repetitions of administration of each therapeutic agent during a treatment protocol, is well within the knowledge of the skilled physician after evaluation of the disease being treated and the condition of the patient. For example, the second therapeutic agent and/or radiation may be administered first, especially if it is a cytotoxic agent, and then the treatment continued with the administration of a hedgehog inhibitor followed, where determined advantageous, by the administration of the second therapeutic agent and/or radiation, and so on until the treatment protocol is complete.

Exemplification

The invention now being generally described, it will be more readily understood by reference to the following examples, which are included merely for purposes of illustration of certain aspects and embodiments of the present invention, and are not intended to limit the invention.

EXAMPLE 1

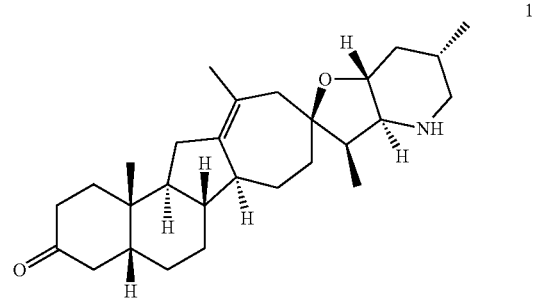

Step A

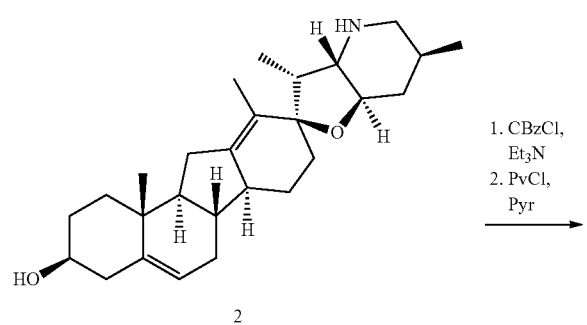

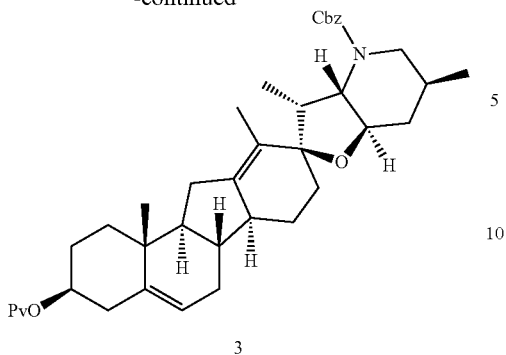

3

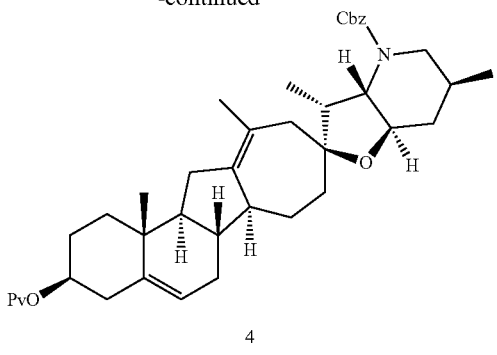

4

Recrystallized cyclopamine 2 (14.1 g, 34.0 mmol, 1 eq) is dissolved in anhydrous DCM (70 ml) and anhydrous meoh (29 ml). The clear solution is cooled, and triethylamine (10.4 g, 102.7 mmol, 3 eq) followed by benzyl chloroformate (6.20 g, 36.3 mmol, 1.1 eq) is added. After the addition is complete, the solution is stirred in the ice bath for 30 min. Three portions of benzyl chloroformate (3×0.35 g, 3.46 mmol, 0.03 eq) are added over the 3 h. The reaction is slowly quenched with water (71 ml), while maintaining the temperature below 20° C. The mixture is stirred for 15 min before the layers are settled and separated. The organic layer is dried over sodium sulfate and filtered. The combined filtrate is buffered with anhydrous pyridine (30 ml), concentrated, and solvent exchanged with additional anhydrous pyridine (43 ml) and concentrated.

The solution of the compound in pyridine (43 ml) is further diluted with additional anhydrous pyridine (85 ml). Trimethylacetyl chloride (8.3 g, 68.7 mmol, 2 eq) is added slowly to the reaction mixture, and the reaction is heated to 45° C. The reaction is stirred at 45° C. For 30 min. The reaction is cooled and quenched by the addition of anhydrous meoh (4.5 ml). The quenched reaction mixture is stirred at rt for 40 min and then diluted with toluene (97 ml) and is treated sequentially with water (35 ml) and a 10 wt % aqueous sodium carbonate solution (100 ml). After vigorous stirring, the layers are separated and the organic layer is washed twice with water (2×100 ml), dried over sodium sulfate, and filtered. The filter cake is rinsed with toluene (49 ml) and discarded. The combined filtrates are concentrated, and solvent exchanged with concentration to toluene (145 ml) and further concentrating to dryness. The product is recrystallized from toluene and heptane. The crystalline product is isolated by suction filtration, washed with cold heptane and dried to a constant weight to afford 15.1 g of the desired product.

Step B

Bis(2,6-dimethyphenyl)phosphate (10.65 g, 34.8 mmol, 3.1 eq) is dried by concentration from anhydrous DCM (42 ml) and held under a nitrogen atmosphere. The phosphate is then redissolved in anhydrous DCM (110 ml). In a separate flask, a solution of neat diethylzinc (4.17 g, 33.8 mmol, 3.0 eq) in anhydrous DCM (35 ml) is prepared and cooled to −25° C. The phosphate solution is slowly transferred to the vessel containing the diethylzinc solution over 1 h, maintaining the temperature at or below −10° C. The clear ethylzinc phosphate solution is warmed to 0° C. And stirred for 15 min. Diiodomethane (9.25 g, 34.5 mmoles, 3.0 eq) is slowly added to the ethylzinc phosphate solution, maintaining the reaction temperature between 0 and 5 ° C. After the addition is complete, the zinc carbenoid solution is stirred for an additional 20 min.

In a separate flask, compound 3 (7.20 g, 11.4 mmol, 1 eq) is dissolved in anhydrous DCM (36 ml) and transferred to the reaction flask. After the addition is complete, the ice bath is removed and the reaction mixture is allowed to warm to rt. After 6 h the contents of the flask are cooled to −53° C. A solution of methanesulfonic acid (3.38 g, 35.2 mmol, 3.1 eq) in anhydrous DCM (3 ml) is added, maintaining the reaction temperature below −45° C. After 10 min morpholine (20 g, 230 mmol, 20 eq) is added to the reaction mixture, maintaining the reaction temperature below −40° C. The reaction is allowed to warm to rt overnight. The morpholine salts are removed by filtration and the filter cake rinsed with DCM (22 ml). The combined filtrates are washed with 2N aqueous hydrochloric acid (2×140 ml), 5% aqueous sodium bicarbonate (140 ml), 5% aqueous sodium bicarbonate (70 ml) and 5% aqueous sodium bisulfite (70 ml), and brine (144 ml). The organic layer is dried over magnesium sulfate and filtered. Without going to dryness, the DCM solution is concentrated and solvent exchanged with methanol (280 ml). The suspension are chilled with an ice bath and stirred for 40 minutes. The solids are isolated by filtration, washed twice with cold methanol (2×25 ml), and dried to a constant weight to afford 5.94 g of the desired product.

Step C

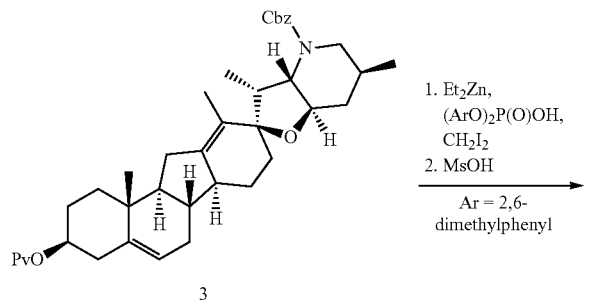

3

1. Et₂Zn, (ArO)₂P(O)OH, CH₂I₂
2. MsOH

Ar = 2,6-dimethylphenyl

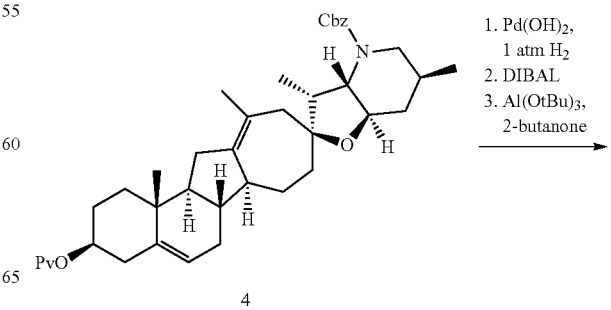

4

1. Pd(OH)₂, 1 atm H₂
2. DIBAL
3. Al(OtBu)₃, 2-butanone

-continued

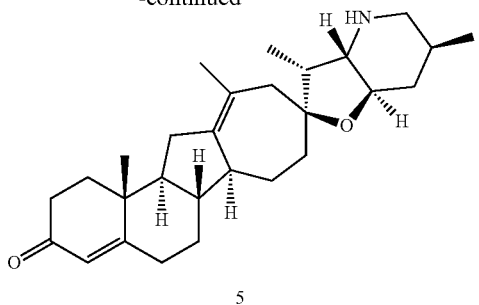

5

In a round bottom flask, compound 4 (11.67 g, 18.1 mmol, 1 eq) and 20% palladium hydroxide on wet carbon (2.40 g, 1.71 mmol, 0.09 eq) are placed under a nitrogen atmosphere and diluted with etoac (115 ml) and toluene (60 ml). The solution is degassed with nitrogen (3×) with evacuation/purge cycles, and the process is repeated for hydrogen. The suspension is vigorously stirred at rt for 1.5 h. The hydrogen atmosphere is replaced with nitrogen. Ethylenediamine (0.57 g, 9.5 mmol, 0.52 eq) is added to the reaction, and the resulting mixture stirred for 20 min. The solution is filtered under nitrogen, and the filtrate is washed with a 2% (wt/wt) aqueous solution of ethylenediamine (125 ml) then water (130 ml), and then dried over sodium sulfate. The drying agent is removed by filtration and the filtrate is concentrated to dryness under vacuum. The solids that remained are chased with toluene (2×55 ml) on the rotary evaporator and the resulting material used without further purification in the next step The material from the previous step is dissolved in anhydrous DCM (26 ml). The resulting clear solution is added to a 1 M solution of DIBAL in DCM (65 ml, 65 mmol, 3.6 eq) while maintaining the reaction temperature between −10 and −25° C. After 30 min the reaction is quenched with acetone (13 ml), maintaining the reaction temperature at or below 0° C. After stirring the quenched reaction mixture for 17 min, it is added in portions to a flask containing a cold, stirred solution of 20% (wt/wt) aqueous Rochelle salt (200 ml). The resulting gelatinous suspension is stirred at rt for 15 h. After stirring, the clean layers are separated and the aqueous layer back extracted with DCM (30 ml). The combined organic layers are washed with water (60 ml) and dried over sodium sulfate. The drying agent is removed by filtration and discarded. The filtrate is concentrated under vacuum and solvent exchanged to toluene (225 ml added in portions). The resulting solution is further concentrated to a suspension (50 ml) and diluted with heptane (115 ml). The resulting mixture is heated until turning homogeneous (92° C.). The solution is cooled slowly over 12 h to 15° C., and then held for 16 additional h. The crystalline product is isolated by suction filtration, washed with heptane (2×75 ml) and dried to a constant weight to afford 7.70 g of the desired product.

A round bottom flask is sequentially charged with the homo-allylic alcohol (7.50 g, 17.6 mmol, 1 eq), aluminum tri-tert-butoxide (6.10 g, 24.8 mmol, 1.4 eq), anhydrous toluene (115 ml), and 2-butanone (90 g, 1.24 mol, 7 eq). The suspension is heated under a nitrogen atmosphere to 75° C. For 16 h. The reaction temperature is then allowed to cool to 49° C. Aqueous 20% (w/w) potassium sodium tartrate solution (226 g) is added to the stirred suspension. The suspension is stirred at rt for 3.5 h. The layers are separated. The organic layer washed with aqueous 20% Rochelle salt (2×250 ml) and water (225 ml), then dried over sodium sulfate and filtered. The residue is rinsed with toluene (30 ml) and discarded. The combined organics are concentrated to dryness. Residual reaction solvents are removed from the material by concentrating from 2-propanol (250 ml added portion-wise) to a final solution mass of 44 g. Solvent exchange from 2-propanol to heptane (275 ml added portion-wise) to a final solution mass is 41 g fully precipitated the desired product. The suspension is diluted with of additional heptane (40 ml), stirred at rt for 1 h, and filtered. The product is washed with n-heptane (17 ml) and dried to afford 5.4 g of the desired product.

Step D

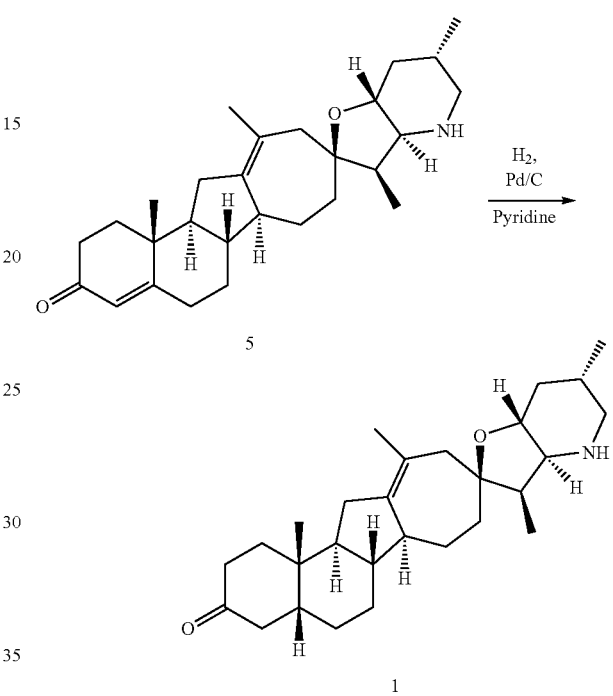

A round-bottom flask is charged with starting material (110 mg, 0.26 mmol, 1 eq) and 10% palladium on carbon (106 mg). The solids are suspended in pyridine (4 ml). The suspension is placed under hydrogen atmosphere (1 atm) and the mixture is stirred overnight at rt. The reaction mixture is filtered through Celite® and the filtrate concentrated in vacuo. The crude material is purified using silica gel flash chromatography (meoh/DCM 5:95) to afford 93 mg of the desired compound. ([M+H]=426.6 m/z).

EXAMPLE 2

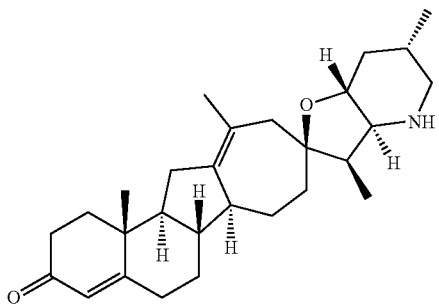

Step A

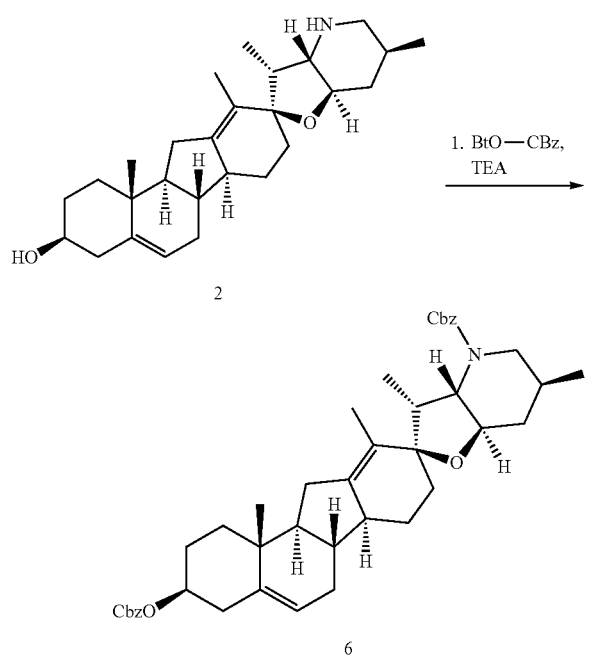

Cyclopamine 2 (5.02 g, 12.2 mmol, 1.0 eq) is dissolved in anhydrous pyridine (25 ml). DMAP (300 mg, 2.44 mmol, 0.2 eq.) And triethyl amine (5.5 ml, 39.1 mmol, 3.2 eq) are added, followed by bto-Cbz (10.5 g, 39.1 mmol, 3.2 eq) and heated at 40° C. For 2 h. The mixture is cooled to rt, treated with 30 ml water, heated to get a homogeneous solution and allowed to cool to room temp. The white precipitate that formed is collected by filtration, the filter cake is washed with portions of water (3×50 ml), and dried in air to afford 9.53 g of crude material which is crystallized from toluene/heptanes (1:9, 70 ml) to give 6.75 g of the desired product.

Step B

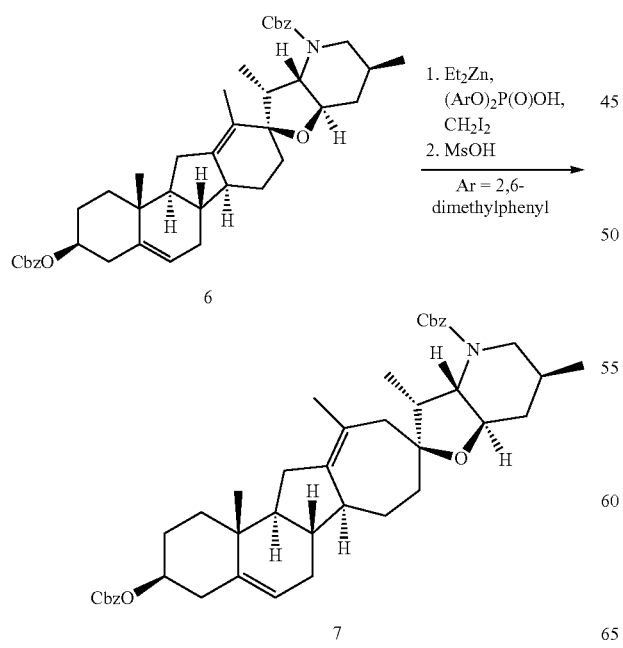

To a solution of diethyl zinc (572 mg, 482 µL, 4.63 mmol, 3.00 eq) in 5.0 ml DCM at −20° C. Is added a solution of bis-(2,6-Dimethylphenyl)phosphoric acid (1.42 g, 4.63 mmol, 3.00 eq) in DCM (15 ml) maintaining the reaction temperature below −8° C. The solution is aged for 15 min. At 0° C., neat diiodomethane (1.24 g, 374 µL, 3.00 eq) is added, aged for 15 min. At 0° C. Before adding a solution of (biscbzcyclopamine, 1.05 g, 1.54 mmol, 1.0 eq), in DCM (10 ml). The cooling bath is replaced by a water bath at rt and maintained at rt for 4.5 h. The mixture is cooled to −76° C. With a dry ice-acetone bath and treated drop wise with methanesulfonic acid DCM solution (0.6 ml 50% v/v solution 4.63 mmol, 3.0 eq) maintaining the reaction temperature below −74° C. The mixture is aged for 15-20 min. And quenched drop wise with morpholine (2.69 g, 2.70 ml, 20 eq) maintaining the reaction temperature below −65° C. The cooling bath is removed, the reaction mixture is stirred for 16-18 h., the white precipitate is filtered off, and the filtrate is successively washed with 2.0 M hcl (2×20 ml), satd. Sodium bicarbonate (2×20 ml), water (2×20 ml) and brine (20 ml). Dried over magnesium sulfate, concentrated in vacuo to dryness and the crude is purified by silica gel flash chromatography (hexanes/etoac 17:3→4:1) to afford 924 mg (1.33 mmol, 86%) of the desired product.

Step C

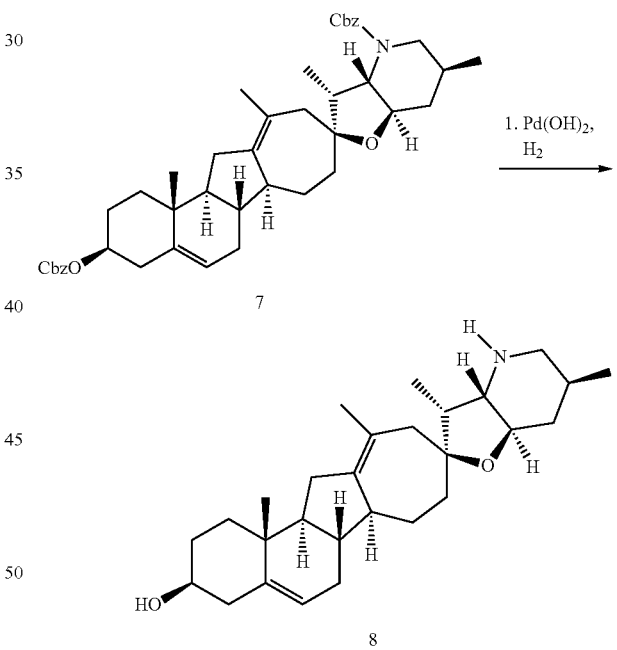

To a solution of compound 7 (4.05 g, 5.83 mmol, 1 eq) in a solution of etoac:toluene (2:1, 60 ml) is added of 20% palladium hydroxide on carbon (823 mg, 0.583 mmol, 0.1 eq.). The flask is evacuated and filled with hydrogen three times. The mixture is stirred under an atmosphere of hydrogen for 1 h. Neat ethylene diamine (0.38 ml) is added, stirred for 1 h., and the catalyst is filtered off. The filter cake is washed twice with etoac:toluene (2:1, 12 ml). The combined filtrates are washed with a 2% aqueous solution of ethylene diamine (3×20 ml), dried over sodium sulfate and concentrated in vacuo to give 2.46 g as a white crystalline solid.

Step D

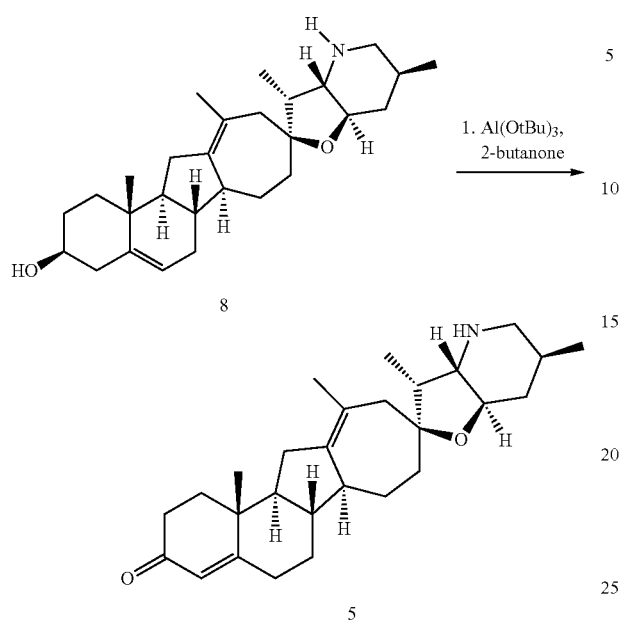

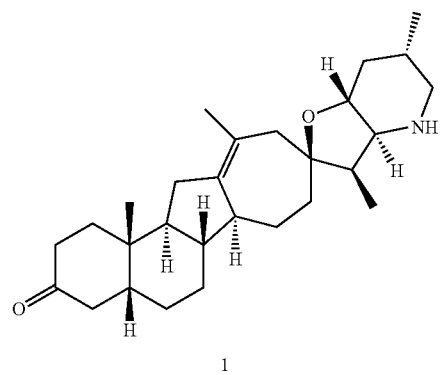

A round bottom flask is sequentially charged with the homo-allylic alcohol 8 (7.50 g, 17.6 mmol, 1 eq), aluminum tri-tert-butoxide (6.10 g, 24.8 mmol, 1.4 eq), anhydrous toluene (115 ml), and 2-butanone (90 g, 1.24 mol, 7 eq). The suspension is heated under a nitrogen atmosphere to 75° C. For 16 h. The reaction temperature is then allowed to cool to 49° C. Aqueous 20% (w/w) potassium sodium tartrate solution (226 g) is added to the stirred suspension. The suspension is stirred at rt for 3.5 h. The layers are separated. The organic layer washed with aqueous 20% Rochelle's salt (2×250 ml) and water (225 ml), then dried over sodium sulfate and filtered. The residue is rinsed with toluene (30 ml) and discarded. The combined organics are concentrated to dryness. Residual reaction solvents are removed from the material by concentrating from 2-propanol (250 ml added portion-wise) to a final solution mass of 44 g. Solvent exchange from 2-propanol to n-heptane (275 ml added portion-wise) to a final solution mass of 41 g fully precipitated the desired product. The suspension is diluted with of additional n-heptane (40 ml), stirred at rt for 1 h, and filtered. The product is washed with n-heptane (17 ml) and dried to afford 5.4 g of the desired product.

Step E

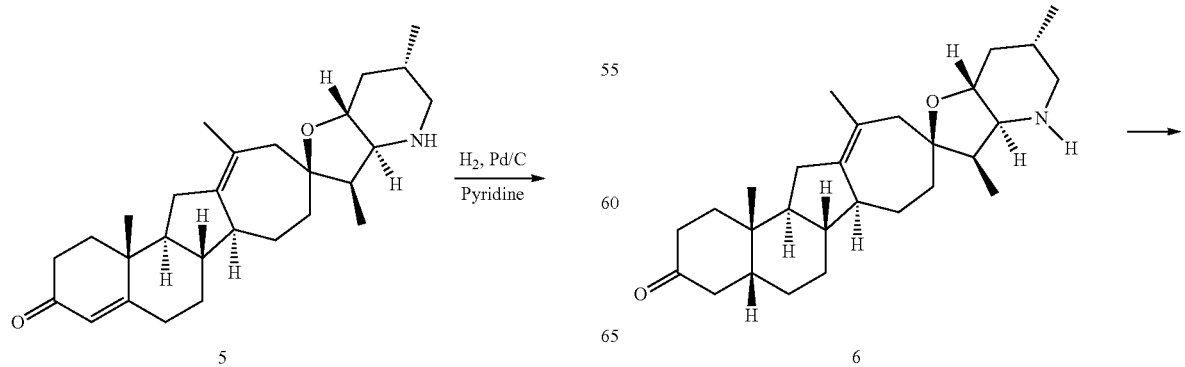

A round-bottom flask is charged with starting material (110 mg, 0.26 mmol, 1 eq) and 10% palladium on carbon (106 mg). The solids are suspended in pyridine (4 ml). The suspension is placed under hydrogen atmosphere (1 atm) and the mixture is stirred overnight at rt. The reaction mixture is filtered through Celite® and the filtrate concentrated in vacuo. The crude material is purified using silica gel flash chromatography (meoh/DCM 5:95) to afford 93 mg of the desired compound. ([M+H]=426.6 m/z).

EXAMPLE 3

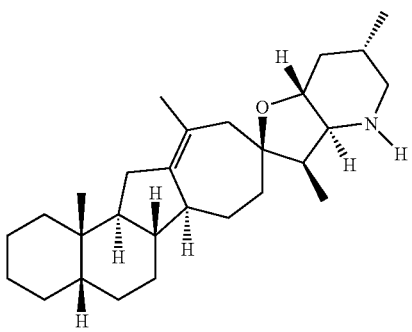

-continued

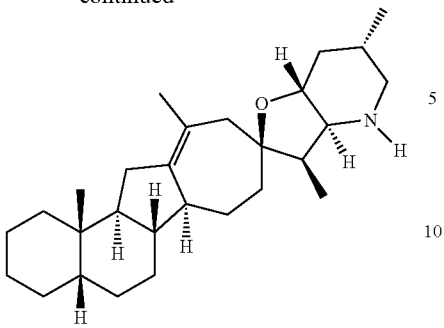

9

In a seal tube, ketone 6 (85 mg, 0.199 mmol, 1 equiv.) Was charged and triethyleneglycol (2 ml) was added followed by hydrazine monohydrate (500 mg, 10 mmol, 50 equiv.) And potassium carbonate (138 mg, 1 mmol, 5 equiv.). The tube was sealed and the reaction was heated at 150° C. For 16 h. The reaction was cooled to rt and water was added. The residue was extracted with chloroform (3×). The combined organic layers are washed with water, dried over $Na_2SO_4$, and concentrated to dryness. The colorless oil was purified using silica gel flash chromatography (DCM/meoh 96:4). The purified fractions are pooled and concentrated to dryness. The resulting oil was dissolved in MTBE and washed with water (2×), 2N naoh, and then brine. The combined organic layers are dried over $Na_2SO_4$, filtered and evaporated to afford 64 mg of the desired material as a white foam. ([M+H]=412.7 m/z).

EXAMPLE 4

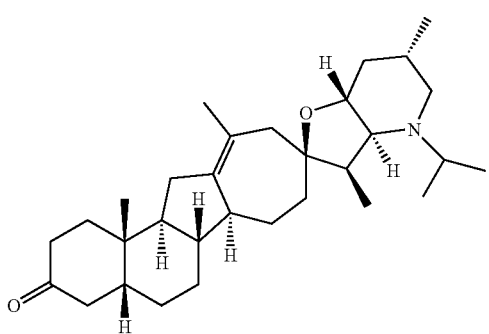

10

-continued

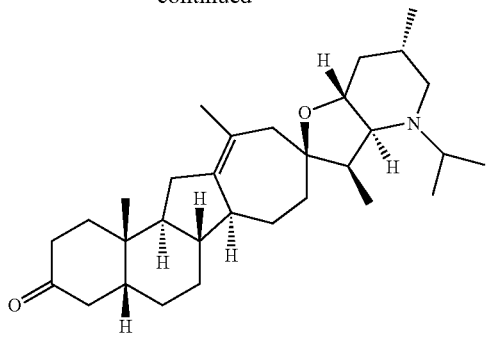

10

A sealed tube was charged with compound 5 (223 mg, 0.52 mmol, 1 eq) and DMF (1 ml). 2-Bromopropane (1.3 g, 10.5 mmol, 20 eq) and $Na_2CO_3$ (73 mg, 0.68 mmol, 1.3 eq) were added and the flask was sealed and heated to 50° C. The mixture was stirred for 16 h at which point ~70% conversion was observed. Additional (0.26 g, 2.12 mmol, 4 eq) was added. The reaction was stirred for 2 h and additional 2-bromopropane (0.13 g, 1.1 mmol, 2 eq) was added. The reaction was stirred for another 1 h. The reaction was cooled to rt and water was added. The residue was extracted with MTBE (3×). The organic layers were combined washed with brine, dried over $Na_2SO_4$, filtered, and concentrated to dryness. The white foam was purified using silica gel flash chromatography (DCM/meoh 99:1) to give 206 mg of the N-isopropyl derivative as a white foam.

The N-isopropyl derivative (205 mg, 0.44 mmol, 1 eq) was dissolved in of 4-methoxypyridine (1.5 ml). The flask was placed under inert atmosphere and Pd/C 10% (wet, Aldrich Degussa type E101, 40 mg) was added. The flask was sealed and purged three times with hydrogen and left 16 h under 1 atm of hydrogen. Celite® was added to the reaction mixture. The mixture was filtered through a small pad of Celite® and washed with etoac. The organic layer was washed with 1N hcl aq. (2×) then with water. The organic layer was dried over $Na_2SO_4$, filtered through cotton and evaporated to give 34 mg of crude. The aqueous layer was neutralized with 2N KOH and extracted with DCM (3×). The combined organic layers were washed with water, dried over $Na_2SO_4$, filtered through cotton and combined with the initial 34 mg of crude. The crude material was purified using silica gel flash chromatography hexane/etoac (6:4) to afford 80 mg of desired product. ([M+H]=468.7 m/z).

EXAMPLE 5

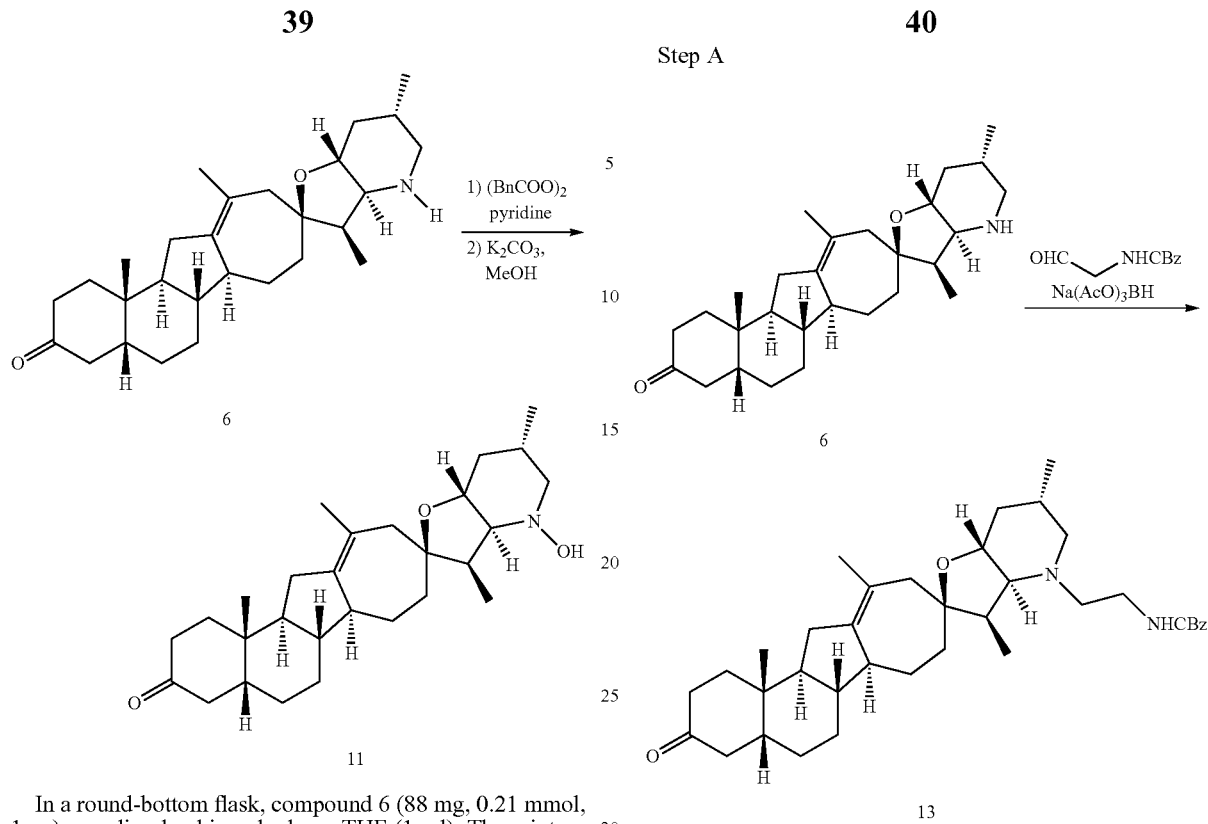

In a round-bottom flask, compound 6 (88 mg, 0.21 mmol, 1 eq) was dissolved in anhydrous THF (1 ml). The mixture was cooled to 0° C. Pyridine (84 µL, 1 mmol, 5 eq) and benzoylperoxide (150 mg, 0.62 mmol, 3 eq) were added successively. The homogeneous mixture was gradually warmed to rt over 2 h and stirred overnight at rt. The reaction was quenched by adding saturated nahco₃. The residue was extracted with MTBE. The combined organic layers were washed with water, dried over Na₂SO₄, filtered and concentrated under reduced pressure. The crude was purified using silica gel flash chromatography (hexane/etoac (9:1 to 4:1)) to give the N—O derivative product (60 mg, 0.11 mmol) as a white foam. This foam was dissolved in 2 ml of meoh followed by 2N aqueous KOH (0.4 ml). The reaction mixture was stirred for 1 h. Most of the meoh was evaporated under a stream of nitrogen and 1N hcl (500 µL) was added. The material was extracted with DCM (3×). The combined organic layers were washed with water, dried over Na₂SO₄, filtered and concentrated under reduced pressure. The crude was purified using silica gel flash chromatography (hexanes/etoac (from 88:12→1:1)) to yield 11 mg of the desired product. ([M+H]=442.5 m/z).

EXAMPLE 6

In a round bottom flask, compound 6 (89 mg, 0.209 mmol, 1 eq) and N-(benzyloxycarbonyl)-aminoacetaldehyde (148 mg, 0.85 mmol, 4 eq) were dissolved in DCM (2 ml). Sodium triacetoxyborohydride (177 mg, 0.85 mmol, 4 eq) was added and the reaction was stirred for 3 h at rt. The mixture was poured in saturated aqueous nahco₃ solution and the residue was extracted with DCM (3×). The combined organic layers were washed with water, dried over Na₂SO₄, filtered through cotton and evaporated to give a foamy solid (247 mg). The crude was dissolved in etoac (2 ml) and treated with of 4M hcl (156 µL). After 30 min a white precipitate slowly formed. The resulting slurry was stirred for 15 min. Filtration gave 120 mg of white solid. The material was dissolved in etoac and treated with a saturated aqueous nahco₃ solution. The organic layer was collect and the aqueous layer and was extracted with etoac (2×). The combined organic layers were washed with brine, dried over Na₂SO₄. Filtration and evaporation gave the desired intermediate. This material was used in the next step without purification.

Step B

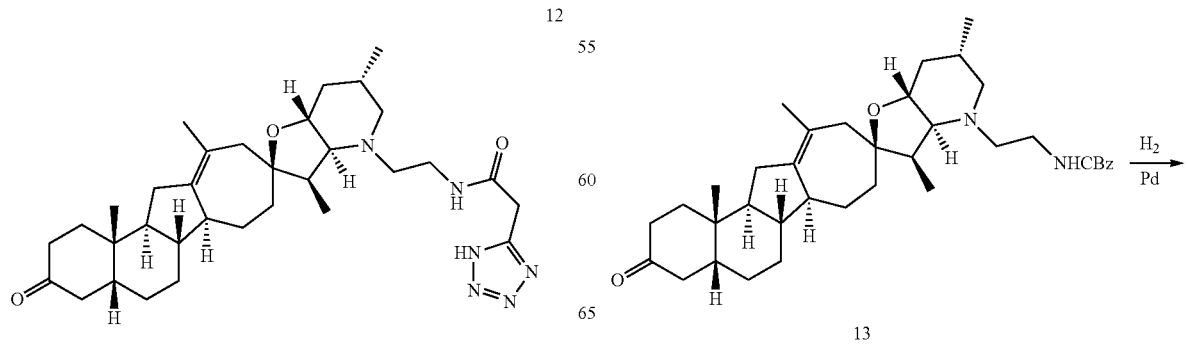

-continued

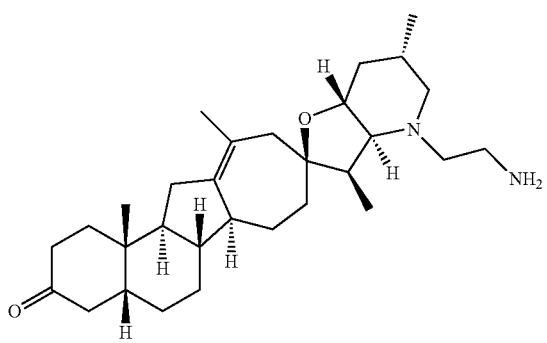

14

All of the material from Step A was dissolved in etoac (3 ml) and treated with of Pd/C 10% (30 mg, wet, Aldrich Degussa type E101). The flask was sealed and purged three times with hydrogen and left overnight under 1 atm of hydrogen. After 16 h, the mixture was filtered through a small pad of Celite® and washed with etoac to afford 52 mg of the amine as a white foam.

Step C

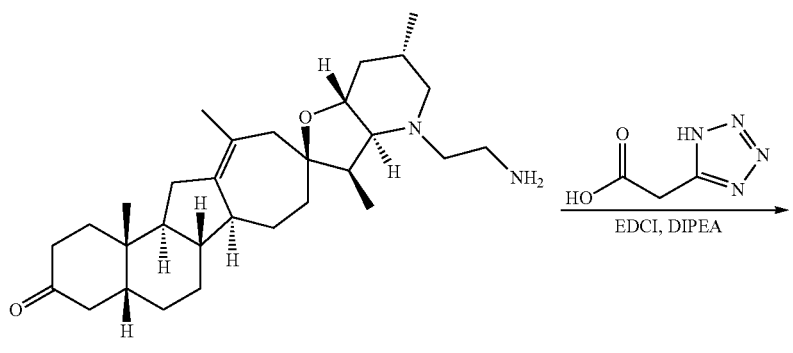

A round-bottom flask containing the amine 14 (52 mg, 0.11 mmol, 1 eq) was charged with the 1H-tetrazole-5-acetic acid (21 mg, 0.166 mmol, 1.5 eq), DCM (2 ml), edcl (42 mg, 0.22 mmol, 2 eq) and N,N-diisopropylethylamine (57 mg, 0.44 mmol, 4 eq) The resulting yellow solution was stirred at rt for 4 h. The reaction was quenched by the addition of saturated aqueous nahco₃ solution and the residue was extracted with DCM (3×). The combined organic layers were dried over $Na_2SO_4$, filtered through cotton and evaporated to give 62 mg of off-white solid. This material was purified using silica gel flash chromatography (meoh/DCM 5:95→10:90) to afford 31 mg of the desired product. ([M+H]=579.7 m/z).

EXAMPLE 7

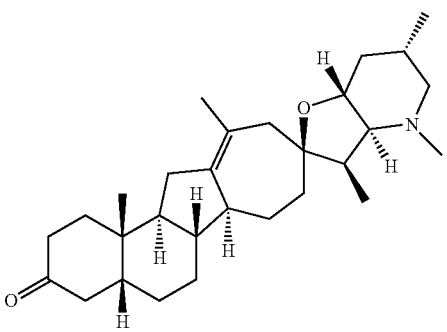

15

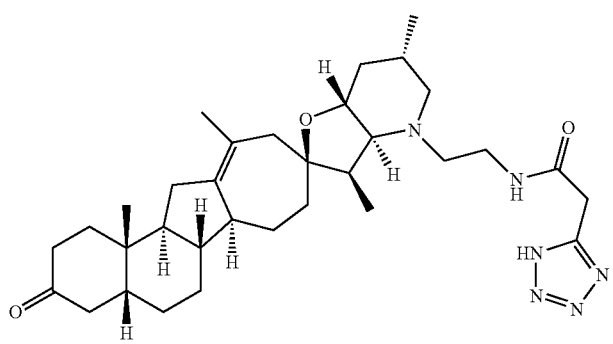

12

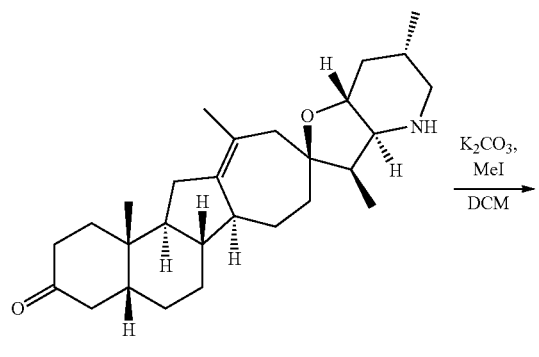

6

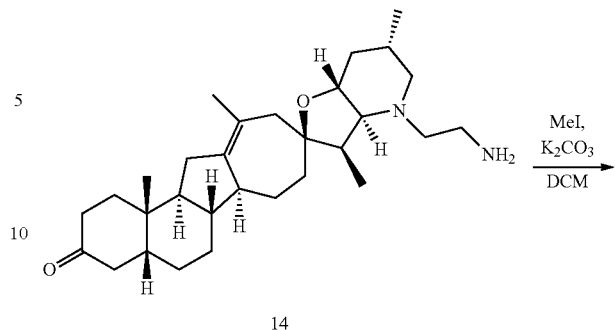

14

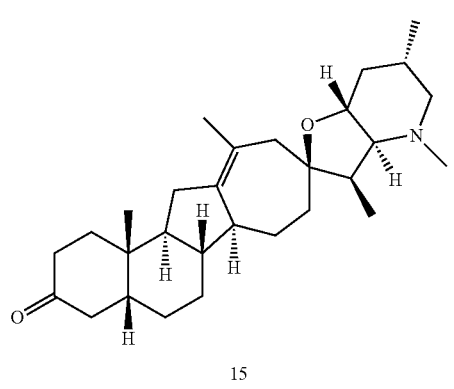

15

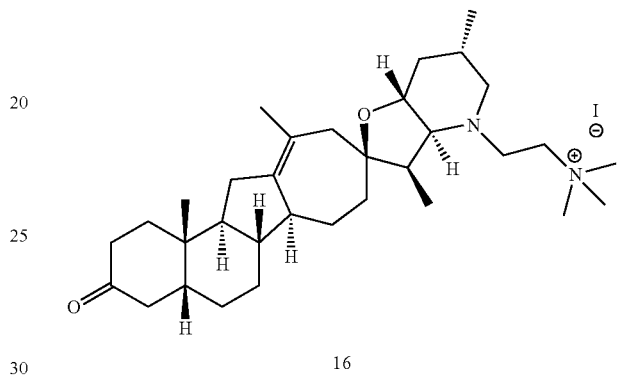

16

A round-bottom flask was charged with starting material (47 mg, 0.110 mmol, 1 eq) and potassium carbonate (150 mg, 1.09 mmol, 10 eq). The solids were suspended in 2 ml of DCM. Iodomethane (14 µL, 0.22 mmol, 2 eq) was added and the mixture was stirred for 2 at rt. TLC (DCM/meoh 95:5) indicate >90% completion. Iodomethane (14 µL, 0.22 mmol, 2 eq) was added to the reaction mixture, which was stirred for 2 h. The reaction mixture was added water. The phases were separated and the organics were dried and concentrated to dryness. The residue was purified using silica gel flash chromatography (DCM/meoh 100:0→98:2) afford 34 mg of the desired product ([M+H]=440.5 m/z).

EXAMPLE 8

A round-bottom flask was charged with starting material (59 mg, 0.126 mmol, 1 eq) and potassium carbonate (350 mg, 2.5 mmol, 20 eq). The solids were suspended in 3 ml of DCM. The reaction was charged with iodomethane (80 µL, 1.29 mmol, 10 eq) and the mixture was stirred overnight at rt. The reaction mixture was charged with water. The organic phase was separated and the aqueous layer was back extracted with DCM. The combined organic layers were dried and concentrated to dryness. The residue was purified using silica gel flash chromatography. DCM/meoh (95:5→90:10) to afford 52 mg of the desired product. ([M+H]=639.5 m/z).

EXAMPLE 9

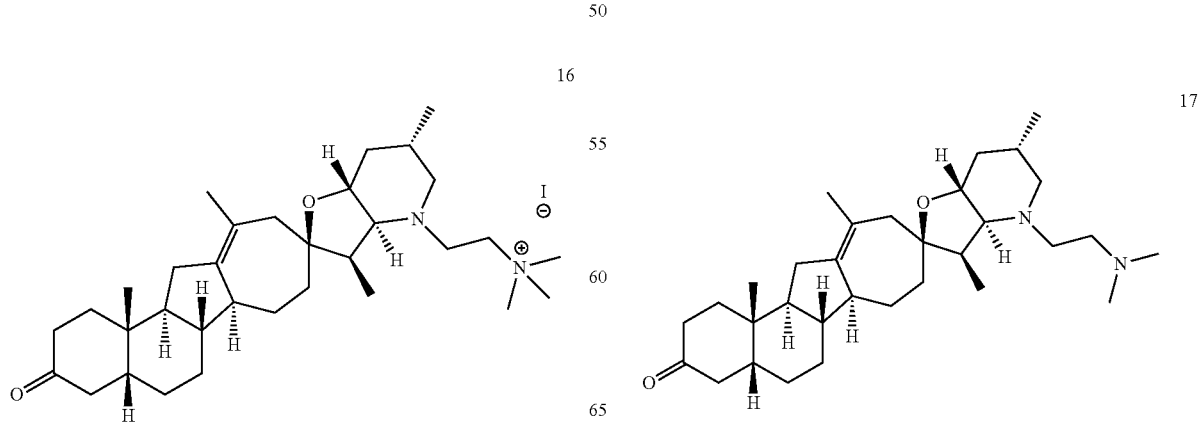

16

17

Step A

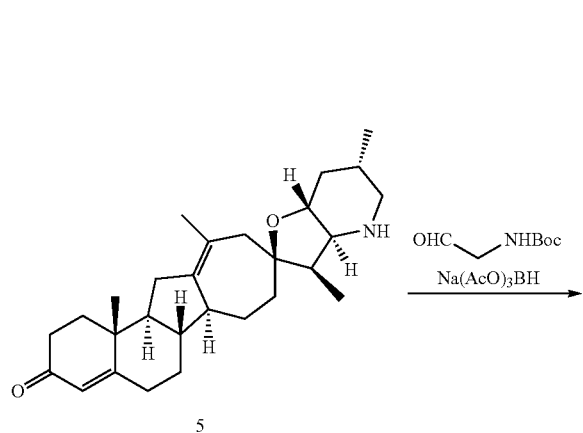

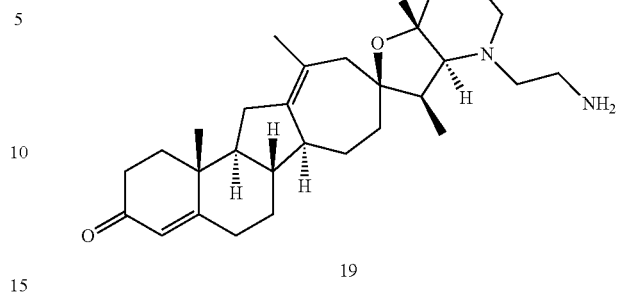

In a round bottom flask, compound 5 (50 mg, 0.12 mmol, 1 eq) and N-(t-butoxycarbonyl)-aminoacetaldehyde (6 mg, 0.38 mmol, 3.1 eq) were dissolved in DCM (2 ml). Sodium triacetoxyborohydride (8 mg, 0.38 mmol, 3.1 eq) was added and the reaction was stirred for 2 h at rt. The mixture was poured in saturated aqueous nahco₃ solution and the residue was extracted with DCM (3×). The combined organic layers were washed with water, dried over Na₂SO₄, filtered through cotton and evaporated to give a foamy solid (95 mg). The crude material was purified using silica gel flash chromatography (etoac/Hexanes 1:1) to yield 55 mg of compound 18.

Step B

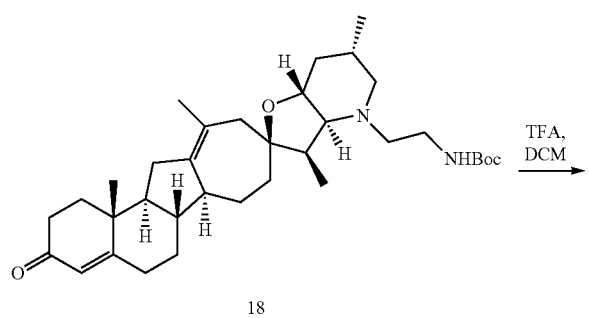

A round-bottom flask was charged with starting material 18 (800 mg, 1.4 mmol, 1 eq). The solid was dissolved in a solution of DCM and TFA (10 ml, 1:1). The solution was stirred for 45 min at rt. The reaction was partitioned between a solution of 10% sodium carbonate and DCM. The organic was separated and washed with 10% sodium carbonate. The organic phase was concentrated to dryness. The residue was used without further purification for the next step.

Step C

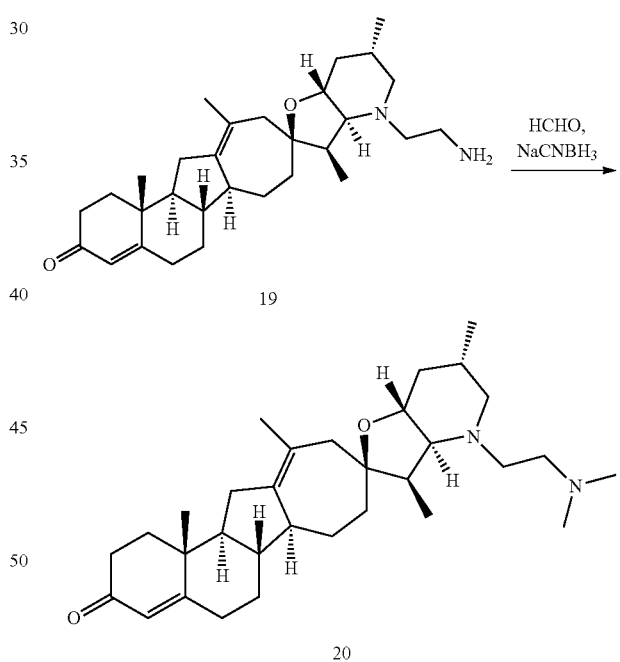

A round-bottom flask was charged with starting material (300 mg, 0.64 mmol, 1 eq) was dissolved in THF/ACN (1:1, 4 ml). The reaction was charged 37% formaldehyde in water (240 μL, 3.22 mmol, 5 eq) and sodium cyanoborohydride (64 mg, 1 mmol, 1.6 eq). The mixture was stirred for 30 min at rt. The reaction was then partitioned between a solution a saturated aqueous solution of sodium bicarbonate and DCM. The organic was separated, dried and concentrated to dryness. The crude material was purified using silica gel flash chromatography (meoh/DCM 5:95→10:90) to give the desired material.

Step D

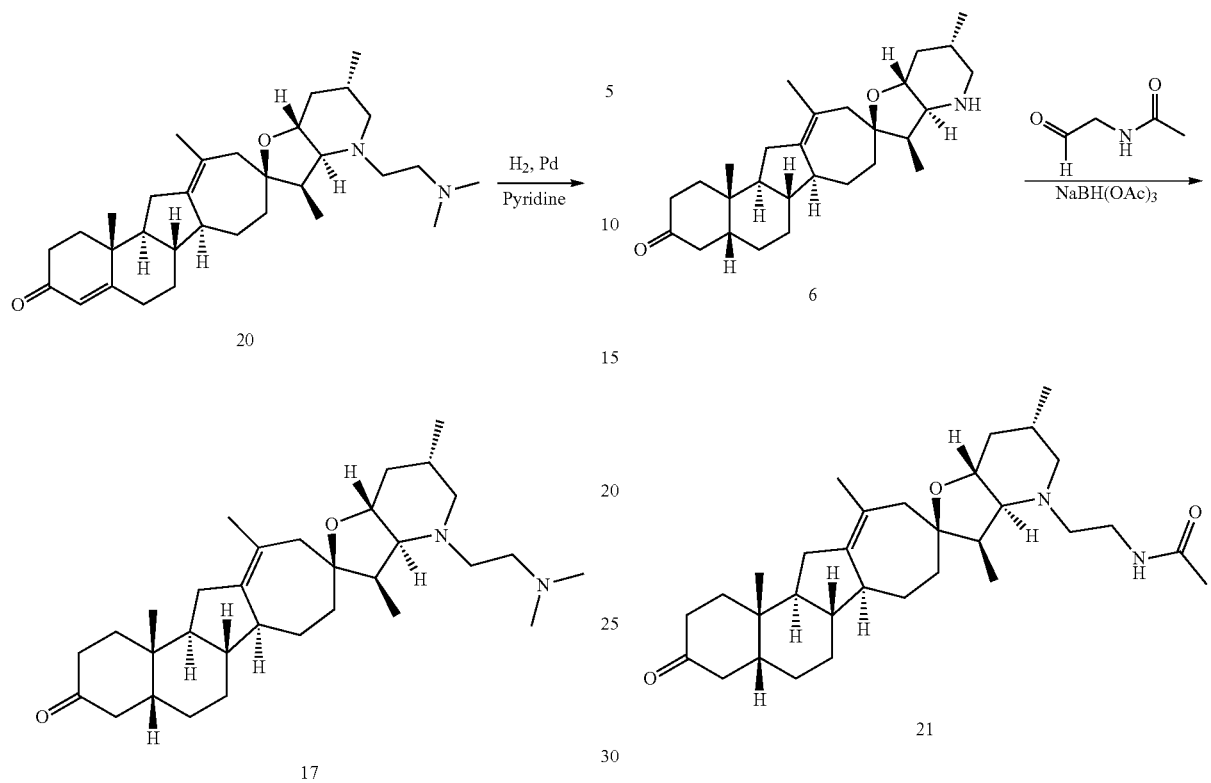

A round-bottom flask was charged with starting material 20 (30 mg, 0.06 mmol, 1 eq) and 10% palladium on carbon (30 mg). The solids were suspended in pyridine (2 ml). The suspension was placed under hydrogen atmosphere and the mixture was stirred overnight at rt. The reaction mixture was filtered on Celite® and the filtrate concentrated to dryness. The crude material was purified using silica gel flash chromatography (meoh/DCM 5:95→10:90) to give the desired material. ([M+H]=497.7 m/z).

EXAMPLE 10

A round-bottom flask was charged with starting material (85 mg, 0.20 mmol, 1 eq) was dissolved in DCM (4 ml). The reaction was charged with N-(2-oxoethyl)acetamide (80 mg, 0.70 mmol, 3.5 eq) and sodium triacetoxyborohydride (170 mg, 0.80, 4 eq). The mixture was stirred for 1 hour at rt. The reaction was partitioned between a solution a saturated aqueous solution of sodium bicarbonate and DCM. The organic was separated, dried and concentrated to dryness. The crude material was purified using silica gel flash chromatography (meoh/DCM 5:95) to give the desired material. ([M+H]=511.7 m/z).

EXAMPLE 11

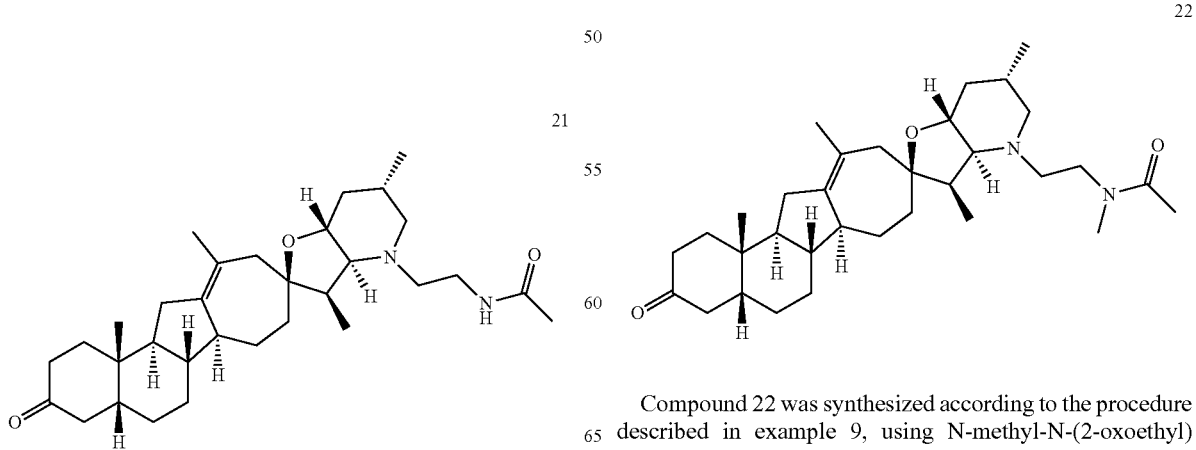

Compound 22 was synthesized according to the procedure described in example 9, using N-methyl-N-(2-oxoethyl)acetamide in place of N-(2-oxoethyl)acetamide. ([M+H]=525.7 m/z).

EXAMPLE 12

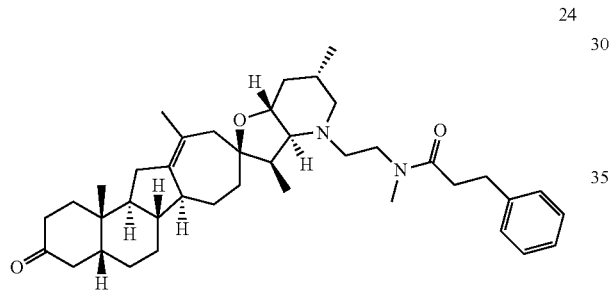

23

Compound 23 was synthesized according to the procedure described in example 10, using N-(2-oxoethyl)-3-phenyl-propanamide in place of N-(2-oxoethyl)acetamide. ([M+H]=601.8 m/z).

EXAMPLE 13

24

Compound 23 was synthesized according to the procedure described in example 10, using N-methyl-N-(2-oxoethyl)-3-phenylpropanamide in place of N-(2-oxoethyl)acetamide. ([M+H] 615.9 m/z)

EXAMPLE 14

25

Step A

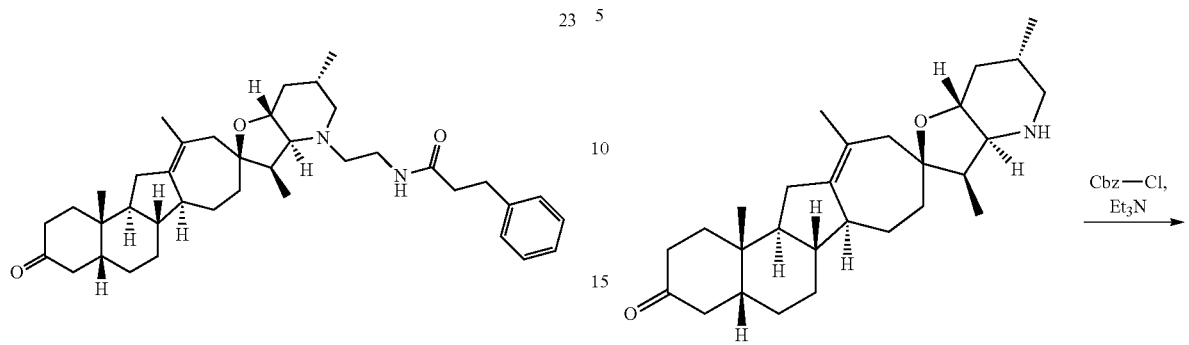

6

26

A round-bottom flask was charged with compound 6 (4.23 g, 9.94 mmol, 1 eq) and THF (60 ml). Triethylamine (6.92 ml, 49.7 mmol, 5.0 eq) and benzyl chloroformate (1.54 ml, 10.93 mmol, 1.1 eq) were added and the mixture was stirred for 1 hour at rt. The reaction mixture was partitioned between saturated aqueous bicarbonate (100 ml) and etoac (100 ml). The phases were separated and the organics were dried ($Na_2SO_4$) and concentrated to dryness. The crude material was purified using silica gel flash chromatography (etoac/Hexanes 2:98→14:86) to give 3.75 g of material.

Step B

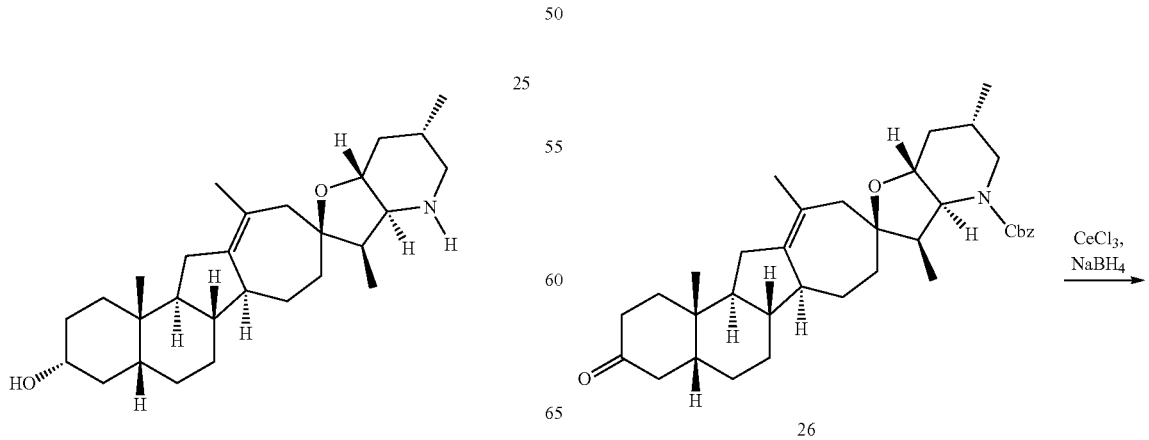

26

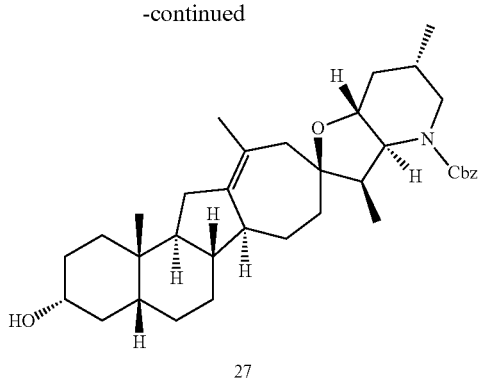

27

A meoh solution (10 ml) of cerium trichloride heptahydrate (260 mg, 0.69 mmol, 1.3 eq.) At 0° C. Was treated with sodium borohydride (24 mg, 0.65 mmol, 1.2 eq), stirred for 15 min, and then cooled to −78° C. A THF solution (10 ml) of ketone 26 (300 mg, 0.54 mmol, 1 eq) was added, and the mixture was stirred for 1 h and then warmed to rt. Water (50 ml) and etoac (50 ml) were added, mixed, and the layers split. The organic layer was collected, washed with brine (30 ml), dried over sodium sulfate, and concentrated to a white residue. The crude product was purified by silica gel flash chromatography (ether/hexanes 2:3→1:1) to give 235 mg of 3-beta alcohol 27.

Step C

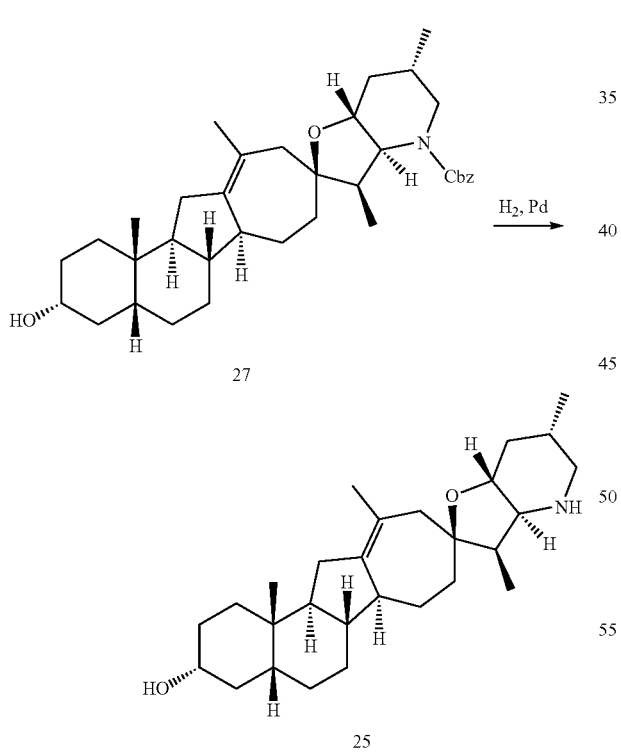

Compound 27 (235 mg, 0.42 mmol, 1 eq) was dissolved in etoac (7 ml) in a flask with stir bar and rubber septum. The solution was sparged with nitrogen, and Pd/C 10% (wet, Aldrich Degussa type E101, 50 mg) was added. This mixture was sparged with nitrogen and then hydrogen gas and stirred at rt for 3 h. The mixture was then sparged with nitrogen, filtered through a 0.45 μm polyethylene membrane and concentrated to a clear oil. The oil was purified by silica gel flash chromatography (NH₄OH(aq)/meoh/DCM 0.5:2:97.5→0.5:6:93.5) to give 130 mg of compound 25 as a white powder. ([M+H]=427.4 m/z)

EXAMPLE 15

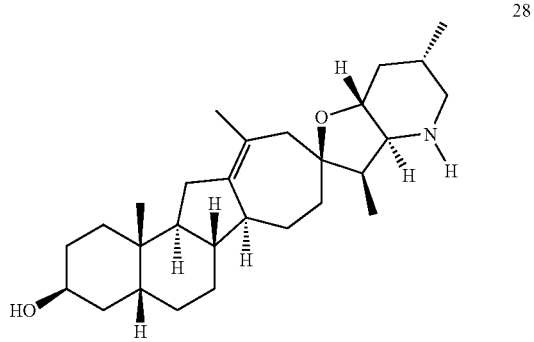

Step A

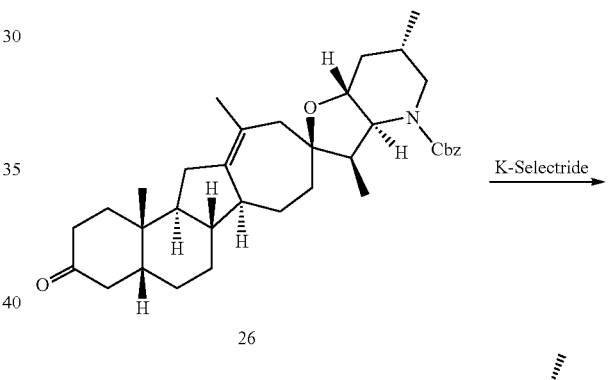

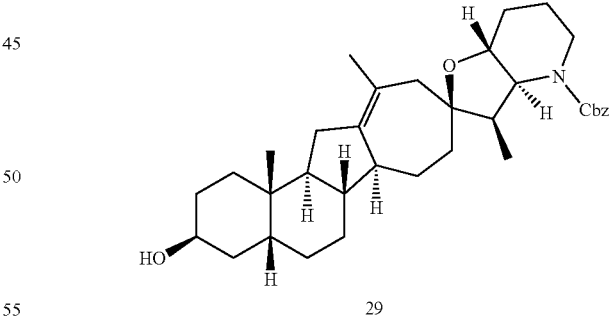

A THF solution (10 ml) of ketone 26 (300 mg, 0.54 mmol, 1 eq) at −78° C. Was treated with K-Selectride® (Potassium tri-sec-butylborohydride) (0.58 ml, 0.58 mmol, 1.1 eq) and stirred for 60 min. Methanol (1 ml) was added and the solution warmed to rt. Water (50 ml) and etoac (50 ml) were added, mixed, and the layers split. The organic layer was washed with brine (30 ml), dried over sodium sulfate, and concentrated to a white residue. The crude product was purified by silica gel flash chromatography (Ether/Hexanes 2:3→1:14) to give 170 mg of pure 3-alpha alcohol 29.

Step B

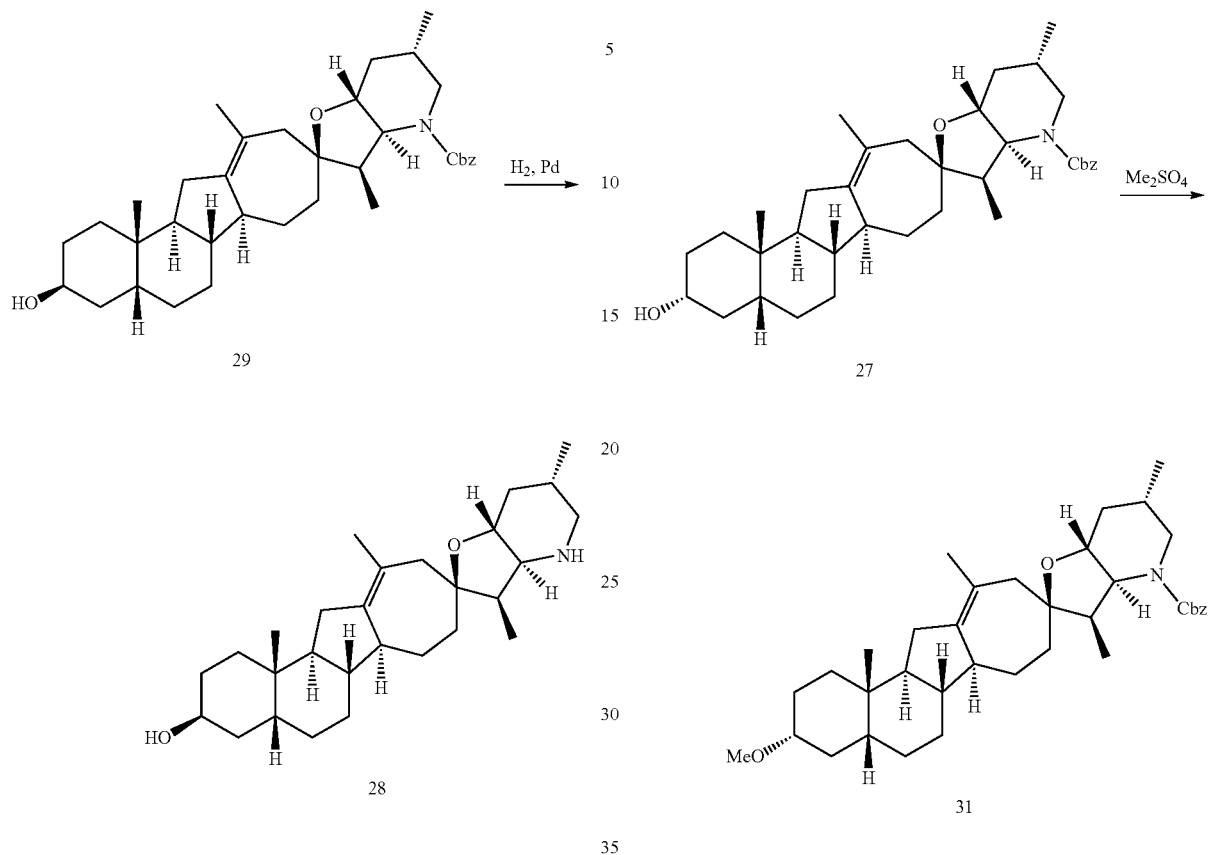

Step A

Compound 29 (170 mg, 0.30 mmol, 1 eq) was dissolved in etoac (5 ml) in a flask with stir bar and rubber septum. The solution was sparged with nitrogen, and Pd/C 10% (wet, Aldrich Degussa type E101, 35 mg) was added. This mixture was sparged with nitrogen and then hydrogen gas and stirred at rt for 3 h. The mixture was then sparged with nitrogen, filtered through a 0.45 μm polyethylene membrane and concentrated to a clear oil. The oil was purified by silica gel flash chromatography (NH$_4$OH(aq)/meoh/DCM 0.5:2:97.5→0.5:6:93.5) to afford 76 mg of compound 28 as a white powder ([M+H]=427.4 m/z).

EXAMPLE 16

Compound 27 (100 mg, 0.18 mmol, 1 eq) with benzyltriethylammonium chloride (8 mg, 0.36 mmol, 0.2 eq) was dissolved in DCM (5 ml) and stirred vigorously with dimethyl sulfate (130 μL, 1.43 mmol, 8 eq) and 50% aqueous potassium hydroxide (0.5 ml) at rt for 18 h. The mixture was partitioned between water (30 ml) and etoac (30 ml), and the organic layer was then washed with brine, dried over sodium sulfate, and concentrated to a clear oil. The crude ether was purified by silica gel flash chromatography (Ether/Hexanes 3:7→9:113) to give 75 mg of the methyl ether as a clear oil.

Step B

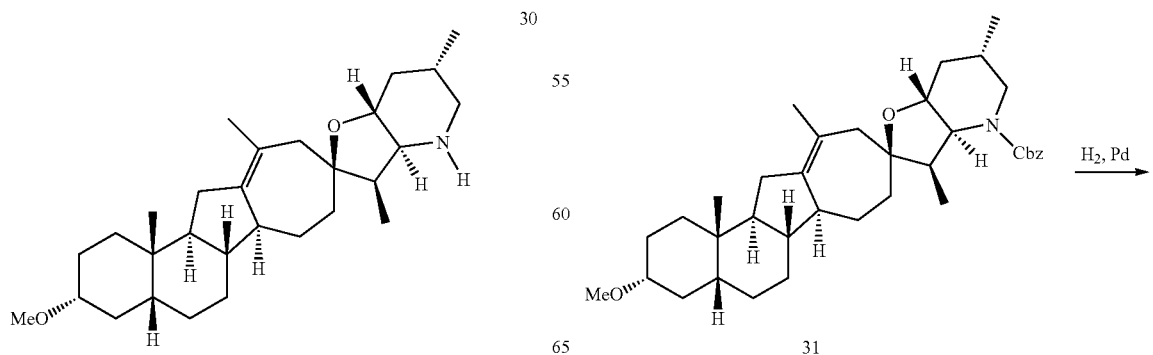

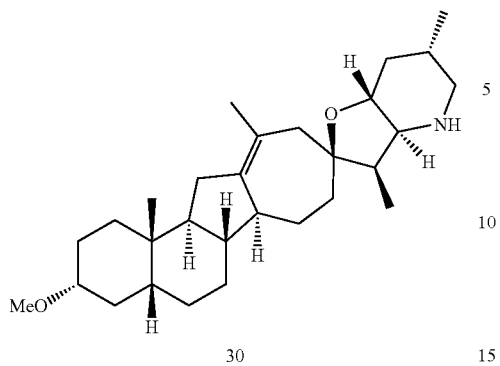

30

Compound 31 (66 mg, 0.115 mmol, 1 eq) was dissolved in etoac (5 ml) in a flask with stir bar and rubber septum. The solution was sparged with nitrogen, and Pd/C 10% (wet, Aldrich Degussa type E101, 20 mg) was added. This mixture was sparged with nitrogen and then hydrogen gas and stirred at rt for 3 h. The mixture was then sparged with nitrogen, filtered through a 0.45 μm polyethylene membrane and concentrated to a clear oil. The oil was purified by silica gel flash chromatography (NH$_4$OH(aq)/meoh/DCM 0.5:2:97.5→0.5:6:93.5) to give 22 mg of compound 30 as a white powder ([M+H]=441.4 m/z).

EXAMPLE 17

Step A

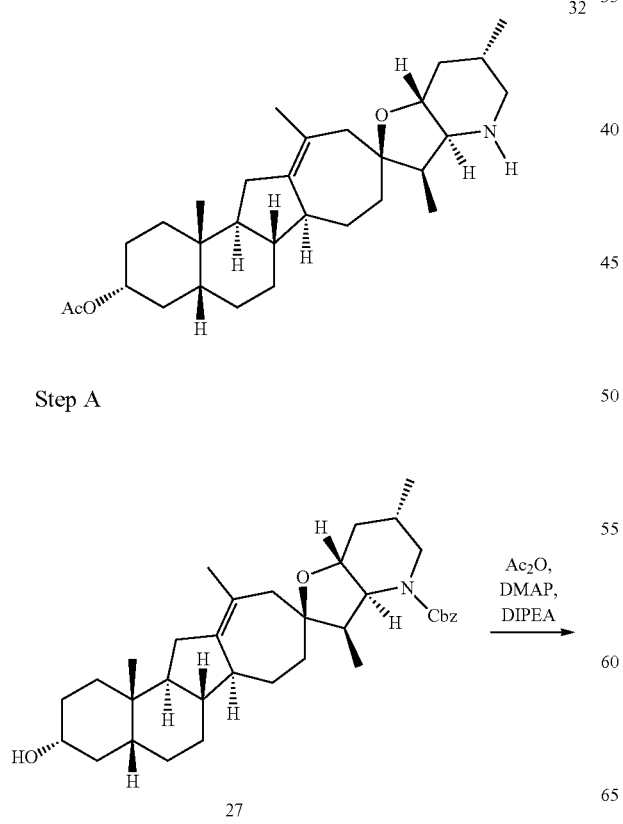

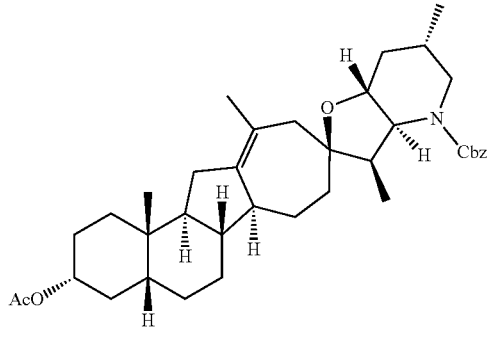

33

Compound 27 (100 mg, 0.18 mmol, 1 eq) was dissolved in DCM (5 ml), and 4-dimethylaminopyridine (4 mg, 0.35 mmol, 0.2 eq), N,N-diisopropylethylamine (0.15 ml, 0.9 mmol, 5 eq), and acetic anhydride (0.070 ml, 0.72 mmol, 4 eq) were added. After stirring for 12 h at rt, the solution was split between etoac (30 ml) and 5% aqueous sodium bicarbonate (15 ml). The organic layer was washed with brine, dried over sodium sulfate, and concentrated to a clear oil. The crude ester was purified by silica gel chromatography (Ether/Hexanes 3:7→9:113) to give 100 mg of the ester as a clear oil.

Step B

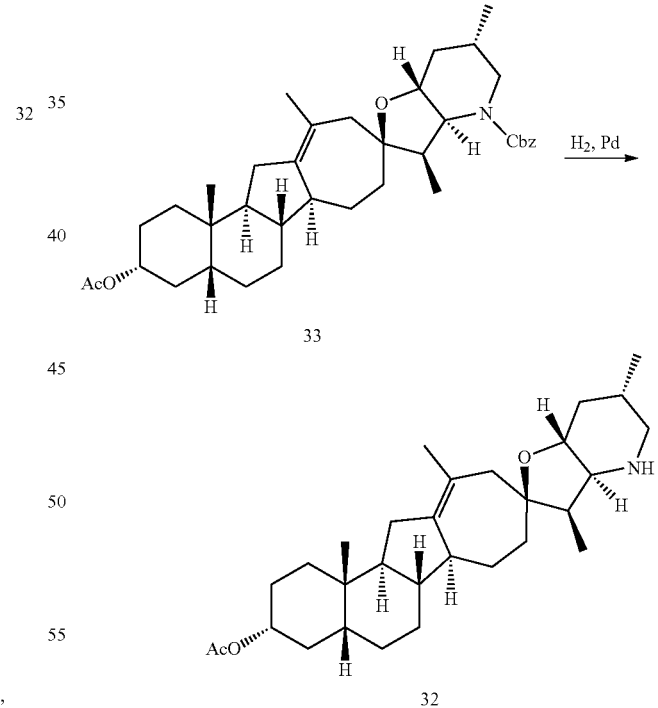

Compound 33 (100 mg, 0.18 mmol, 1 eq) was dissolved in etoac (5 ml) in a flask with stir bar and rubber septum. The solution was sparged with nitrogen, and Pd/C 10% (wet, Aldrich Degussa type E101, 20 mg) was added. This mixture was sparged with nitrogen and then hydrogen gas and stirred at rt for 3 h. The mixture was then sparged with nitrogen, filtered through a 0.45 μm polyethylene membrane and concentrated to a clear oil. The oil was purified by silica gel flash chromatography (NH₄OH(aq)/meoh/DCM 0.5:2: 97.5→0.5:6:93.5) to give 45 mg of compound 32 as a white powder ([M+H]=469.4 m/z).

EXAMPLE 18

34

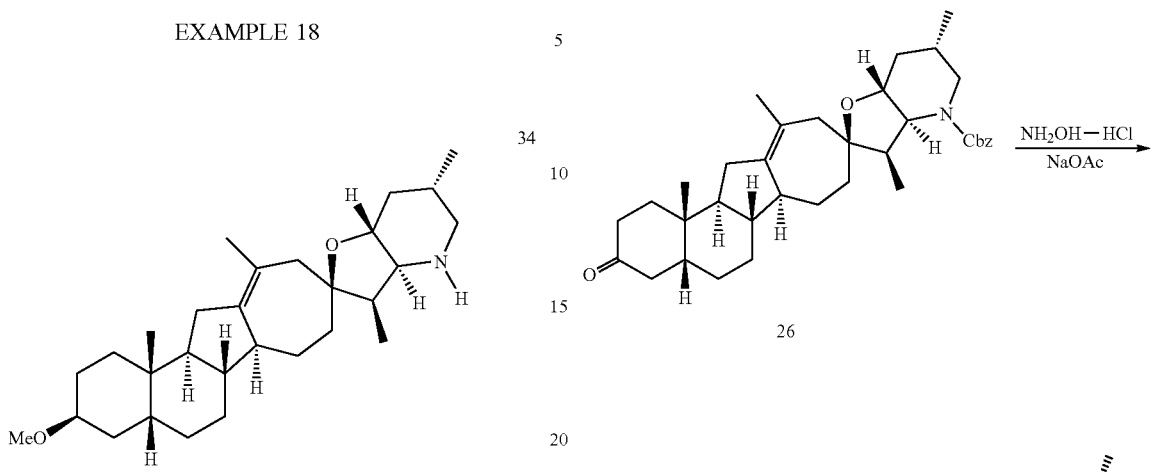

Compound 34 was synthesized according to the procedure described in example 16, using compound 29 in place of compound 27. ([M+H]=441.4 m/z).

EXAMPLE 19

35

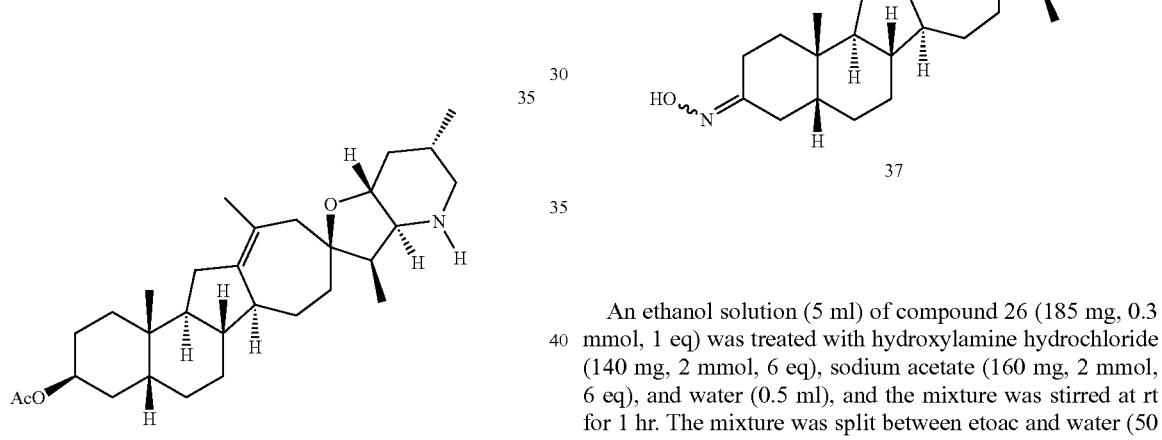

Compound 34 was synthesized according to the procedure described in example 17, using compound 29 in place of compound 27. MS ([M+H]=469.4 m/z)

EXAMPLE 20

36

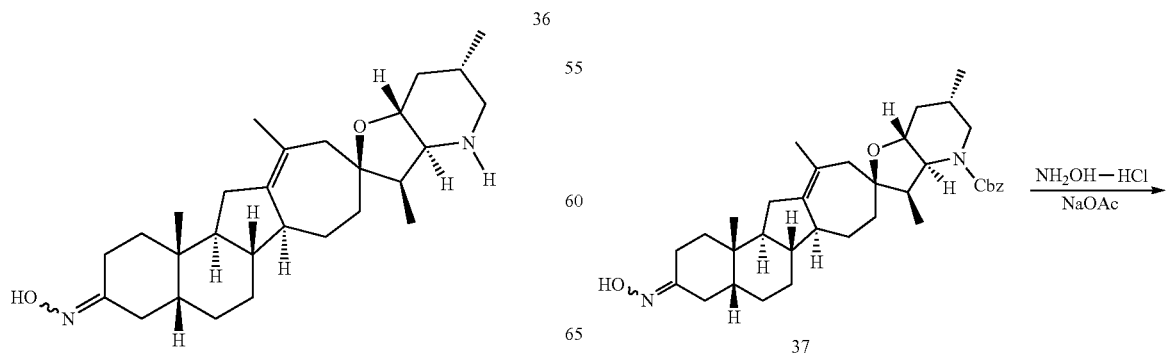

Step A

5

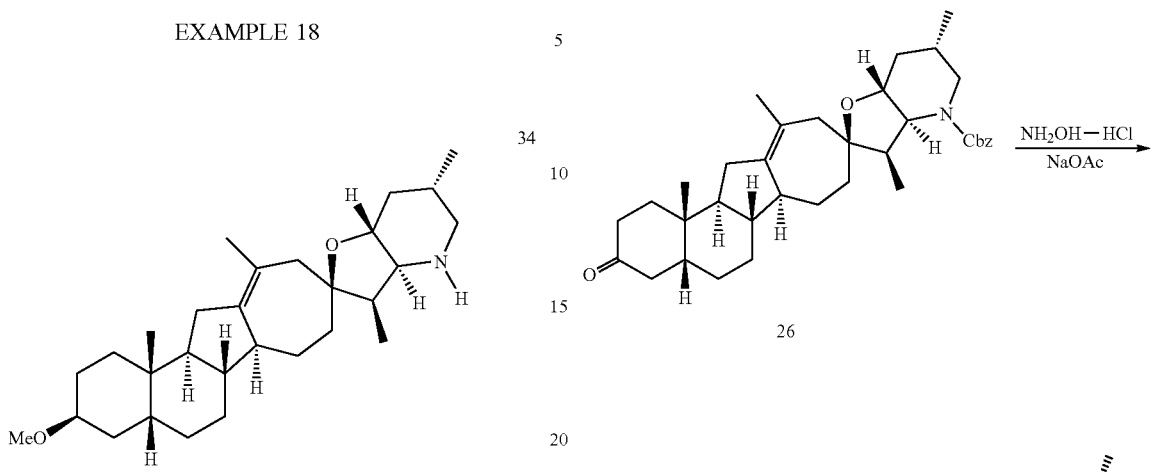

An ethanol solution (5 ml) of compound 26 (185 mg, 0.3 mmol, 1 eq) was treated with hydroxylamine hydrochloride (140 mg, 2 mmol, 6 eq), sodium acetate (160 mg, 2 mmol, 6 eq), and water (0.5 ml), and the mixture was stirred at rt for 1 hr. The mixture was split between etoac and water (50 ml each). The organic layer was washed with brine (30 ml), dried over sodium sulfate, and concentrated to a white residue. The crude product was purified by silica gel chromatography (ether/hexanes 2:3→1:1) to give 193 mg of oxime 37.

Step B

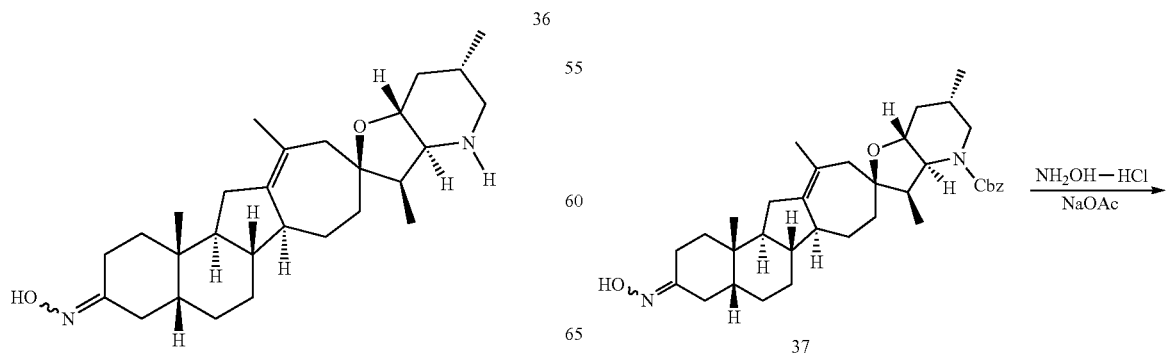

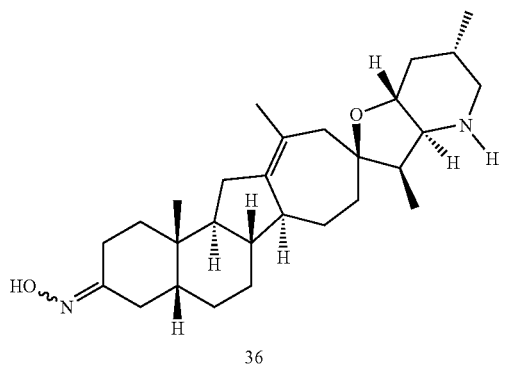

36

Compound 37 (65 mg, 0.113 mmol) was dissolved in etoac (7 ml) in a flask with stir bar and rubber septum. The solution was sparged with nitrogen, and Pd/C 10% (wet, Aldrich Degussa type E101, 20 mg) was added. This mixture was sparged with nitrogen and then hydrogen gas and stirred at rt for 3 h. The mixture was then sparged with nitrogen, filtered through a 0.45 μm polyethylene membrane and concentrated to a clear oil. The oil was purified by silica gel flash chromatography (NH$_4$OH(aq)/meoh/DCM 0.5:2:97.5→0.5:6:93.5) to give 15 mg of compound 36 as a white powder, a mixture of cis and trans oxime isomers ([M+H]=440.3 m/z).

EXAMPLE 21

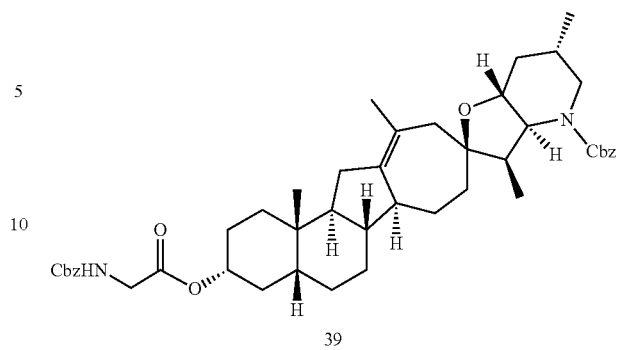

39

Compound 27 (42 mg, 0.075 mmol, 1 eq) was dissolved in DCM (5 ml), and 4-dimethylaminopyridine (2 mg, 0.02 mmol, 0.2 eq), N-Cbz glycine (23 mg, 0.110 mmol, 1.5 eq), and diisopropylcarbodiimide (0.023 ml, 0.150 mmol, 2 eq) were added. After stirring for 12 h at rt, the solution was split between etoac (30 ml) and 5% aqueous sodium bicarbonate (15 ml). The organic layer was washed with brine, dried over sodium sulfate, and concentrated to a clear oil. The crude ester was purified by silica gel flash chromatography (ether/hexanes 2:3→1:1) to give 35 mg of the ester as a clear oil Step B

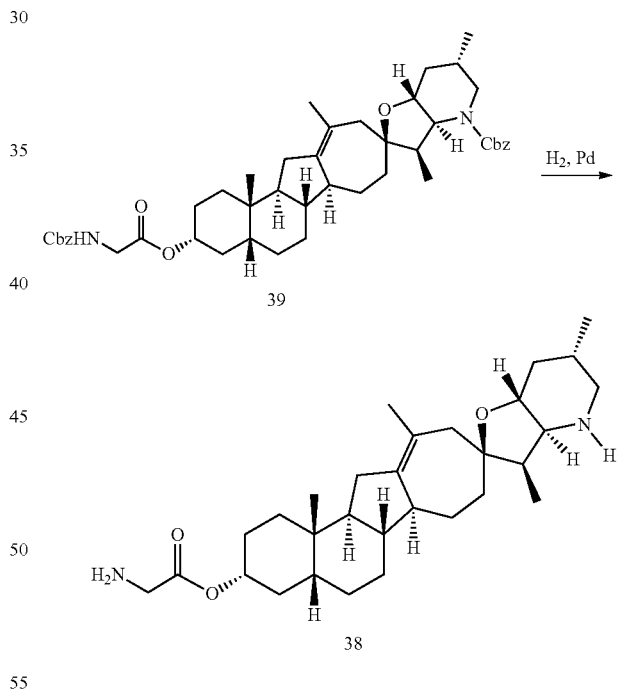

Compound 39 (235 mg, 0.42 mmol, 1 eq) was dissolved in etoac (7 ml) in a flask with stir bar and rubber septum. The solution was sparged with nitrogen, and Pd/C 10% (wet, Aldrich Degussa type E101, 50 mg) was added. This mixture was sparged with nitrogen and then hydrogen gas and stirred at rt for 3 h. The mixture was then sparged with nitrogen, filtered through a 0.45 μm polyethylene membrane and concentrated to a clear oil. The oil was purified by silica gel flash chromatography (NH$_4$OH(aq)/meoh/DCM 0.5:2:97.5→0.5:6:93.5) to give 17 mg of the desire product as a white powder ([M+H]=452.4 m/z).

38

Step A

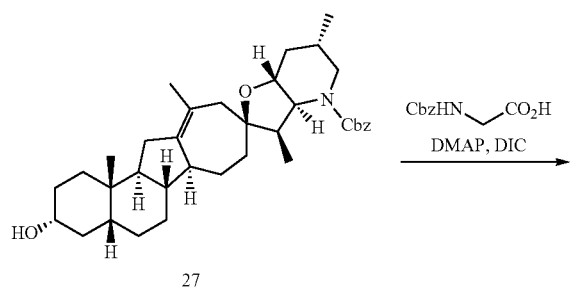

27

EXAMPLE 22

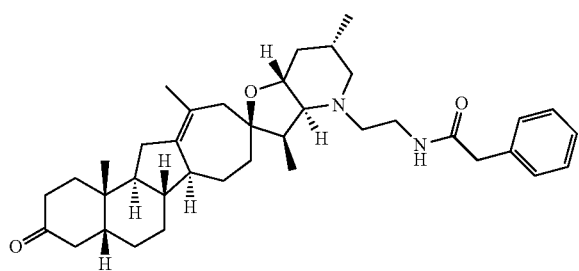

40

Compound 40 was synthesized according to the procedure described in example 21, using compound 29 in place of compound 27. ([M+H]=452.4 m/z)

EXAMPLE 23

41

Compound 41 was synthesized according to the procedure described in example 10, using N-(2-oxoethyl)-2-phenylacetamide in place of N-(2-oxoethyl)acetamide. ([M+H]=587.7 m/z).

EXAMPLE 24

42

Step A

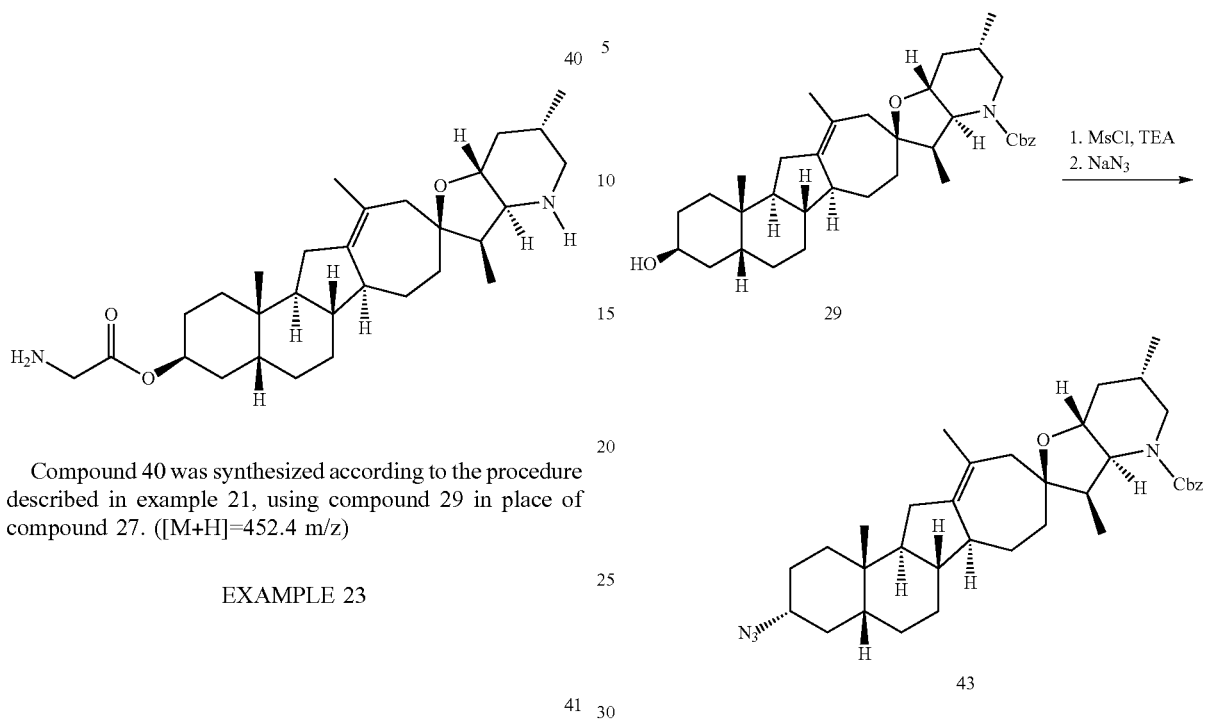

A round-bottom flask was charged with alcohol 29 (7.60 g, 13.53 mmol, 1 eq) and was dissolved in DCM (115 ml). The reaction was charged with triethylamine (8.21 g, 81 mmol, 6.0 eq). The mixture was cooled to 0° C. And charged with methanesulfonylchloride (1.86 g, 16.2 mmol, 1.2 eq). After 30 min, the reaction mixture was partitioned between a saturated aqueous solution of sodium bicarbonate and etoac. The organic layer was separated, dried over sodium sulfate and concentrated to dryness. The residue was purified using silica gel flash chromatography (etoac/hexanes 10→25%) gave the desired material mesylate.

A round-bottom flask was charged with the mesylate (9.1 g, 14.22 mmol, 1 eq) and was dissolved in 50 ml of DMPU. The reaction was charged with sodium azide (4.62 g, 71.1 mmol, 5.0 eq) and heated to 60° C. The mixture was stirred for 17 h. The reaction mixture was then cooled to rt and charged with water. The mixture was stirred for 30 min. The mixture was filtered under vacuum, rinsed with water and air dried and used directly without purification in the next step.

Step B

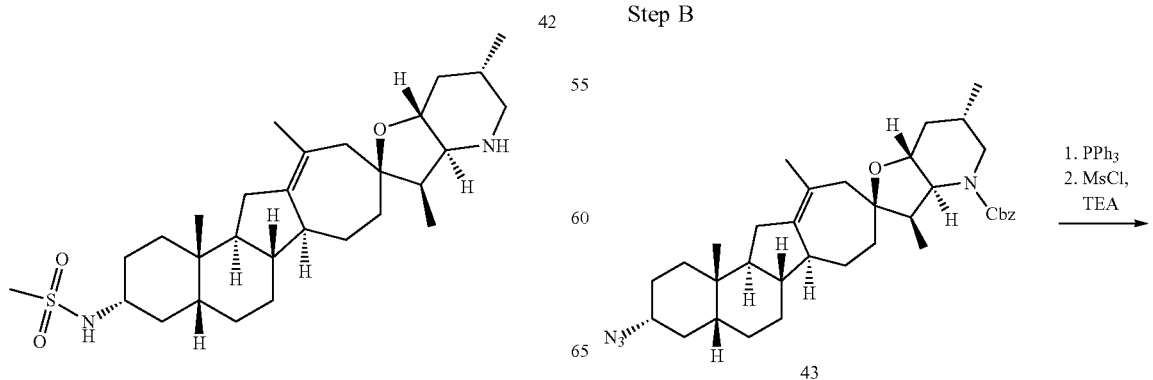

-continued

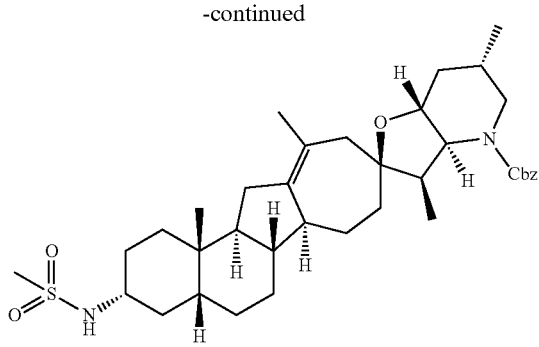

44

A round-bottom flask was charged with azide 43 (8.35 g, 14.23 mmol, 1 eq) and THF (120 ml) was added. The reaction was then charged with triphenylphosphine (11.2 g, 42.7 mmol, 3.0 eq). The mixture was heated to 50° C. And stirred for 20 h. The reaction mixture was then cooled to rt and the solvent removed under vacuum. The residue purified using silica gel flash chromatography (meoh/DCM 10%→20%) to afford the amine.

A round-bottom flask was charged with the amine (5.10 g, 9.09 mmol, 1 eq) and was dissolved in DCM (60 ml). The reaction was charged with N,N-diisopropylethylamine (5.88 g, 45.5 mmol, 5.0 eq). The mixture was cooled to 0° C. And charged with methanesulfonylchloride (2.08 g, 18.2 mmol, 2.0 eq). After 30 minutes, the reaction mixture was partitioned between a saturated aqueous solution of sodium bicarbonate and etoac. The organic layer was collected, dried over sodium sulfate and concentrated to dryness. The residue was purified using silica gel flash chromatography (etoac/hexanes 10→30%) to afford the Cbz protected methanesulfonamide.

Step C

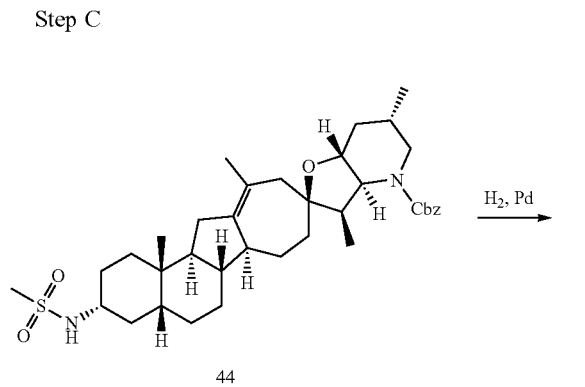

42

A round-bottom flask was charged with the Cbz protected methanesulfonamide (5.37 g, 8.41 mmol, 1 eq) and 10% palladium on carbon (1.0 g). The solids were suspended in 2-propanol (50 ml). The suspension was placed under hydrogen atmosphere and the mixture was stirred for 4 h at 25° C. The reaction mixture was then filtered on Celite® and the filtrate concentrated to dryness. The residue was then purified using silica gel flash chromatography (DCM/meoh 0→5%) to afford the desired product. [M+H]=505.6 m/z.

Alternate Synthesis of Compound 42

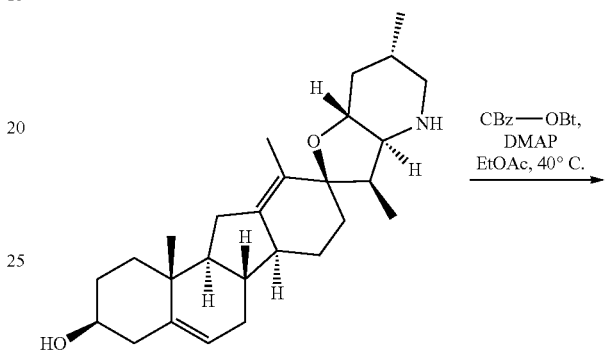

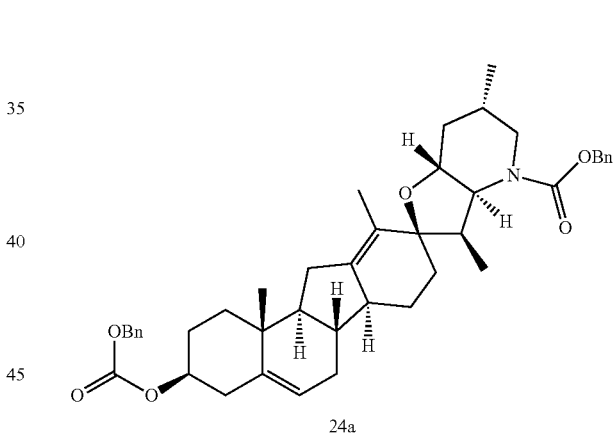

24a

Recrystallized cyclopamine (2.07 g) is charged to an appropriately sized reaction vessel and placed under an inert atmosphere. Etoac (7.6 g), triethylamine (1.53 g), and DMAP (307 mg) are added sequentially. The suspension is warmed to 40° C. Cbz-obt is added in three portions over 90 minutes, keeping the internal temperature below 45° C. The reaction mixture is stirred at 40° C. For 90 minutes. The temperature is maintained while methanol (26.4 g) is slowly added to the reaction mixture. The resulting suspension is cooled to room temperature and stirred for at least 15 hours. The crude product is collected by filtration and rinsed with methanol (5 g). The white solid is dried under vacuum to a constant weight and recrystallized from heptane (30.3 g) and toluene (3.2 g) to afford Compound 24a (3.0 g).

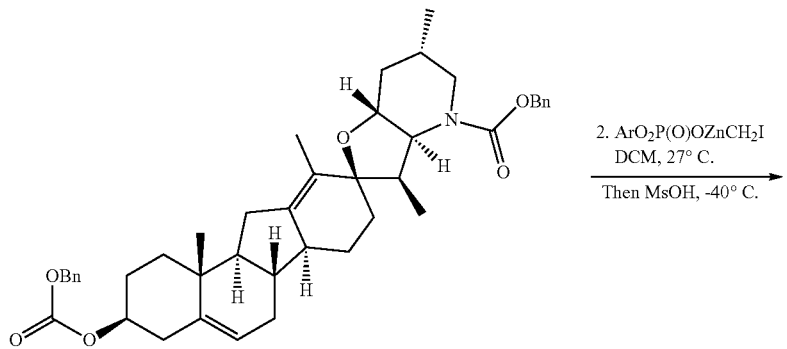

24a

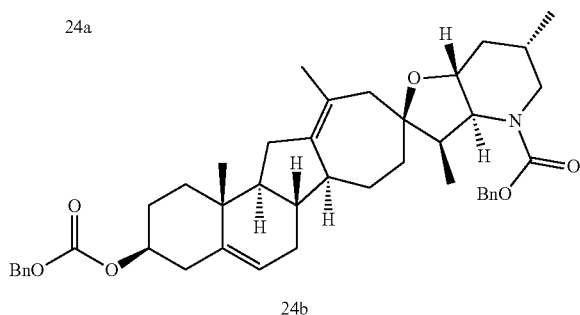

24b

Solid bis(2,6-dimethylphenyl) hydrogenphosphate and 24a are pre-dried and placed under a nitrogen atmosphere. Neat diethyl zinc (722 mg) is charged to an appropriately sized reaction vessel containing DCM (9.0 g). DCM solutions of the phosphate (1.83 g in 17.9 g) and IPI-332690 (1.34 g in 3.6 g) are added sequentially at or below 25° C. Diiodomethane (1.58 g) is charged and the reaction is stirred at 28° C. For 4-6 hours. The reaction is cooled to −45° C. And a solution of methanesulfonic acid in DCM (566 mg in 1.5 g) is charged. After 15 minutes, morpholine (1.711 g) is added and the mixture is allowed to warm to room temperature overnight. The organic layer is washed twice with 2N hcl (2×13.6 g) then sequentially with 4.8 wt % sodium carbonate (aq), 4.8 wt % sodium sulfite (aq), and 4.8 wt % brine (13.6 g each). The organic layer is dried, filtered, concentrated to 4 g and diluted with isopropanol (4 g). The product is crystallized from solution by the slow addition of methanol (9.3 g). Filtration with a methanol rinse (2.6 g) and drying afford 1.09 g of 24b (79% isolated yield).

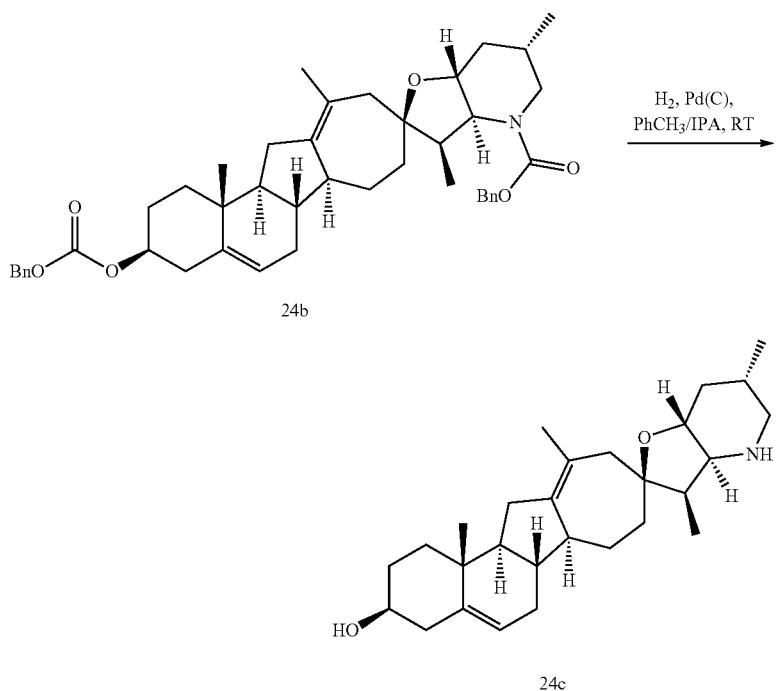

24b

24c

Johnson Matthey Pd/C catalyst A-305038-5 (890 mg) is charged to an appropriately sized reaction vessel, followed by 24b (2.24 g). The reaction vessel is purged with N₂ and toluene (21.8 g) and 2-propanol (6.7 g) are added sequentially. The system is degassed and placed under a nitrogen atmosphere, and the process is repeated with hydrogen. The system is stirred vigorously and the hydrogen blanket is maintained at one atmosphere for 4-5 hours. The reaction is monitor by either TLC or HPLC. If incomplete, the reaction is inerted, additional catalyst (145 mg) is charged, and the hydrogen atmosphere is returned for another hour. Ethylenediamine (12.9 mg) is charged and the mixture was stirred for 15 minutes. The catalyst is removed by filtration with a toluene:IPA (3:1) rinse. He filtrate and rinses are concentrated and solvent exchanged to toluene. The product is crystallized from toluene (19.0 g) and heptane (18.0 g) to afford 24c as a white crystalline solid (1.34 g, 98% yield).

layers are combined and washed with fresh Rochelle's salt solution (2.6 g in 10.3 g water) and then with water (12.9 g). The resulting organic layer is dried over sodium sulfate (1.97 g), filtered, and concentrated in vacuo. The product is crystallized via a charge and concentration solvent exchange first to IPA (6.5 g) and then Heptane (7.7 g). The thick heptane slurry (~2.7 g) is stirred overnight and solids are collected by filtration. Vacuum drying affords 24d (550 mg) in an 85% yield.

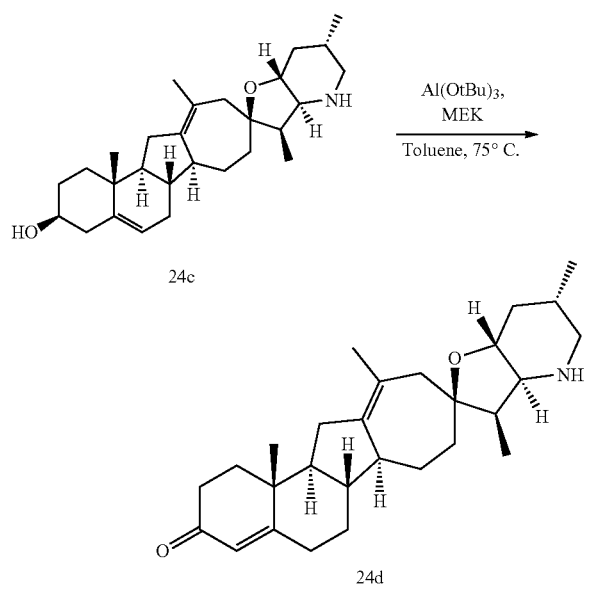

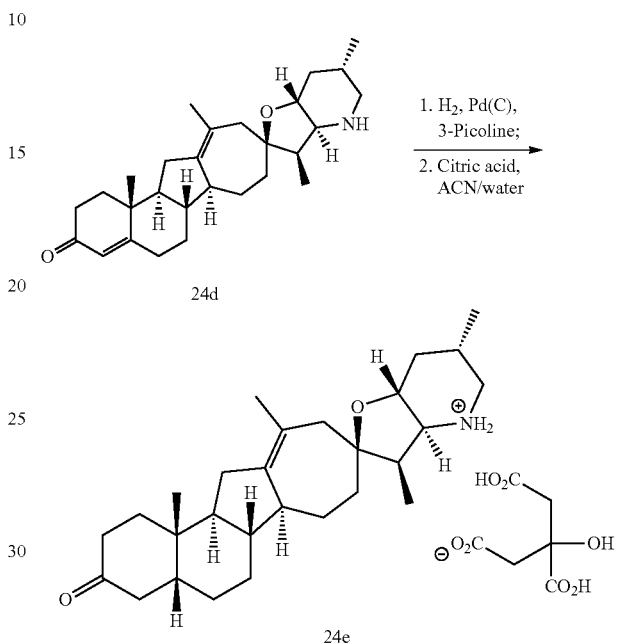

24c (644 mg) is charged to an appropriately sized reaction vessel followed by aluminum t-butoxide (525 mg), toluene (8.34 g, 15 vol), and 2-butanone (7.83 g, 15 vol). The contents of the flask are degassed with evacuation/nitrogen purge cycles to remove oxygen and the reaction mixture is heated at 75° C. With vigorous stirring for 16-18 hours. The reaction is quenched by the addition of aqueous Rochelle's salt (2.6 g in 10.3 g water) and the mixture vigorously stirred for one hour at 45° C. The aqueous and organic layers are separated. The aqueous layer is back extracted with a mixture of toluene (2.9 g) and etoac (2.9 g). The organic The enone 24d (459 mg) and Johnson-Matthey 5% palladium on carbon (A503023-5, 101 mg) are charged to an appropriately sized multi neck reaction vessel. The vessel is purged with nitrogen and 3-picoline (2.2 g) is charged as the solvent. Stirring is started and the vessel is first degassed using nitrogen and then stirred under hydrogen at atmospheric pressure for 8 hours. At the end of the reaction, the catalyst is removed by filtration through 0.2 micron media, rinsing with ACN (1.4 ml). The filtrate and rinse are combined in a clean reaction vessel equipped with mechanical stirring, an internal temperature probe, and a nitrogen atmosphere. A solution of citric acid (3.7 g) in water (9.2 ml) is charged to the reaction vessel at or below 30° C., and IPI-335589 is allowed to slowly crystallize from solution as the citrate salt at 20 and then 0° C. The crystalline product is recovered by suction filtration and washed with water (3.7 ml). After drying, the citrate salt, 24e, is isolated as a hydrate (3-5 wt % water) in 89.5% yield (622 mg) with a β:α ratio approaching 90:1.

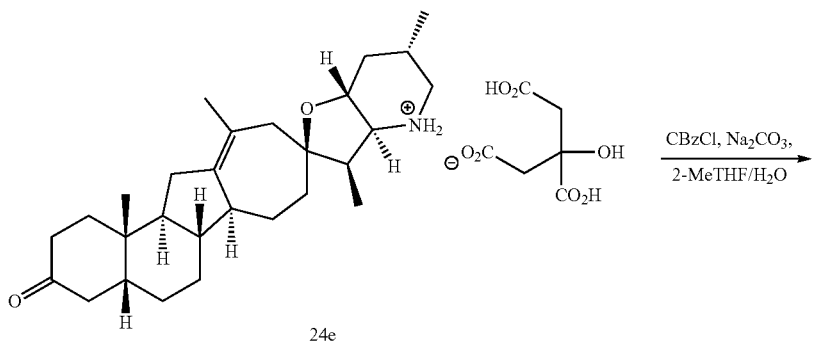

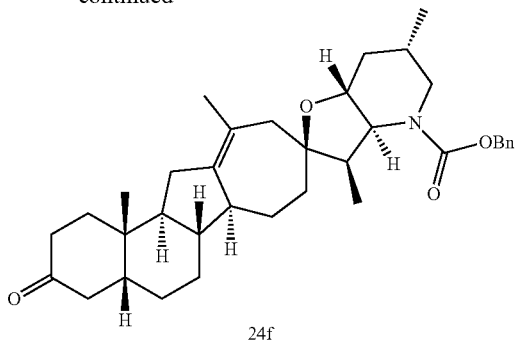

24e (1.50 g) is charged to the appropriately sized reactor along with 2-methyltetrahydrofuran (7.7 g) and 1M sodium carbonate (9.0 ml) A solution of benzyl chloroformate (454 mg) in 2-methyltetrahydrofuran (300 mg) is added via addition funnel and the reaction is ambient temperature for 1-2 hours. When the reaction is complete, the stirring is stopped, the layers are separated and the organic layer is washed twice with water (2×6 g). The organic layer is dried over of sodium sulfate (3 g), filtered and concentrated. Residual water is reduced further by concentration from fresh 2-methyltetrahydrofuran (6.5 g) and the material is transferred as solution in anhydrous 2-methyltetrahydrofuran to the next reaction.

3M naoh (2.4 g) at −20° C. And 15% hydrogen peroxide in water (1.04 g) at or below 5° C., then stirring overnight at ambient temperatures. The layers are split and the organic layer is washed sequentially with 1M aqueous naoh (2 ml), 0.5 M aqueous $Na_2SO_3$ (2 ml), and water (2 ml) adjusted to a ph of 3 with hcl. The organic layer is dried over sodium sulfate (0.82 g), filtered and concentrated. The product 24 g (0.457 g) is re-concentrated from DCM (0.9 g) and used in the next reaction.

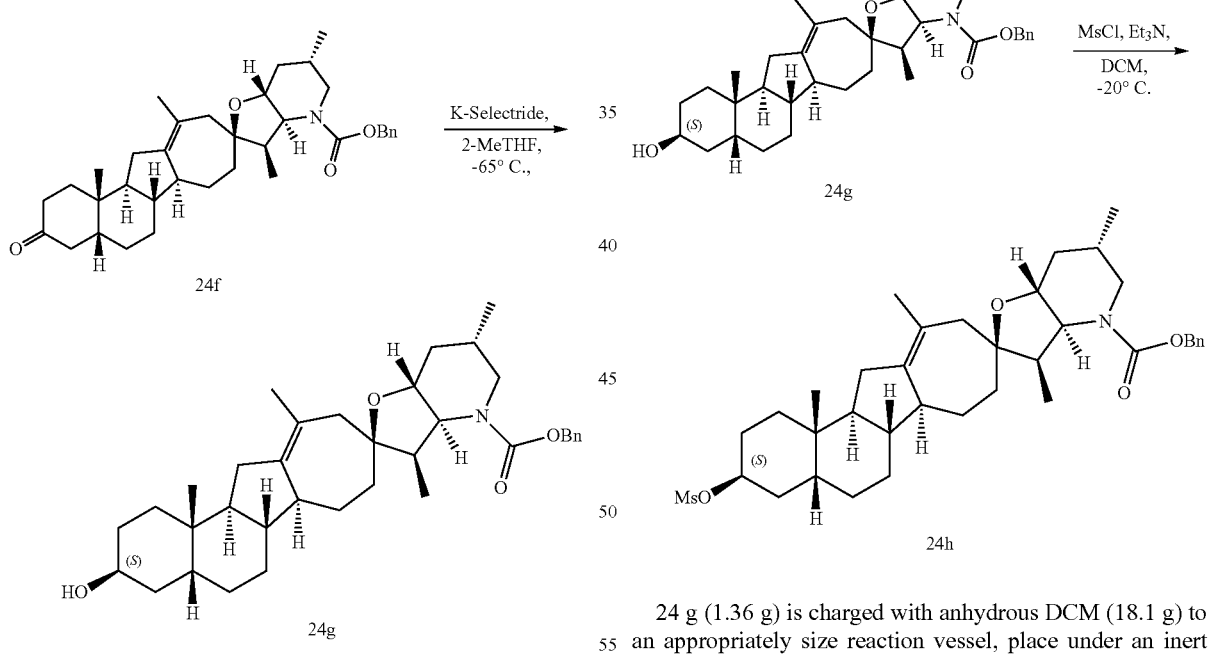

Commercial 1 M K-Selectride in THF (1.20 g) is charged to a dry reaction vessel under a nitrogen atmosphere, diluted with anhydrous 2-methyltetrahydrofuran (2.10 g) and cooled to −65° C. The solution of 24f (0.41 g) in 2-methyltetrahydrofuran (1.5 g), is then slowly added to the reaction vessel to control the internal temperature at −65±5° C. The reaction is stirred for 2 hours and warmed to −20° C. Over approximately 1 hour and stirred for an additional hour. The reaction is monitored by HPLC and reactions that are incomplete are driven to completion with additional K-selectride. The reaction is quenched at low temperature with meoh (0.33 g), then 24 g (1.36 g) is charged with anhydrous DCM (18.1 g) to an appropriately size reaction vessel, place under an inert atmosphere and cooled to −20° C. Triethylamine (0.61 mg) is charged followed by the slow addition of methanesulfonyl chloride (373 mg) in anhydrous DCM (300 mg). The reaction is stirred for 1 hour at −20° C. The reaction is monitored by HPLC. Incomplete reactions are driven to completion with additional methanesulfonyl chloride. When complete, the reaction is quenched with water (13.6 g) and allowed to warm. The layers are separated and the organic layer is washed with 2.5 wt % sodium bicarbonate (13.8 g) and then water (10.9 g). The organic layer is dried over of sodium sulfate (4 g), filtered, and concentrated. The product solution is solvent exchanged via charge and concentration to t-butyl methyl ether (10.9 ml) and then 1,3-dimethyl-3,4,5,6-tetrahydro-2(1H)-pyrimidinone (DMPU, 4.7 ml). The DMPU solution is used directly in the next reaction.

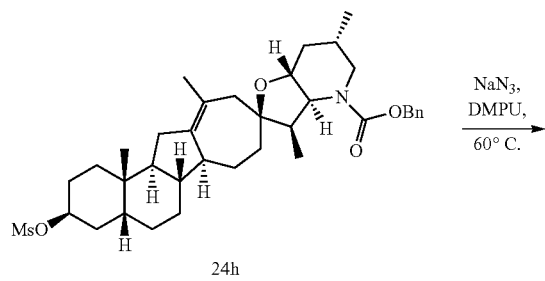

24h

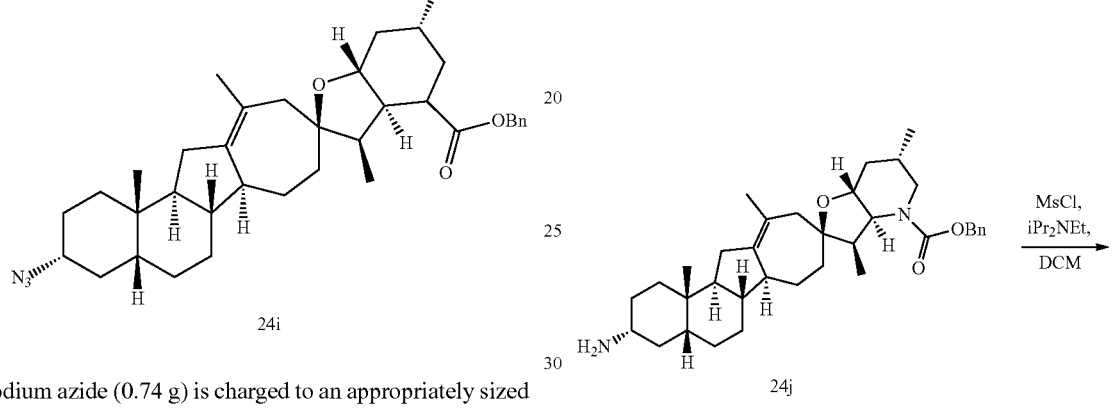

24i

Sodium azide (0.74 g) is charged to an appropriately sized reaction vessel. The solution of 24 h (1.46 g) in DMPU (5.9 g) is charged to the reaction vessel, rinsing with additional DMPU (1.9 g). The suspension is heated to 60° C. For 15 hours, maintaining a nitrogen sweep for the entire reaction. The reaction is cooled to ambient temperature and diluted with MTBE (11.7 g). The organic solution is washed 3 times with 2% saline (3×8 g), dried over sodium sulfate (4.4 g), filtered, and concentrated. The product is concentrated from THF (6.4 g) and used directly in the next reaction.

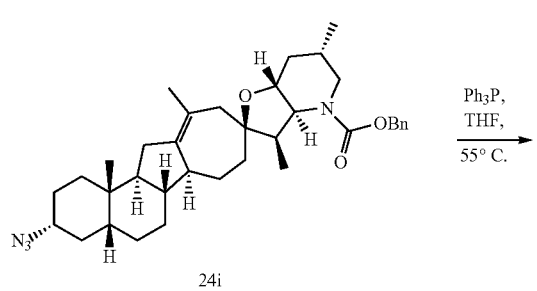

24i

24j

The crude 24i (1.34 g) is dissolved and transferred to a suitably sized reaction vessel with THF (12.6 g). Triphenylphosphine (0.70 g) and water (0.44 g) are charged and the reaction is heated to 55° C. For 15-24 hours. When complete, the reaction is cooled to ambient temperature, dried with magnesium sulfate (1.4 g), filtered and concentrated. The solids are dissolved and concentrated from three portions of DCM (3×9 g) and purified by silica gel chromatography using DCM/meoh/Et$_3$N gradients to remove reagent based impurities. The pooled fractions are concentrated to dryness, dissolved in DCM (6.8 g) and concentrated to dryness again to afford an amorphous solid (1.12 g) which is used in the next reaction.

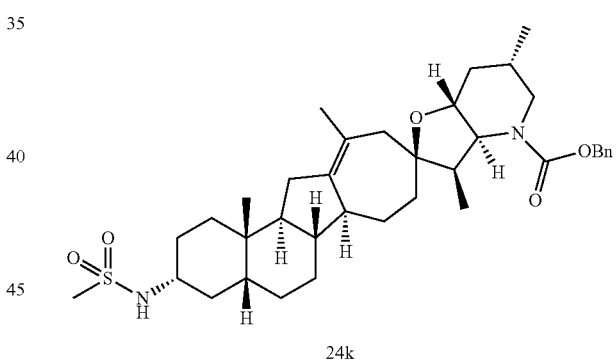

24j

24k 24j (1.09 g) is dissolved and transferred to an appropriately sized reaction vessel with anhydrous DCM (15.8 g) and placed under a nitrogen atmosphere. The solution is cooled to 0° C. N,N-diisopropylethylamine (357 mg) and neat methanesulfonyl chloride (0.165 ml) are charged sequentially while maintaining temperature between below 5° C. The reaction is monitored by HPLC. Incomplete reactions are driven to completion with additional methanesulfonyl chloride. The reaction is quenched with 0.4 M aqueous sodium bicarbonate (11.4 g) and warmed to ambient temperature. The layers are separated and the aqueous phase is back extracted with DCM (5.8 g). The combined organic layers are dried over magnesium sulfate (0.55 g), filtered and concentrated. The product 24k is dissolved and striped from 2-propanol (4.0 g) to remove residual DCM and used directly in the next reaction.

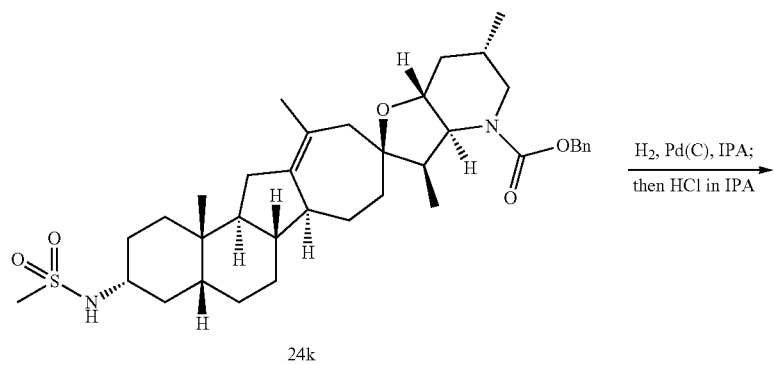

24k

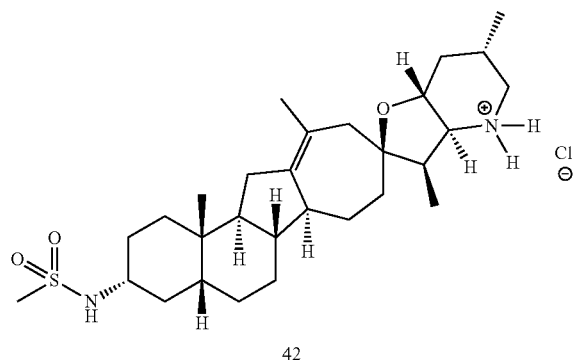

42

Aldrich Degussa type E101 NE/W 10% Pd/C (249 mg) is charged to an appropriately sized reaction vessel and placed under a nitrogen atmosphere. A 2-propanol (9.8 g) solution of 24k (1.24 g) is charged to the reaction vessel. The system is degassed and placed under a nitrogen atmosphere, and the process is repeated with hydrogen. The reaction is stirred under a 1 atm of hydrogen at ambient temperature for 8 hours. An inert atmosphere is returned to the vessel and a second charge of catalyst (125 mg) slurried in 2-propanol (0.5 g) is added to the reaction. The reaction mixture is degassed and placed under a nitrogen atmosphere, and the process is repeated with hydrogen. The reaction is stirred under 1 atm of hydrogen for another 15 hours at ambient temperature. The reaction is monitored by HPLC. Incomplete reactions are treated with additional catalyst and hydrogen. When complete, the reaction is filtered, treated with steam activated carbon (200 mg), and filtered again. The solution is dried by partial concentration transferred to a reaction vessel and diluted with anhydrous 2-propanol to 0.09 M based on the theoretical yield. A 1.25 M hcl solution in 2-propanol (1.64 g) is charged over 20 minutes. The hydrochloride salt crystallizes slowly with gentle stirring and is isolated by filtration. The crystals are washed with 2-propanol (2.5 g) and vacuum dried to afford Compound 42 (916 mg, 80% yield) as a 1:1 IPA solvate.

EXAMPLE 25

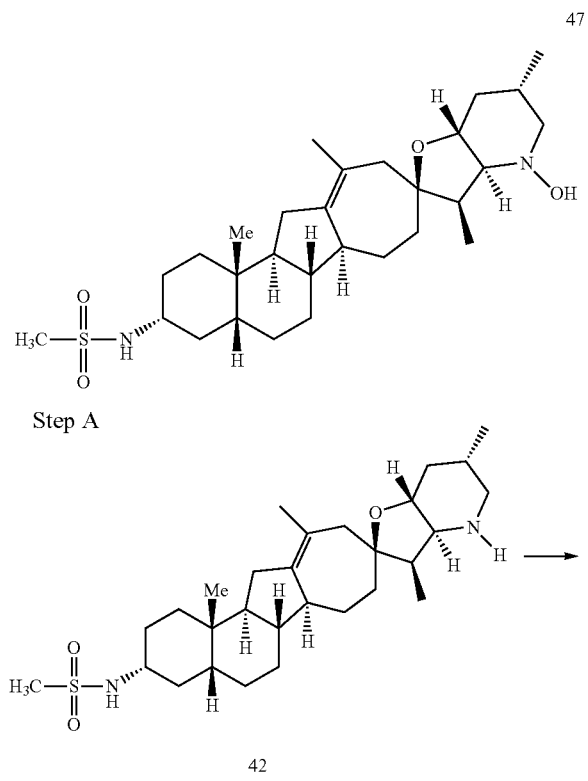

Step A

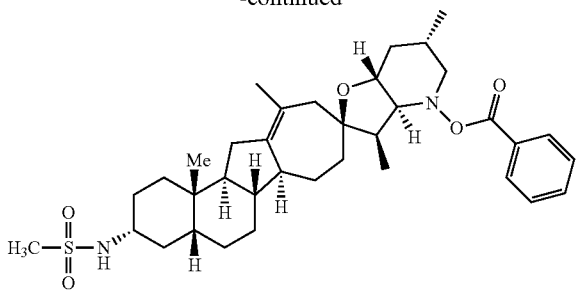

48

A round-bottom flask was charged with the amine 42 (1.1 g, 2.1 mmol, 1 equiv.), dry tetrahydrofuran (10 ml) and pyridine (880 ul, 10.9 mmol, 5 equiv.). The cooled (0° C.) Mixture was treated with benzoylperoxide (1.6 g, 6.5 mmol, 3 equiv.). The mixture was stirred for 2 hours at 0° C. Then overnight at 25° C. Reaction mixture diluted with MTBE and washed with a mixture of saturated aqueous nahco₃ with 1 N naoh until the layer split. The organic layer was collected and the aqueous was re-extracted once with MTBE. Combined organic layers were washed with brine, dry over Na₂SO₄, filtered and concentrated to dryness. The crude oil was dissolved in 5 ml of CH₂Cl₂, loaded onto sio₂ (40 g) column and eluted from hexanes/etoac (10% to 50%) to give the benzoyl derivative 48 (380 mg) ([M+H]=625.4 m/z).

Step B

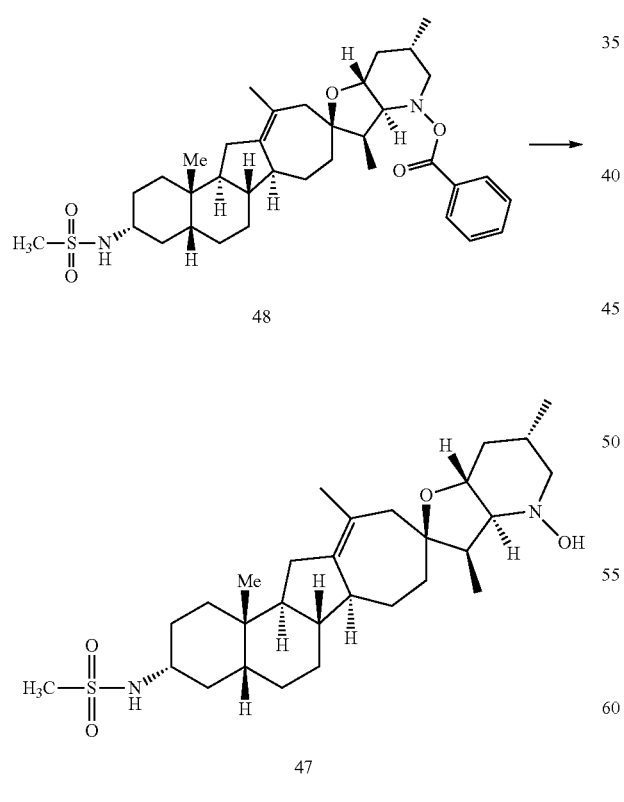

A round-bottom flask was charged with 48 (374 mg, 0.6 mmol, 1 equiv.) And meoh (5 ml). The solution was treated at 25° C. In presence of 2 N KOH (0.3 ml, 0.6 mmol, 1 equiv.). The mixture was stirred for 3 h. The solvent was removed under vacuum. MTBE was added to the residue, which was neutralized with 1N hcl. The layers were cut and the aqueous layer was extracted with two portions of CH₂Cl₂. Combined organic layers were dried over Na₂SO₄, filtered, and concentrated to dryness. The crude material (380 mg) was dissolved with CH₂Cl₂, loaded onto a sio₂ column (12 g) and eluted with hexanes/etoac (0% to 100%) to give the hydroxylamine 47. The material was lyophilized from t-buoh/7% H₂O to give 213 mg of 47 as a white powder ([M+H]=521.4 m/z).

EXAMPLE 26

50

Step A

51

A heat-gun dried flask was charged with dry CH₂Cl₂ (5 ml) and benzyl alcohol (785 ul, 7.58 mmol, 1.3 equiv.). The cooled (0° C.) Solution was treated with chlorosulfonyl isocyanate (506 ul, 5.83 mmol, 1 equiv.). Then, DMAP (1.4 g, 11.6 mmol, 2 equiv.) Was added and the mixture was stirred for 1 h at 25° C. After complete dissolution of DMAP, the reaction was clear for a short period. Then, a white fluffy precipitate formed. The mixture was diluted with CH₂Cl₂ (30 ml) and washed with three portions (30 ml each) of water. The organic layer was dried over Na₂SO₄, filtered, and evaporated to dryness. The desired white solid 51 was taken to the next step without purification.

Step B
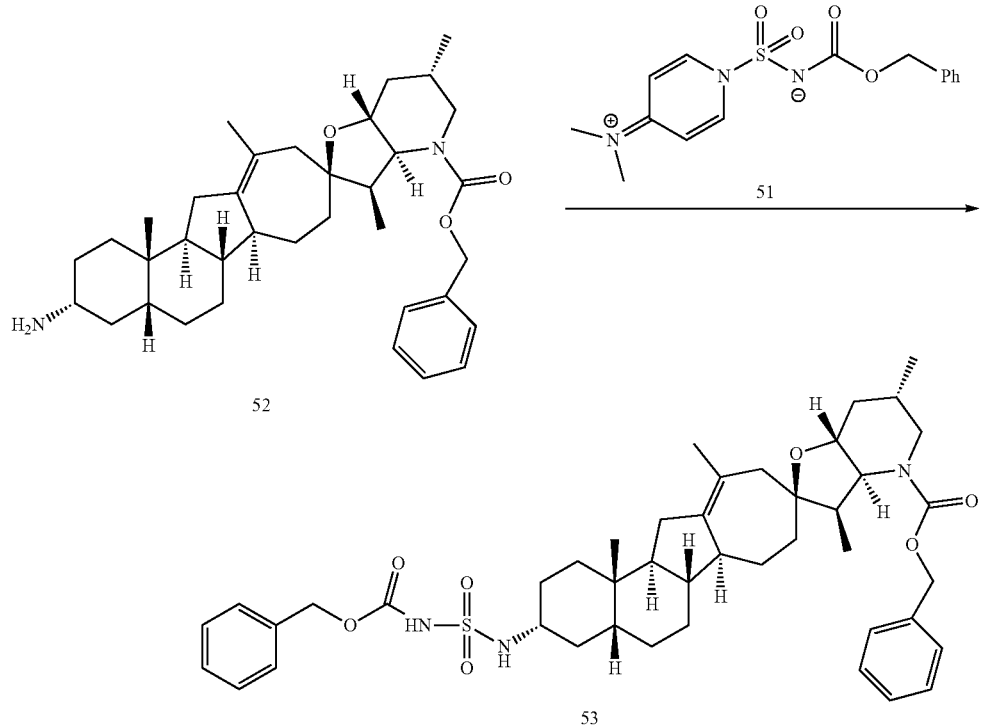
A round-bottom flask was charged with 52 (30 mg, 0.053 mmol, 1 equiv.) And 51 (18 mg, 0.053 mmol, 1 equiv.). Both reagents were dissolved in CH$_2$Cl$_2$ (2 ml) and the solution was stirred at 25° C. The crude material was loaded onto a sio$_2$ column (4 g) and eluted with hexanes/etoac (0% to 50%) to give 16 mg of the sulfamoylated derivative 53 ([M+Na]=796.4 m/z).
Step C
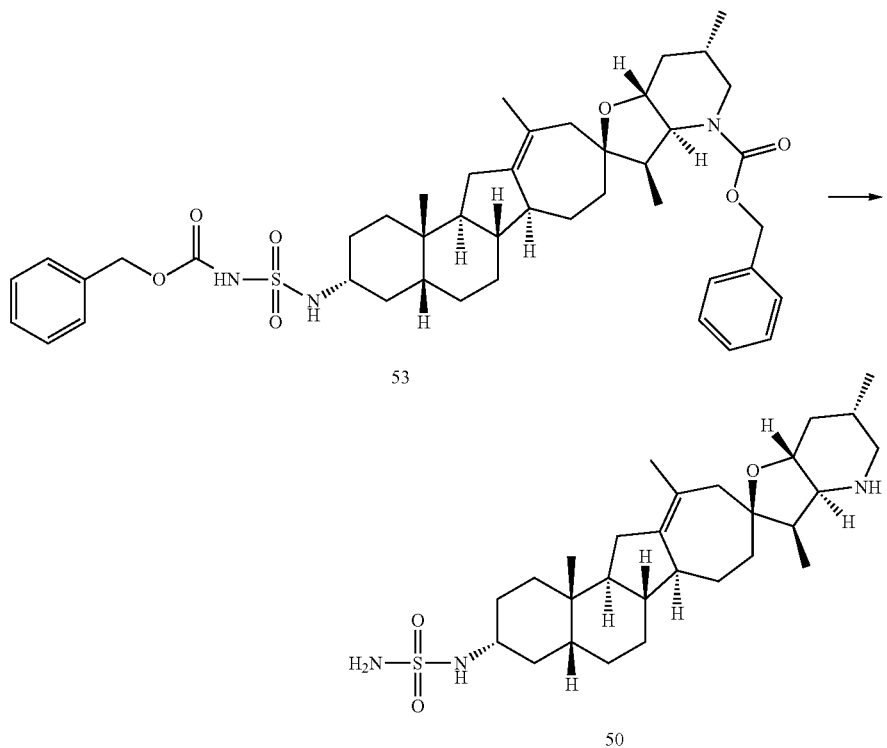

A round-bottom flask was charged with 53 (16 mg, 0.021 mmol, 1 equiv.) And 11 mg of 10% Pd/C (wet, Aldrich Degussa type E101). The material was suspended in 2-propanol (3 ml). The flask was sealed and purged three times with hydrogen and left overnight under 1 atm of hydrogen. The slurry was filtered through 0.2 micron Acrodisc, washed with 2-propanol, and the solvent was removed under vacuum. The residue was purification by $sio_2$ column (1 g) eluting with $CH_2Cl_2$/meoh (5% to 10%). The major product was lyophilized from t-buoh/7% $H_2O$ to give 9 mg of sulfamide 50 ([M+H]=506.4 m/z).

EXAMPLE 27

Step A

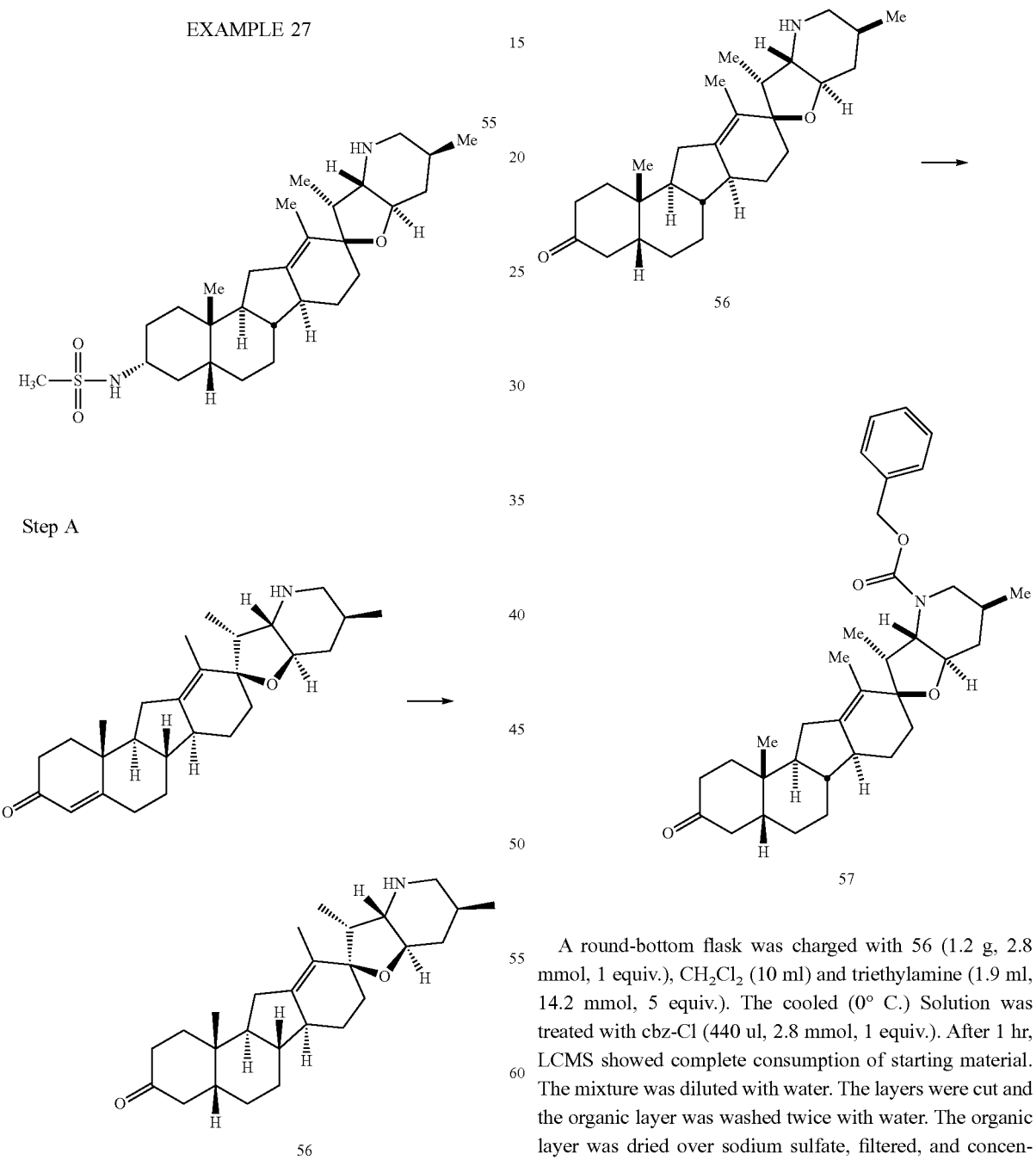

A round-bottom flask was charged with cyclopamine 4-en-3-one (3.5 g, 8.5 mmol, 1 equiv.) And pyridine (70 ml).

The reactor was charged with Pd/C (10% Pd, 500 mg). The reaction was placed under 1 atmosphere of hydrogen. After 3.5 hrs, LCMS showed complete consumption of starting material. The catalyst was filtered off on an Acrodisk 0.2 micron filter and washed with toluene. The solvent was removed by azeotropic removal with toluene (2×10 ml). The desired material 56, 3.5 g ([M+H]=412.5 m/z) was used as it for the next step.

Step B

A round-bottom flask was charged with 56 (1.2 g, 2.8 mmol, 1 equiv.), $CH_2Cl_2$ (10 ml) and triethylamine (1.9 ml, 14.2 mmol, 5 equiv.). The cooled (0° C.) Solution was treated with cbz-Cl (440 ul, 2.8 mmol, 1 equiv.). After 1 hr, LCMS showed complete consumption of starting material. The mixture was diluted with water. The layers were cut and the organic layer was washed twice with water. The organic layer was dried over sodium sulfate, filtered, and concentrated to dryness. The product was purified by column chromatography (sio2, 40 g) eluting with hexane/etoac (0 to 20%) to give 57 (891 mg) ([M+Na]=468.4 m/z).

Step C

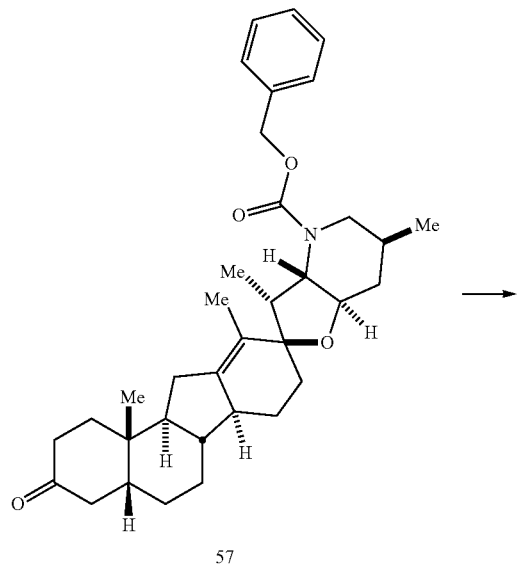

57

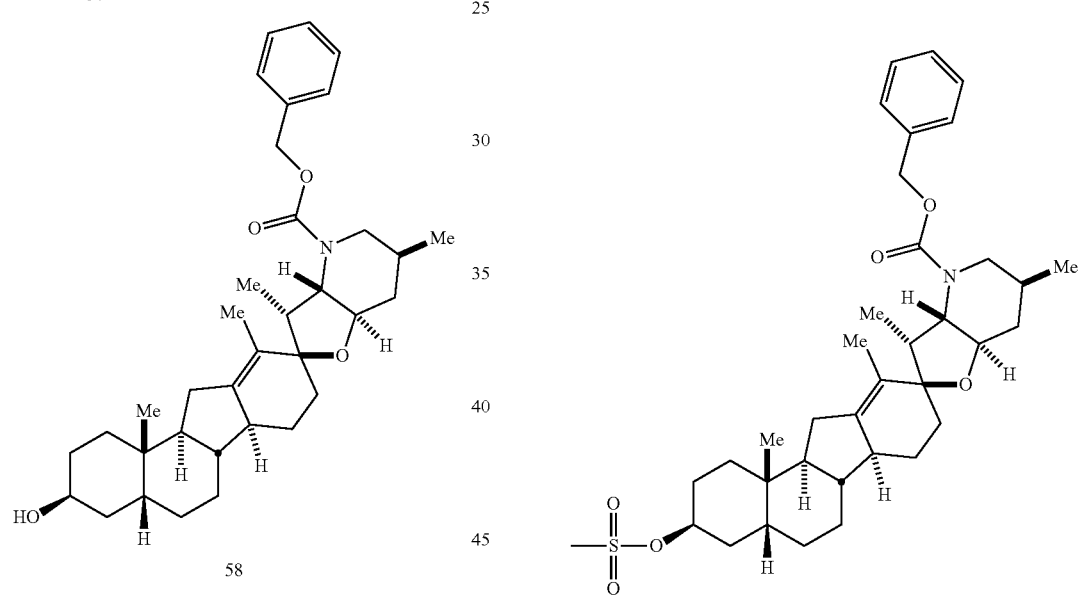

58

Step D

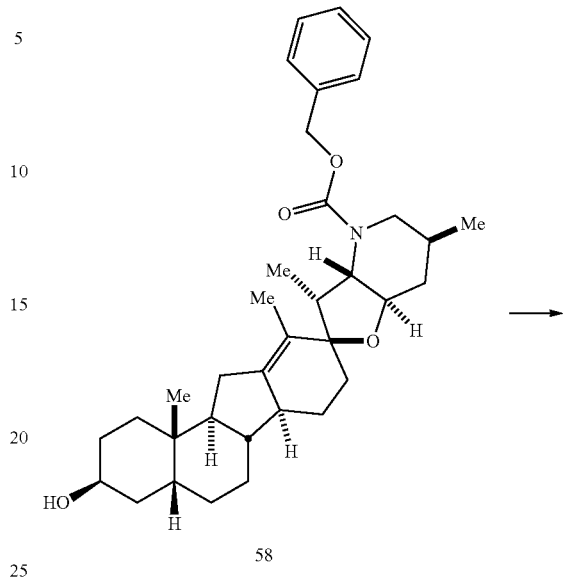

58

59

In a round-bottom flask, the ketone 57 was azeotroped a couple times with $CH_2Cl_2$ and dried under vacuum for 1 h. Under nitrogen, the ketone 2 (693 mg, 1.27 mmol, 1 equiv.) Was dissolved in anhydrous THF (20 ml) and the solution was cooled to −78 C. A 1 M solution of K-selectride in THF (1.9 ml, 1.9 mmol, 1.5 equiv.) Was added dropwise. After 1 h, the reaction was complete by TLC. The reaction was quenched by addition of 2.6 ml of 5 N naoh followed by slow addition of 2.6 ml of 30% wt $H_2O_2$. The resulting mixture was allowed to stir overnight. The mixture was partitioned between water and etoac. The aqueous layer was back extracted with etoac. The combined organic were washed first with water (buffered with a small portion of ammonium chloride) then with brine. The organic were dried, filtered, and concentrated to a crude foam (840 mg). The crude material was dissolved in $CH_2Cl_2$, loaded on a sio$_2$ column (40 g) and eluted with hexanes/etoac (0 to 50%) to give 58 (565 mg).

In a round-bottom flask under nitrogen, the alcohol 58 (530 mg, 0.98 mmol, 1 equiv.) Was dissolved in 5 ml of anhydrous $CH_2Cl_2$ and triethylamine (800 ul, 5.81 mmol, 6 equiv.). The reaction mixture was cooled to 0° C. And Ms-Cl (112 ul, 1.45 mmol, 1.5 equiv) was added dropwise. The mixture was stirred at 0° C. For 30 min. TLC (hexane:etoac, 7:3) showed ~70% conversion. 70 ul of triethylamine (70 ul, 0.5 equiv.) And Ms-Cl (10 ul, 0.1 equiv) were charged to the reaction vessel. After 90 min, a solution of saturated bicarbonate was charged and the residue was extracted with $CH_2Cl_2$. The organic layer was washed with water, dried and concentrated to a off-white foam. The material was dissolved in $CH_2Cl_2$ and purified with sio2 (40 g) eluting with hexanes/etoac (0% to 50%) to give 59 (430 mg).

Step E

Step F

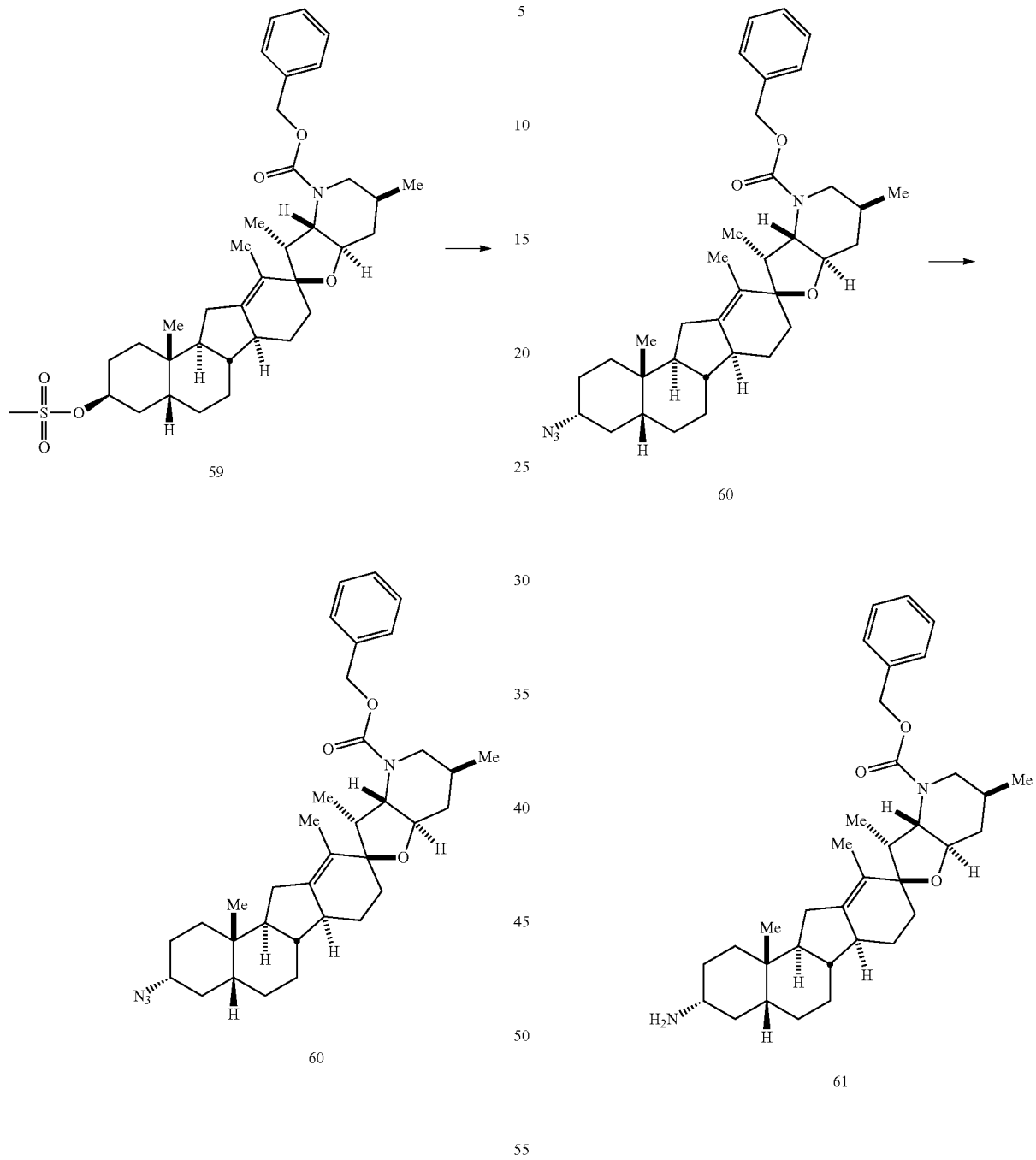

In a round-bottom flask, the mesylate 59 (420 mg, 0.67 mmol, 1 equiv.) Was dissolved in 2 ml of DMPU. The solution was treated with sodium azide (218 mg, 3.4 mmol, 5 equiv.) At 60° C. For 5 h. The mixture was cooled to 25° C., then poured into ice-water to generate a white solid. The compound was extracted with MTBE (3 times). The combined organic layers were washed with water (2×), then brine. The organic layers were dried over $Na_2SO_4$, filtered, and concentrated to a white foam (342 mg). The desired material 60 was used as is for the next step.

In a round-bottom flask equipped with a condenser, the azide 60 (336 mg, 0.58 mmol, 1 equiv.) Was dissolved in 7 ml of THF and 140 ul of water and treated with triphenylphosphine (462 mg, 1.76 mmol, 3 equiv.). The mixture was heated to 70° C. Overnight. TLC (hexane/etoac, 7:3) confirmed the reaction was complete. The reaction was concentrated to dryness. The crude material was dissolved in $CH_2Cl_2$, loaded onto 12 g of $sio_2$ and eluted with $CH_2Cl_2$/meoh (0 to 20%) to give the amine 61 (254 mg).

Step G

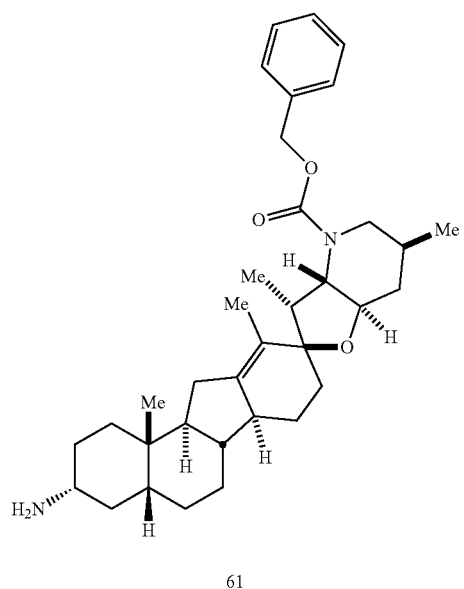

61

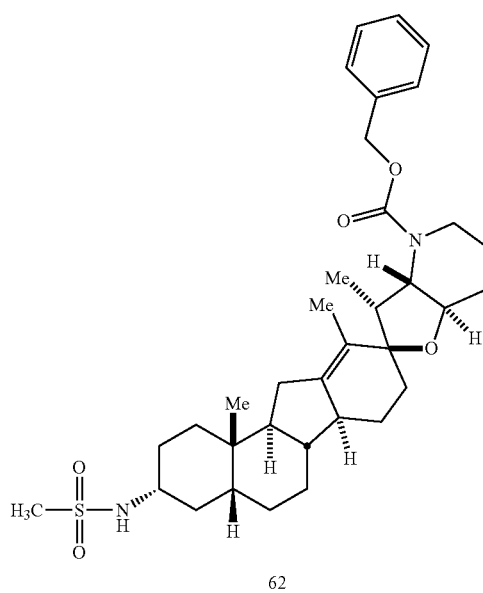

62

In a round-bottom flask under nitrogen, the amine 61 (248 mg, 0.45 mmol, 1 equiv.) Was dissolved in 7 ml of anhydrous $CH_2Cl_2$ and N,N-diisopropylethylamine (237 ul, 0.91 mmol, 2 equiv.). The reaction mixture was cooled to 0° C. And Ms-Cl (70 ul, 1.45 mmol, 1.5 equiv) was added dropwise. The mixture was stirred at 0° C. For 2 h. TLC (hexane/etoac, 7:3) showed a little amount of amine. The mixture was charged with 10 ul of Ms-Cl (0.2 equiv.), and warmed to 25° C. For 1 h. The reaction mixture was diluted with $CH_2Cl_2$ then a saturated solution of $nahco_3$. The layers were cut. The aqueous layer was extracted with one portion of $CH_2Cl_2$. The combined organic layers were washed with water, dried over $Na_2SO_4$, filtered and concentrated to dryness. The crude (326 mg) was added to a $sio_2$ column (12 g) and was eluted with hexanes/etoac (0 to 50%) to give the sulfonamide 62 (256 mg).

Step H

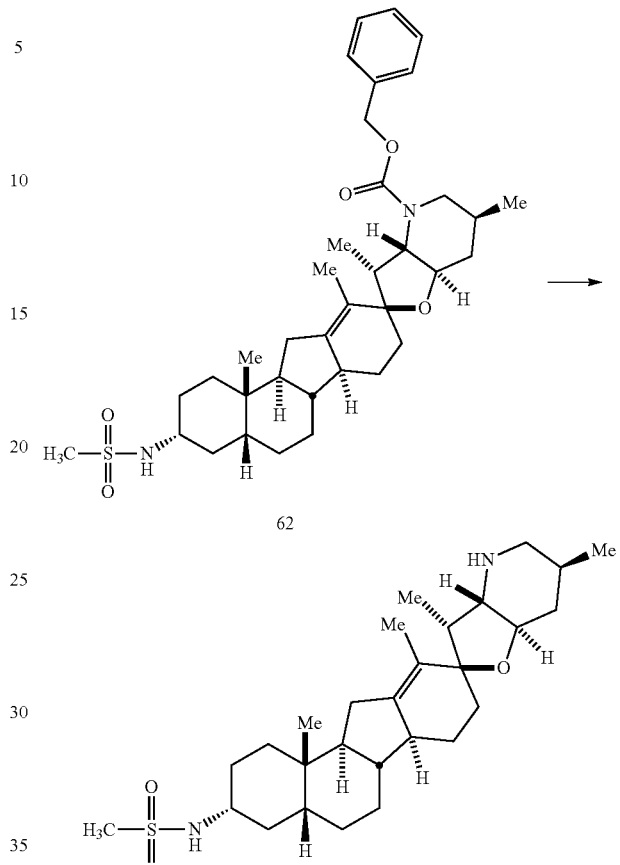

62

55

A round-bottom flask was charged with the sulfonamide 62 (250 mg, 0.4 mmol, 1 equiv.) And 50 mg of 10% Pd/C (wet, Aldrich Degussa type E101 lot 08331KC). The material was suspended in etoac (5 ml). The flask was sealed and purged three times with hydrogen and stirred under 1 atm of hydrogen. After 3 h some conversion was observed, but a lot of starting material remained. The slurry was filtered through 0.2 micron Acrodisc, washed with 2-propanol. The filtrate solution was re-subjected to the reaction condition by adding 54 mg of catalyst. The reaction was completed after 3 h. The slurry was filtered through 0.2 micron Acrodisc, washed with 2-propanol, and the solvent was concentrated to dryness. The crude material (200 mg) was loaded onto a $sio_2$ column (12 g) and the compound was eluted using a gradient $CH_2Cl_2$/meoh (0 to 10%) to give the free amine. The material was lyophilized from t-buoh/7% $H_2O$ to give 175 mg of 55 as a white powder ([M+H]=491.3 m/z).

EXAMPLE 28

Inhibition of the Hedgehog Pathway in Cell Culture

Hedgehog pathway specific cancer cell killing effects may be ascertained using the following assay. C3H10T1/2 cells differentiate into osteoblasts when contacted with the sonic hedgehog peptide (Shh-N). Upon differentiation; these osteoblasts produce high levels of alkaline phosphatase (AP) which can be measured in an enzymatic assay (Nakamura et al., *X BBRC* (1997) 237:465). Compounds that block the differentiation of C3H10T1/2 into osteoblasts (a Shh dependent event) can therefore be identified by a reduction in AP production (van der Horst et al., Bone (2003) 33:899). The assay details are described below. The results approximate ($EC_{50}$ for inhibition) of the differentiation assay is shown below in Table 1.

Assay Protocol

Cell Culture

Mouse embryonic mesoderm fibroblasts C3H10T1/2 cells (obtained from ATCC) were cultured in Basal MEM Media (Gibco/Invitrogen) supplemented with 10% heat inactivated FBS (Hyclone), 50 units/ml penicillin and 50 ug/ml streptomycin (Gibco/Invitrogen) at 37° C. With 5% CO2 in air atmosphere.

Alkaline Phosphatase Assay

C3H10T1/2 cells were plated in 96 wells with a density of $8\times10^3$ cells/well. Cells were grown to confluence (72 hrs). After sonic Hedgehog (250 ng/ml), and/or compound treatment, the cells were lysed in 110 μL of lysis buffer (50 mm Tris ph 7.4, 0.1% tritonx100), plates were sonicated and lysates spun through 0.2 μm PVDF plates (Corning). 40 μL of lysates was assayed for AP activity in alkaline buffer solution (Sigma) containing 1 mg/ml p-Nitrophenyl Phosphate. After incubating for 30 min at 37° C., the plates were read on an Envision plate reader at 405 nm. Total protein was quantified with a BCA protein assay kit from Pierce according to manufacturer's instructions. AP activity was normalized against total protein. Note that "A" indicates that the $IC_{50}$ is less than 20 nm, "B" indicates that the $IC_{50}$ is 20-100 nm, "C" indicates that the $IC_{50}$ is >100 nm.

TABLE 1

Approximate $EC_{50}$ for Inhibition

| Compound | Differentiation Assay $EC_{50}$ |
|---|---|
| 1 | A |
| 7 | C |
| 8 | C |
| 9 | C |
| 10 | C |
| 13 | A |
| 20 | A |
| 21 | B |
| 22 | A |
| 23 | A |
| 24 | A |
| 27 | B |
| 29 | B |
| 31 | B |
| 33 | C |
| 35 | A |
| 37 | A |
| 39 | B |
| 40 | A |
| 42 | A |
| 55 | A |

EXAMPLES 29

Pancreatic Cancer Model

The activity of Compound 42 was further tested in a human pancreatic model: BXPC-3 cells were implanted subcutaneously into the flanks of the right legs of mice. On day 42 post-tumor implant, the mice were randomized into two groups to receive either Vehicle (30% HPBCD) or Compound 42. Compound 42 administered orally at 40 mg/kg/day. After receiving 25 daily doses, Compound 42 statistically reduced tumor volume growth by 40% when compared to the vehicle control (p=0.0309). At the end of the study, the tumors were harvested 4 hours post the last dose to evaluate an on target response by q-RT-PCR analysis of the HH pathway genes. Analysis of human Gli-1 resulted in no modulation. Analysis of murine Gli-1 mrna levels resulted in a robust down-regulation in the Compound treated group, when compared to the Vehicle treated group. Inhibition of the hedgehog pathway in mouse cells, but not human tumor cells, indicates that one effect of the hedgehog inhibitor is to affect a tumor-stroma interaction.

EXAMPLE 30

Medulloblastoma Model

The activity of Compound 42 was also evaluated in a transgenic mouse model of medulloblastoma. Mice that are heterozygous for loss of function mutations in the tumor suppressors Patched1 (Ptch1) and Hypermethylated in Cancer (Hic1) develop spontaneous medulloblastoma. Similar to human medulloblastoma, these tumors demonstrate complete promoter hypermethylation of the remaining Hic1 allele, as well as loss of expression of the wild type Ptch1 allele. When passaged as subcutaneous allografts, these tumors grow aggressively and are Hedgehog pathway-dependent. This model was employed to evaluate the efficacy of orally administered Compound, and to correlate activity with drug exposure in plasma and tumors. Oral administration (PO) of a single dose of Compound 42 led to dose-dependent down-regulation of the HH pathway in subcutaneously implanted tumors, as measured by decreased Gli-1 mrna expression 8 hours post dose administration.

Daily (QD) administration of the Compound PO led to a dose dependent inhibition of tumor growth, with frank tumor regression seen at higher doses. The approximate effective daily oral dose for 50% inhibition of tumor growth (ED50) is 4 mg/kg. When animals were treated QD for 21 days, long term survival was observed following cessation of treatment (>60 days), with little to no tumor re-growth. This demonstrates that the hedgehog inhibitor Compound 42 inhibits both the hedgehog pathway and tumor growth in a tumor dependent on the hedgehog pathway due to a genetic mutation.

EXAMPLE 31

Lung Cancer Model

To test the activity of Compound 42 in a human SCLC tumor model, LX22 cells were implanted subcutaneously into the flank of the right leg. LX22 is primary xenograft model of SCLC derived from chemo-naive patients, which has been maintained by mouse to mouse passaging. This tumor responds to etoposide/carboplatin chemotherapy in way that closely resembles a clinical setting. LX22 regresses during chemotherapy treatment, goes through a period of remission, and then begins to recur. In the LX22 model, Compound single agent activity and its ability to modulate the chemoresistant recurrence was tested. On day 32 post tumor implant, mice were randomized into three dosing groups to receive Vehicle (30% HBPCD), Compound, or the chemotherapy combination of etoposide and carboplatin (E/P). Compound 42 was administered orally at a dose of 40 mg/kg/day, and after 16 consecutive doses there was no measurable difference between the treated and vehicle groups. Etoposide was administered i.v at 12 mg/kg on days 34, 35, 36, and 48, while Carboplatin was administered i.v.

At 60 mg/kg on days 34, 41, and 48, post tumor implant. On day 50, the E/P treated mice were further randomized to receive either Vehicle (30% HPBCD) or Compound follow up treatment. The Compound was administered at the oral multi-dose MTD of 40 mg/kg/day, and after 35 consecutive doses there was a substantial delay in tumor recurrence in the treated group, compared to the vehicle group (p=0.0101).

EXAMPLE 32

Multiple Myeloma

The ability of Compound 42 to inhibit the growth of multiple myeloma cells (MM) in vitro was tested, using human multiple myeloma cells lines (NCI-H929 and KMS12) and primary clinical bone marrow specimens derived from patients with MM. The cells were treated for 96 hours with Compound, washed, then plated in methylcellulose. Tumor colonies were quantified 10-21 days later as an indicator of cell growth potential following treatment. Treatment of cell lines or primary patient specimens resulted in decreased cell growth compared to an untreated control. Where the untreated control showed 100% growth of cells, each of the treated cell lines, as well as the clinical samples, showed less than about 25% growth.

EXAMPLE 33

Acute Myeloid Leukemia and Myelodysplastic Syndrome

The ability of Compound 42 to inhibit the in vitro growth of human cell lines derived from patients with acute myeloid leukemia (AML, cell line U937) and myelodysplastic syndrome (MDS, cell line KG1 and KG1a) was studied. Each of the cell lines was treated for 72 hours with Compound 42 (1.0 um) followed by plating in methylcellulose. Growth of these cell lines was inhibited by Compound 42, as summarized in the table below.

TABLE 2

Inhibition of cell growth in AML and MDS

| | Disease | | |
|---|---|---|---|
| | AML | MDS | |
| Cell line | U937 | KG1 | KG1a |
| % colony formation with Compound 42 (relative to vehicle control) | 43.4 | 25.1 | 34.6 |

EXAMPLE 34

Non-Hodgkin's Lymphoma (NHL) and Hodgkin's Disease (HD)

The ability of Compound 42 to inhibit the in vitro growth of human cell lines derived from patients with non-Hodgkin's lymphoma (cell lines RL and Jeko-1) and Hodgkin's disease (cell line L428) was studied. Each of the cell lines was treated for 72 hours with Compound 42 (1.0 um) followed by plating in methylcellulose. Growth of these cell lines was inhibited by Compound 42, as summarized in the table below.

TABLE 3

Inhibition of cell growth in HD and NHL

| | Disease | | |
|---|---|---|---|
| | HD | NHL | |
| Cell line | L428 | RL | Jeko-1 |
| % colony formation with Compound 42 (relative to vehicle control) | 21.4 | 14.3 | 27.4 |

Example 35

Pre-B Cell Acute Lymphocytic Leukemia

The activity of Compound 42 (1 um) against three pre-B cell acute lymphocytic leukemia cell lines (REH, RS4-11, and Nalm-6) was studied, using a transient transfection assay in which a Gli-responsive luciferase reporter was transiently transfected into cells. Treatment with Compound 42 repressed luciferase activity compared to a vehicle treated control (Table 4). This demonstrates that Compound 42 is an effective antagonist of the hedgehog pathway.

TABLE 4

Repression of luciferase activity

| Cell line | REH | RS4-11 | Nalm-6 |
|---|---|---|---|
| Relative luc activity (vehicle alone) | 6.73 | 12.97 | 8.42 |
| Relative luc activity (+Compound) | 1.12 | 1.31 | 1.44 |

The effect of Compound 42 on the growth of two of these cell lines, treated in vitro for 72 hours, was also studied. Following treatment, cells were washed and plated in methylcellulose. There was little inhibition of colony formation, but subsequent replating of colonies demonstrated a significant inhibition of cell growth (Table 5).

TABLE 5

Inhibition of cell growth in ALL

| Cell line | REH | RS4-11 |
|---|---|---|
| colony formation with Compound (relative to vehicle control) - 1° plating | 63 | 71 |
| colony formation with Compound (relative to vehicle control) - 2° plating | 9 | 11 |

Incorporation by Reference

All of the U.S. patents and U.S. published patent applications cited herein are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

It is claimed:

1. A method for treating Gorlin's syndrome in a subject, the method comprising administering to the subject a composition comprising a compound having the structure:

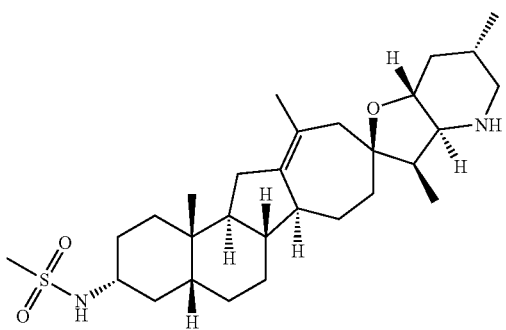

and a pharmaceutically acceptable carrier or diluent.

2. The method of claim 1, wherein the compound is in the form of a pharmaceutically acceptable salt.

3. The method of claim 2, wherein the salt is an acid salt.

4. The method of claim 3, wherein the salt is an inorganic acid salt.

5. The method of claim 3, wherein the salt is a hydrochloric acid salt.

6. The method of claim 1, wherein the compound is in the form of an iso-propanol solvate of hydrochloric acid salt of the compound.

7. The method of claim 1, wherein the composition is a liquid composition.

8. The method of claim 1, wherein the composition is in the form of a cream, ointment, or spray.

9. The method of claim 1, wherein the composition is administered topically.

10. The method of claim 1, wherein said administering is carried out in combination with an additional cancer treatment.

11. The method of claim 10, wherein said additional cancer treatment comprises radiation, surgery, or administration of a second chemotherapeutic agent.

* * * * *

UNITED STATES PATENT AND TRADEMARK OFFICE
CERTIFICATE OF CORRECTION

PATENT NO. : 10,314,827 B2
APPLICATION NO. : 16/047008
DATED : June 11, 2019
INVENTOR(S) : Alfredo C. Castro et al.

It is certified that error appears in the above-identified patent and that said Letters Patent is hereby corrected as shown below:

In the Specification

Column 1, Lines 27-30: change "Some of the work described herein was done with gov-ernment support under grant number K23 CA107040, awarded by the NIH/NCI. The government may have certain rights in the invention." to -- This invention was made with government support under CA107040, CA015396 and CA096888 awarded by the National Institutes of Health. The government has certain rights in the invention. --

Signed and Sealed this
Twenty-seventh Day of October, 2020

Andrei Iancu
*Director of the United States Patent and Trademark Office*